United States Patent

Benoit et al.

[11] Patent Number: 5,446,067
[45] Date of Patent: Aug. 29, 1995

[54] OXIME ETHERS AND FUNGICIDES CONTAINING THEM

[75] Inventors: Remy Benoit, Ludwigshafen; Hubert Sauter, Mannheim; Reinhard Kirstgen; Gisela Lorenz, both of Neustadt; Eberhard Ammermann, Ludwigshafen, all of Germany

[73] Assignee: BASF Aktiengesellschaft, Ludwigshafen, Germany

[21] Appl. No.: 273,610

[22] Filed: Jul. 12, 1994

Related U.S. Application Data

[63] Continuation of Ser. No. 832,722, Feb. 7, 1992, abandoned.

[30] Foreign Application Priority Data

Feb. 7, 1991 [DE] Germany ............ 41 03 695.6

[51] Int. Cl.⁶ .................... A01N 33/24; C07C 251/48
[52] U.S. Cl. ........................ 514/640; 514/255; 514/256; 514/269; 514/274; 514/357; 514/438; 514/448; 514/471; 514/520; 514/521; 514/524; 514/531; 514/532; 514/533; 514/534; 514/539; 514/540; 514/546; 514/548; 544/311; 544/335; 544/336; 546/329
[58] Field of Search ............ 564/256; 560/35; 514/640, 255, 269, 274, 357, 438, 448, 471, 520, 521, 524, 531, 532, 533, 534, 539, 540, 546, 548; 544/311, 335, 336; 546/329

[56] References Cited

U.S. PATENT DOCUMENTS

| | | | |
|---|---|---|---|
| 4,548,756 | 10/1985 | Martin | 560/35 |
| 4,829,085 | 5/1989 | Wenderoth et al. | 514/522 |
| 5,157,144 | 10/1992 | Anthony et al. | 560/35 |

FOREIGN PATENT DOCUMENTS

| | | |
|---|---|---|
| 0006254 | 1/1980 | European Pat. Off. . |
| 0254426 | 1/1988 | European Pat. Off. . |
| 0363818 | 4/1990 | European Pat. Off. . |
| 0407891 | 1/1991 | European Pat. Off. . |

*Primary Examiner*—Peter O'Sullivan
*Attorney, Agent, or Firm*—Oblon, Spivak, McClelland, Maier, & Neustadt

[57] ABSTRACT

Oxime ethers of the formula

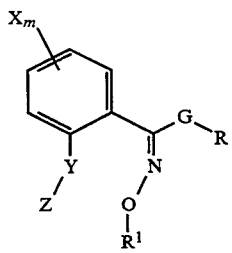

wherein m, G, R, $R^1$, X, Y, and Z are as defined herein and fungicides containing these compounds.

22 Claims, No Drawings

OXIME ETHERS AND FUNGICIDES CONTAINING THEM

This application is a Continuation of application Ser. No. 07/832,722, filed on Feb. 7, 1992, now abandoned.

The present invention relates to novel oxime ether derivatives, their preparation and their use as fungicides.

It is known to use oxime ethers, e.g. methyl 1-phenoxyimino-1-(2-phenoxymethyl)-phenylacetic, as fungicides (UP 253,213). However, this action is unsatisfactory.

We have found that novel oxime ethers of the formula I

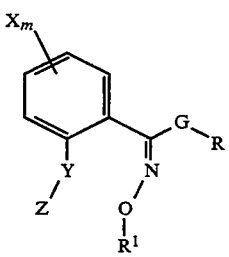

where
G is C=W or

W is oxygen or N—$R^5$,
V is O—$R^6$ or

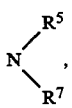

R is unsubstituted or substituted $C_3$-$C_8$-cycloalkyl, unsubstituted or substituted $C_2$-$C_8$-alkenyl, unsubstituted or substituted $C_2$-$C_8$-alkynyl, unsubstituted or substituted hetaryl or

$R^1$ is $C_1$-$C_8$-alkyl,
$R^2$ and $R^4$ are each hydrogen, $C_1$-$C_8$-alkyl, arylalkyl, hetarylalkyl, alkoxyalkyl, aryloxyalkyl, aryl or hetaryl,
$R^3$ is hydrogen, methyl, cyano or —COO—A,
A is hydrogen or $C_1$-$C_8$-alkyl or,
where $R^3$ is —COO—$C_1$-$C_8$-alkyl, $R^2$ and $R^3$ together with the carbon atom of which they are substituents form a 5-membered to 8-membered lactone ring or
$R^2$ and $R^4$ together with the carbon atom of which they are substituents form a $C_3$-$C_8$-cycloalkyl ring,
$R^5$ is hydrogen, $C_1$-$C_8$-alkyl, $C_1$-$C_4$-arylalkyl, $C_3$-$C_6$-cyclo-alkyl, hydroxyl, $C_1$-$C_4$-alkoxy, $NH_2$, $C_1$-$C_4$-alkylamino or $C_1$-$C_4$-dialkylamino,
$R^6$ and $R^7$ are each hydrogen, $C_1$-$C_8$-alkyl or $C_1$-$C_4$-alkanoyl,
$R^8$ is hydrogen or $C_1$-$C_8$-alkyl,
Y is unsubstituted or substituted $C_1$-$C_8$-alkylene, unsubstituted or substituted $C_2$-$C_8$-alkenylene, $C_2$-$C_8$-alkynylene, O, $S(O)_m$ (where m is 0, 1 or 2), or N which is substituted by unsubstituted or substituted $C_1$-$C_8$-alkyl, or is oxycarbonyl, carbonyloxy, oxycarbonyl-$C_1$-$C_8$-alkyl, carbonyloxy-$C_1$-$C_8$-alkyl, $C_2$-$C_8$-oxyalkyloxy, $C_2$-$C_8$-oxyalkenyl, $C_1$-$C_8$-alkoxy, oxy-$C_1$-$C_4$-alkyl, $C_1$-$C_8$-thioalkyl, azo, unsubstituted or $C_1$-$C_8$-alkyl-substituted carbonylamino, unsubstituted or $C_1$-$C_8$-alkyl-substituted aminocarbonyl, unsubstituted or $C_1$-$C_8$-alkyl-substituted aminocarbonyloxy, oximino or unsubstituted or substituted iminooxyalkyl,
Z is $C_1$-$C_{18}$-alkyl, $C_2$-$C_{18}$-alkenyl, $C_3$-$C_8$-alkynyl, aryl, aryl-$C_1$-$C_{10}$-alkyl, aryl-$C_2$-$C_{10}$-alkenyl, aryloxy-$C_1$-$C_{10}$-alkyl, $C_1$-$C_4$-alkoxy-$C_1$-$C_{10}$-alkyl, $C_1$-$C_{10}$-haloalkyl, $C_1$-$C_{10}$-alkoxycarbonyl or hetaryl or,
where Y is not oxyalkyl, oxyalkyloxy, thioalkyl, —O—N=C—, —N=N—, oxycarbonyl, oxycarbonyloxy, O or S, Z may additionally be aryloxy, aryloxy-$C_1$-$C_{10}$-alkoxy, aryl-$C_1$-$C_{10}$-alkoxy, $C_1$-$C_{10}$-alkoxy or hetaryloxy or,
where Y is not oxyalkyl, oxyalkyloxy, —O—N=C—, —N=N—, oxycarbonyl, oxycarbonylalkyl or O, Z may additionally be $C_1$-$C_{18}$-alkylthio or arylthio, and the radicals stated for Z are unsubstituted or substituted by halogen, cyano, nitro, $C_1$-$C_4$-alkyl, $C_2$-$C_4$-alkenyl, $C_1$-$C_4$-alkoxy, $C_1$-$C_4$-haloalkyl, $C_1$-$C_4$-alkoxy-$C_1$-$C_4$-alkyl, $C_1$-$C_4$-dialkoxy-$C_1$-$C_4$-alkyl, unsubstituted or substituted O—$C_1$-$C_{10}$-alkoximino, unsubstituted or substituted O—$C_2$-$C_{10}$-alkenyloximino, unsubstituted or substituted O-aralkyloximino, unsubstituted or substituted $C_2$-$C_{10}$-alkanoyl, unsubstituted or substituted formyl, $C_2$-$C_4$-haloalkenyl, $C_1$-$C_4$-alkoxycarbonyl, unsubstituted or substituted phenyl or unsubstituted or substituted phenoxy, or are each a carbon-bonded, unsubstituted or substituted five-membered heterocyclic structure which contains from one to four identical or different hetero atoms, ie. nitrogen, oxygen or sulfur, in which two adjacent substituents may form an unsubstituted or substituted aromatic or heteroaromatic ring, the radicals X are identical or different and are each hydrogen, halogen, nitro, unsubstituted or substituted $C_1$-$C_4$-alkyl, unsubstituted or substituted $C_1$-$C_4$-alkoxy or unsubstituted or substituted $C_1$-$C_4$-haloalkyl and
m is an integer of from 1 to 4, have a very good fungicidal action which is better than that of the known fungicides. The novel compounds also have an insecticidal action. Because of the C=N double bonds, the novel compounds of the formula I may be obtained in their preparation in the form of E—Z isomer mixtures, which can be separated into the individual components in a conventional manner, for example by crystallization or chromatography. Both the individual isomeric compounds and mixtures thereof form subjects of the invention and can be used as fungicides.

G is preferably C=W or

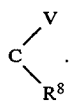

W is preferably oxygen or N—$R^5$.
V is preferably O—$R^5$ or

R is preferably phenyl, furyl, thienyl, cyclopropyl, cyclobutyl, cyclopentyl, cyclohexyl, vinyl or

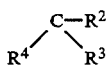

$R^1$ is preferably methyl, ethyl, isopropyl or propyl.
$R^2$ are $R^4$ are each preferably hydrogen, methyl, ethyl or propyl.
$R^3$ is preferably hydrogen or —CO—$OCH_3$.
$R^5$ is preferably methyl, ethyl, n-propyl, isopropyl or cyclopropyl.
$R^6$ is preferably hydrogen, methyl, ethyl or acetyl.
$R^7$ is preferably hydrogen.
$R^8$ is preferably hydrogen or methyl.
Y is preferably methylene, ethylene, ethenylene, ethynylene, methyleneoxy, ethyleneoxy, oxymethylene, thiomethylene, carbonyloxy, carbonyloxymethylene, aminocarbonyloxy, methylenethio, oxycarbonylmethylene, oxyethylene, ethylenethio, thioethylene, —C≡N—O—$CH_2$—, —O—N=C—, —C=N—O—, —N=N— or O or S.
Z is preferably hydrogen, halogen (eg. fluorine, chlorine or bromine), $C_1$–$C_{18}$-alkyl (eg. methyl, ethyl, n-propyl, isopropyl, n-butyl, sec-butyl, isobutyl, tertbutyl, 3-methylbutyl, 2,2-dimethylpropyl, 1,1-dimethylpropyl, 3-hexyl, n-pentyl, n-hexyl, n-heptyl, n-octyl, n-nonyl, n-decyl, n-pentadecyl, n-heptadecyl or 2,6-dimethylhept-1-yl), cyanomethyl, $C_2$–$C_9$-alkenyl (eg. vinyl, 2-propen-2-yl, 1-propen-1-yl, 2-buten-2-yl, 2-methylprop-1-en-1-yl, allyl, 2-buten-1-yl, 3-methyl-2-buten-1-yl, 1,3-pentadien-1-yl, 2,6-dimethyl-1,5-heptadien-1-yl or 2,6-dimethylhept-5-en-1-yl), $C_2$-alkynyl (eg. ethynyl or 2-phenylethynyl), $C_1$- or $C_2$-alkoxy-$C_1$- or $C_2$-alkyl (methoxymethyl, ethoxymethyl or 1-methoxyethyl), $C_3$–$C_6$-cycloalkyl (eg. cyclopropyl, cyclobutyl, cyclopentyl, cyclohexyl or 1-methylcyclopropyl), for example the following substituted cyclopropyl radicals being intended:
  2,2-dichloro-1-methylcyclopropyl (A1)
  2,2-dichloro-3,3-dimethylcyclopropyl (A2)
  2,2,3,3-tetramethylcyclopropyl (A3)
  2-(2'-methyl-1'-propenyl)-3,3-dimethylcyclopropyl (A4)
  2-(2',2'-difluorovinyl)-3,3-dimethylcyclopropyl (A5)
  2-(2',2'-dichlorovinyl)-3,3-dimethylcyclopropyl (A6)
  2-(2',2'-dibromovinyl)-3,3-dimethylcyclopropyl (A7)
  2-phenylcyclopropyl (A8)
  2-(4'-chlorophenyl)-cyclopropyl (A9)
  2,2-dichloro-3-phenylcyclopropyl (A10)
  2-carbomethoxycyclopropyl (A11) or halogen-$C_1$- or $C_2$-alkyl (eg. chloromethyl, 1-chloroethyl, dichloromethyl, trichloromethyl, bromomethyl or trifluoromethyl), unsubstituted or substituted phenyl, such as halophenyl (eg. 2-fluoro-, 3-fluoro-, 4-fluoro-, 6-fluoro-, 2-chloro-, 2,4-difluoro-, 2,6-difluoro-, 2,3,4,5,6-pentafluoro-, 2-chloro-, 3-chloro-, 4-chloro-, 2,5-dichloro-, 2,5-dichloro-, 2,6-dichloro-, 3,4-dichloro-, 3,5-dichloro-, 2,4,5-trichloro-, 2,3,4,5,6-pentachloro-, 2-bromo-, 3-bromo- or 4-bromophenyl), $C_1$–$C_4$-alkylphenyl (eg. 2-methyl-, 3-methyl-, 2,3-dimethyl-, 2,4-dimethyl-, 2,5-dimethyl-, 2,6-dimethyl-, 3,4-dimethyl-, 3,5-dimethyl-, 2,4,6-trimethyl- or 4-tert-butylphenyl), arylphenyl (eg. 2-phenyl- or 4-phenylphenyl), halo-$C_1$-alkylphenyl (eg. 2-trifluoro-, 3-trifluoro-or 4-trifluoromethylphenyl), $C_1$–$C_4$-alkoxyphenyl (eg. 2-methoxy-, 3-methoxy-, 4-methoxy-, 3,4-dimethoxy-, 3,4,5-trimethoxy- or 4-tert-butoxyphenyl), 2-, 3- or 4-phenoxyphenyl, $C_1$–$C_4$-alkanoylphenyl (eg. 4-acetyl, 3-acetyl, 2-acetyl or 4-acetyl-2-methylphenyl), formylphenyl (eg. 2-formyl-, 3-formyl- or 4-formylphenyl), $C_1$–$C_4$-dialkoxy-$C_1$–$C_4$-alkylphenyl (eg. 4-(1,1-dimethoxyethyl)-, 4-(dimethoxymethyl)-, 3-(1,1-dimethoxyethyl)-, 3-(dimethoxymethyl)- or 4-(1,1-dimethoxyethyl)-2-methylphenyl), $C_1$–$C_{10}$-O-alkoximinophenyl (eg. 4-[1-(O-ethoximino)-ethyl]-, 4-(O-ethoximinomethyl)-, 3-[1-(O-ethoximino)-ethyl]-, 3-(O-ethoximinomethyl)-, 4-[1-(O-ethoximino)-ethyl]-2-methyl-, 4-[1-(O-hexyloximino)-ethyl]-, 4(O-hexyloximinomethyl)-, 3-[1-(O-hexyloximino)-ethyl]-, 3-(O-hexyloximinomethyl)-, 4-[1-(O-hexyloximino)-ethyl]-2-methyl-, 4-[1-(O-isobutoximino)-ethyl]-, 4-(O-isobutoximinoethyl)-, 3-[1-(O-isobutoximino)-ethyl]-, 3-(O-isobutoximinomethyl)- or 4-[1-(O-isobutoximino)-ethyl]- 2-methylphenyl), $C_2$–$C_{10}$-alkenyloximinophenyl (eg. 4-[1-(O-2-buten-1-oximino)-ethyl]-, 4-(O-2-buten-1-oximinomethyl)-, 3-[1-(O-2-buten-1-oximino)-ethyl]-, 3-(O-2-buten-1-oximinomethyl)- or 4-[1-(O-2-buten-1-oximino)ethyl]-2-methylphenyl), $C_1$–$C_{10}$-arylalkyloximinophenyl (eg. 4-[1-(O-benzyloximino)-ethyl]-, 4-(O-benzyloximinomethyl)-, 3-[1-(O-benzyloximino)-ethyl]-, 3-(O-benzyloximinomethyl)- or 4-[1-(O-benzyloximino)-ethyl]-2-methylphenyl, substituted benzyl (eg. halobenzyl, 2-fluoro-, 3-fluoro-, 4-fluoro-, 2-chloro-, 3-chloro-, 4-chloro-, 2-chloro-, 6-fluoro-, 2,4-dichloro-, 2,6-dichloro-, 3,5-dichloro-, 2,4,6-trichloro-, 2-bromo-, 3-bromo-, 4-bromo-, 2-methyl-, 3-methyl-, 4-methyl-, 4-tert-butyl-, 2,4-dimethyl-, 2,6 -dimethyl-, 2,4,6-trimethyl-, 2-methoxy-, 3-methoxy-, 4-methoxy-, 2-trifluoromethyl-, 3-trifluoromethyl-, 4-trifluoromethyl-, 4-tert-butoxy-, 4-phenoxy-, 4-phenylbenzyl-, -methylethyl-, -isopropyl-, -hydroxyl-, 2-methoxyhydroxy-, 4-methoxyhydroxy-, 3,4-dimethoxyhydroxy-, 2-methoxymethoxy-, 4-methoxymethoxy- or 3,4-dimethoxymethoxybenzyl), unsubstituted or substituted phenethyl (eg. phenyl-, 1-methyl-2-phenyl-, 2(para-tert-butylphenyl)-, 2-(para-tert-butylphenyl)-1-methyl-, 2-(ortho-chlorophenyl)-, 2-(meta-chlorophenyl) or 2-(para-chlorophenyl)-ethyl), unsubstituted or substituted styryl (eg. styryl, 2'-chloro-, 3'-chloro-, 4'-chloro-, 2',4'-dichloro-, 2'-fluoro-, 4'-fluoro-, 2'-methyl-, 4'-methyl-, 4'-tert-butyl-, 2'-methoxy-, 4'-methoxy- or 4'-phenoxystyryl), phenyl-$C_3$–$C_6$-alkyl (eg. 3-phenylpropyl, 2-methyl-3-phenylpropyl, 4-phenylbutyl, 5-phenylpentyl, 6-phenylhexyl or 3-(4'-tertbutylphenyl)-2-methylpropyl, aryloxy (if Y is O, S, oxycarbonyl, oxyalkoxy, oximino, thioalkyl, —N═N—, oxycarbonylalkyl or oxyalkyl), such as substituted phenoxy (eg. 2-chloro-, 3-chloro-, 4-chloro-, 2-methyl-, 4-methyl-, 2-methoxy-, 4-methoxy-, 2-trifluoromethyl- or 4-trifluoromethylphenoxy), aryloxy-$C_1$-$C_6$-alkyl, such as unsubstituted or substituted phenoxymethyl (eg. 2-chloro-, 2-methyl-, 4-methyl-, 2-methoxy-, 4-methoxy- or 4-tert-butylphenoxymethyl), unsubstituted or substituted phenoxyethyl (eg. 2-chloro-, 4-chloro-, 4-fluoro-, 2-methyl-, 4-methyl-, 2-methoxy-, 4-methoxy- or 4-tert-butylphenoxyethyl), unsubstituted or substituted $C_3$-$C_6$-phenoxyalkyl (eg. 3-phenoxypropyl, 3-(ortho-chlorophenoxy)-propyl, 3-(parachlorophenoxy)-propyl, 4-phenoxybutyl, 4-(ortho-chlorophenoxy)-butyl, 4-(para-chlorophenoxybutyl), 5-phenoxypentyl, 5-(ortho-chlorophenoxy)-pentyl, 5-(para-chlorophenoxy)-pentyl or 6-phenoxyhexyl), phenoxyethoxy (if Y is O, S, oxycarbonyl, oxyalkoxy, oximino, thioalkyl, —N═N—, oxycarbonylalkyl or oxyalkyl), methoxycarbonyl, tert-butoxycarbonyl, unsubstituted or substituted hetaryl (eg. furyl, 2-furyl, 3-furyl, 5-nitro-2- or 3-furyl, 5-chloro-2- or 3-furyl, benzofuran-2- or -3-yl, thienyl, 2thienyl, 3-thienyl, 5-nitro-2- or -3-thienyl, 5-chloro-2- or -3-thienyl or benzothien-2- or -3-yl, N-methyl-pyrrol-2- or -3-yl, N-methylpyrazol-3-, -4- or -5-yl, N-methylimidazol-2-, -4- or -5-yl, 1-methyl-1,2,3-triazol-4- or -5-yl, 1-methyl-1,2,4-triazol-3- or -5-yl, 1-methyltetrazol-5-yl, isoxazol-3-, -4- or -5-yl, benzoisoxazol-3-yl, benzoxazol-2-yl, oxazol-2-, -4- or -5-yl, thiazol-2-, -4-or -5-yl, benzothiazol-2-yl, benzoisothiazol-3-yl, isothiazol-3-, -4- or -5-yl, 1,2,3-thiadiazol-4-yl, 1,2,4-thiadiazol-5-yl, 1,3,4-thiadiazol-3-yl, 1,3-thiazol-[4,5-b]pyridin-2-yl, substituted hetalkenyl (eg. 2-(2'- or 3'-furyl)-, 2-(5'-nitro-2'- or -3'-furyl)-, 2-(2'- or 3'-thienyl)- or 2-(5'-nitro-2'- or 3'-thienyl)-ethenyl).

Other preferred compounds are the oxime ethers of the formula I, where

G is C═W,
W is oxygen,
R is $C_3$-$C_8$-cycloalkyl, $C_2$-$C_8$-alkynyl, unsubstituted or substituted hetaryl or

$R^1$ is $C_1$-$C_6$-alkyl,
$R^2$ and $R^4$ are each hydrogen, $C_1$-$C_8$-alkyl or $C_3$-$C_8$-cycloalkyl or are each phenyl which is unsubstituted or substituted by $C_1$-$C_4$-alkyl, $C_1$-$C_4$-alkoxy or halogen,
$R^3$ is hydrogen,
Y is methylene, ethylene, ethenylene, ethynylene, methyleneoxy, ethyleneoxy, oxymethylene, thiomethylene, carbonyloxy, carbonyloxymethylene, aminocarbonyloxy, methylenethio, oxycarbonylmethylene, oxyethylene, ethylenethio, thioethylene, —C═N—O—CH$_2$—, —O—N═C—, —C═N—O—, —N═N— or O or S,
Z is straight-chain or branched $C_1$-$C_{10}$-alkyl, $C_2$-$C_{10}$-alkenyl, $C_2$-$C_{10}$-alkynyl, phenyl, pyridyl, pyridazinyl, pyrimidinyl, pyrazinyl, quinolyl, isoquinolyl, naphthyridyl, quinoxalyl, thienyl, furyl, pyrrolyl, oxazolyl, isoxazolyl, pyrazolyl, imidazolyl, thiazolyl, isothiazolyl, benzothiazolyl, benzoisothiazolyl, benzoxazolyl, benzoisoxazolyl, benzopyrrazolyl, benzoimidazolyl, indolyl, isoindolyl, benzothiophenyl, isobenzothiophenyl, benzofuranyl, isobenzofuranyl or, only when Y is not oxymethylene, oxyethylene, oxycarbonyl, oxycarbonylmethylene, thiomethylene, thioethylene, —O—N═C—, —N═N—, O or S, straight-chain or branched $C_1$-$C_{10}$-alkoxy, $C_2$-$C_{10}$-alkenyloxy, phenyloxy, pyridyloxy, pyridazinyloxy, pyrimidinyloxy, pyrazinyloxy, quinolyloxy, isoquinolyloxy, naphthyridyloxy, quinoxalyloxy, thienyloxy, furyloxy, pyrrolyloxy, oxazolyloxy, isoxazolyloxy, pyrazolyloxy, imidazolyloxy, thiazolyloxy, isothiazolyloxy, benzothiazolyloxy, benzoisothiazolyloxy, benzoxazolyloxy, benzoisoxazolyloxy, benzopyrazolyloxy, benzoimidazolyloxy, indolyloxy, isoindolyloxy, benzothiophenoxy, isobenzothiophenoxy, benzofuranyloxy, isobenzofuranyloxy or, only when Y is not oxymethylene, oxyethylene, oxycarbonyl, oxycarbonylmethylene, —O—N═C—, —N═N— or O, straight-chain or branched $C_1$-$C_{10}$-alkylthio, $C_2$-$C_{10}$-alkenylthio, phenylthio, pyridylthio, pyridazinylthio, pyrimidinylthio, pyrazinylthio, quinolylthio, isoquinolylthio, naphthyridylthio, quinoxalylthio, thienylthio, furylthio, pyrrolylthio, oxazolylthio, isoxazolylthio, pyrazolylthio, imidazolylthio, thiazolylthio, isothiazolylthio, benzothiazolylthio, benzoisothiazolylthio, benzoxazolylthio, benzoisoxazolylthio, benzopyrazolylthio, benzoimidazolylthio, indolylthio, isoindolylthio, benzothiophenylthio, isobenzothiophenylthio, benzofuranylthio or isobenzofuranylthio, and the radicals stated for Z are unsubstituted or substituted by halogen, cyano, straight-chain or branched $C_1$-$C_4$-alkyl, $C_2$-$C_4$-alkenyl, $C_2$-$C_4$-alkynyl, hydroximino, $C_1$-$C_4$-carboxyalkoxy, $C_1$-$C_4$-alkanoyl, $C_1$-$C_4$-alkoxyalkyl, $C_1$-$C_4$-dialkoxyalkyl, O-alkyloximino, O-alkenyloximino, O-arylalkyloximino, $C_1$-$C_4$-dialkoxy-$C_1$-$C_4$-alkyl or formyl,
X is hydrogen, halogen, cyano, straight-chain or branched $C_1$-$C_4$-alkyl, $C_1$-$C_4$-haloalkyl or $C_1$-$C_4$-alkoxy and
m is an integer of from 1 to 4.

Other preferred compounds are oxime ethers of the formula I, where

G is C═W,
W is N—$R^5$,
R is $C_3$-$C_8$-cycloalkyl, unsubstituted or substituted hetaryl or

$R^1$ is $C_1$-$C_6$-alkyl,
$R^2$ and $R^4$ are each hydrogen, $C_1$-$C_8$-alkyl or $C_3$-$C_8$-cycloalkyl or are each phenyl which is unsubstituted or substituted by $C_1$-$C_4$-alkyl, $C_1$-$C_4$-alkoxy or halogen,
$R^3$ is hydrogen, $R^5$ is $C_1$–$C_8$-alkyl, $C_1$–$C_4$-arylalkyl, $C_3$–$C_6$-cycloalkyl, hydroxyl, $C_1$–$C_4$-alkoxy, $NH_2$, $C_1$–$C_4$-alkylamino or $C_1$–$C_4$-dialkylamino, Y is methylene, ethylene, ethenylene, ethynylene, methyleneoxy ethyleneoxy, oxymethylene, thiomethylene, carbonyloxy, carbonyloxymethylene, aminocarbonyloxy, methylenethio, oxycarbonylmethylene, oxyethylene, ethylenethio, thioethylene, —C≡N—O—CH$_2$—, —O—N≡C—, —C≡N—O—, —N≡N— or O or S, Z is straight-chain or branched $C_1$–$C_{10}$-alkyl, $C_2$–$C_{10}$-alkenyl, $C_2$–$C_{10}$-alkynyl, phenyl, pyridyl, pyridazinyl, pyrimidinyl, pyrazinyl, quinolyl, isoquinolyl, naphthyridyl, quinoxalyl, thienyl, furyl, pyrrolyl, oxazolyl, isoxazolyl, pyrazolyl, imidazolyl, thiazolyl, isothiazolyl, benzothiazolyl, benzoisothiazolyl, benzoxazolyl, benzoisoxazolyl, benzopyrrazolyl, benzoimidazolyl, indolyl, isoindolyl, benzothiophenyl, isobenzothiophenyl, benzofuranyl, isobenzofuranyl or, only when Y is not oxymethylene, oxyethylene, oxycarbonyl, oxycarbonylmethylene, thiomethylene, thioethylene, —O—N≡C—, —N≡N—, O or S, straight-chain or branched $C_1$–$C_{10}$-alkoxy, $C_2$–$C_{10}$-alkenyloxy, phenyloxy, pyridyloxy, pyridazinyloxy, pyrimidinyloxy, pyrazinyloxy, quinolyloxy, isoquinolyloxy, naphthyridyloxy, quinoxalyloxy, thienyloxy, furyloxy, pyrrolyloxy, oxazolyloxy, isoxazolyloxy, pyrazolyloxy, imidazolyloxy, thiazolyloxy, isothiazolyloxy, benzothiazolyloxy, benzoisothiazolyloxy, benzoxazolyloxy, benzoisoxazolyloxy, benzopyrazolyloxy, benzoimidazolyloxy, indolyloxy, isoindolyloxy, benzothiophenoxy, isobenzothiophenoxy, benzofuranyloxy, isobenzofuranyloxy or, only when Y is not oxymethylene, oxyethylene, oxycarbonyl, oxycarbonylmethylene, —N≡C—, —N≡N— or O, straight-chain or branched $C_1$–$C_{10}$-alkylthio, $C_2$–$C_{10}$-alkenylthio, phenylthio, pyridylthio, pyridazinylthio, pyrimidinylthio, pyrazinylthio, quinolylthio, isoquinolylthio, naphthyridylthio, quinoxalylthio, thienylthio, furylthio, pyrrolylthio, oxazolylthio, isoxazolylthio, pyrazolylthio, imidazolylthio, thiazolylthio, isothiazolylthio, benzothiazolylthio, benzoisothiazolylthio, benzoxazolylthio, benzoisoxazolylthio, benzopyrazolylthio, benzoimidazolylthio, indolylthio, isoindolylthio, benzothiophenylthio, isobenzothiophenylthio, benzofuranylthio or isobenzofuranylthio, and the radicals stated for Z are unsubstituted or substituted by halogen, cyano, straight-chain or branched $C_1$–$C_4$-alkyl, $C_2$–$C_4$-alkenyl, $C_2$–$C_4$-alkynyl, hydroximino, $C_1$–$C_4$-carboxyalkoxy, $C_1$–$C_4$-alkanoyl, $C_1$–$C_4$-alkoxyalkyl, $C_1$–$C_4$-dialkoxyalkyl, O-alkyloximino, O-alkenyloximino, O-arylalkyloximino, $C_1$–$C_4$-dialkoxy-$C_1$–$C_4$-alkyl or formyl, X is hydrogen, halogen, cyano, straight-chain or branched $C_1$–$C_4$-alkyl, $C_1$–$C_4$-haloalkyl or $C_1$–$C_4$-alkoxy and m is an integer of from 1 to 4.

Other preferred compounds are oxime ethers of the formula I, where

G is C≡W,
W is oxygen,
R is

$R^1$ is $C_1$–$C_6$-alkyl, $R^2$ and $R^4$ are each hydrogen, $C_1$–$C_8$-alkyl or $C_3$–$C_8$-cycloalkyl or are each phenyl which is unsubstituted or substituted by $C_1$–$C_4$-alkyl, $C_1$–$C_4$-alkoxy or halogen, $R^3$ is cyano or $R^2$ and $R^4$ together with the carbon atom of which they are substituents form a $C_3$–$C_8$-cycloalkyl ring, Y is methylene, ethylene, ethenylene, ethynylene, methyleneoxy, ethyleneoxy, oxymethylene, thiomethylene, carbonyloxy, carbonyloxymethylene, aminocarbonyloxy, methylenethio, oxycarbonylmethylene, oxyethylene, ethylenethio, thioethylene, —C≡N—O—CH$_2$—, —O—N≡C—, —C≡N—O—, —N≡N— or O or S, Z is straight-chain or branched $C_1$–$C_{10}$-alkyl, $C_2$–$C_{10}$-alkenyl, $C_2$–$C_{10}$-alkynyl, phenyl, pyridyl, pyridazinyl, pyrimidinyl, pyrazinyl, quinolyl, isoquinolyl, naphthyridyl, quinoxalyl, thienyl, furyl, pyrrolyl, oxazolyl, isoxazolyl, pyrazolyl, imidazolyl, thiazolyl, isothiazolyl, benzothiazolyl, benzoisothiazolyl, benzoxazolyl, benzoisoxazolyl, benzopyrrazolyl, benzoimidazolyl, indolyl, isoindolyl, benzothiophenyl, isobenzothiophenyl, benzofuranyl, isobenzofuranyl or, only when Y is not oxymethylene, oxyethylene, oxycarbonyl, oxycarbonylmethylene, thiomethylene, thioethylene, —N≡C—, —N≡N—, O or S, straight-chain or branched $C_1$–$C_{10}$-alkoxy, $C_2$–$C_{10}$-alkenyloxy, phenyloxy, pyridyloxy, pyridazinyloxy, pyrimidinyloxy, pyrazinyloxy, quinolyloxy, isoquinolyloxy, naphthyridyloxy, quinoxalyloxy, thienyloxy, furyloxy, pyrrolyloxy, oxazolyloxy, isoxazolyloxy, pyrazolyloxy, imidazolyloxy, thiazolyloxy, isothiazolyloxy, benzothiazolyloxy, benzoisothiazolyloxy, benzoxazolyloxy, benzoisoxazolyloxy, benzopyrazolyloxy, benzoimidazolyloxy, indolyloxy, isoindolyloxy, benzothiophenoxy, isobenzothiophenoxy, benzofuranyloxy, isobenzofuranyloxy or, only when Y is not oxymethylene, oxyethylene, oxycarbonyl, oxycarbonylmethylene, —O—N≡C—, —N≡N— or O, straight-chain or branched $C_1$–$C_{10}$-alkylthio, $C_2$–$C_{10}$-alkenylthio, phenylthio, pyridylthio, pyridazinylthio, pyrimidinylthio, pyrazinylthio, quinolylthio, isoquinolylthio, naphthyridylthio, quinoxalylthio, thienylthio, furylthio, pyrrolylthio, oxazolylthio, isoxazolylthio, pyrazolylthio, imidazolylthio, thiazolylthio, isothiazolylthio, benzothiazolylthio, benzoisothiazolylthio, benzoxazolylthio, benzoisoxazolylthio, benzopyrazolylthio, benzoimidazolylthio, indolylthio, isoindolylthio, benzothiophenylthio, isobenzothiophenylthio, benzofuranylthio or isobenzofuranylthio, and the radicals stated for Z are unsubstituted or substituted by halogen, cyano, straight-chain or branched $C_1$–$C_4$-alkyl, $C_2$–$C_4$-alkenyl, $C_2$–$C_4$-alkynyl, hydroximino, $C_1$–$C_4$-carboxyalkoxy, $C_1$–$C_4$-alkanoyl, $C_1$–$C_4$-alkoxyalkyl, $C_1$–$C_4$-dialkoxyalkyl, O-alkyloximino, O-alkenyloximino, O-arylalkyloximino, $C_1$–$C_4$-dialkoxy-$C_1$–$C_4$-alkyl or formyl, X is hydrogen, halogen, cyano, straight-chain or branched $C_1$–$C_4$-alkyl, $C_1$–$C_4$-haloalkyl or $C_1$–$C_4$-alkoxy and m is an integer of from 1 to 4.

Other preferred compounds are oxime ethers of the formula I, where

G is C=W,

W is oxygen,

R is

$R^1$ is $C_1$–$C_6$-alkyl, $R^2$ and $R^4$ are each hydrogen, $C_1$–$C_8$-alkyl, $C_3$–$C_8$-cycloalkyl or are each phenyl which is unsubstituted or substituted by $C_1$–$C_4$-alkyl, $C_1$–$C_4$-alkoxy or halogen, $R^3$ is —COO—A, A is hydrogen, methyl, ethyl, isopropyl, propyl, n-butyl, sec-butyl or tert-butyl or, where $R^3$ is —COO—$C_1$–$C_8$-alkyl, $R^2$ and $R^3$ together with the carbon atom of which they are substituents form a 5-membered to 8-membered lactone ring, or $R^2$ and $R^4$ together with the carbon atom of which they are substituents form a $C_3$–$C_8$-cycloalkyl ring, Y is methylene, ethylene, ethenylene, ethynylene, methyleneoxy, ethyleneoxy, oxymethylene, thiomethylene, carbonyloxy, carbonyloxymethylene, aminocarbonyloxy, methylenethio, oxycarbonylmethylene, oxyethylene, ethylenethio, thioethylene, —C=N—O—CH$_2$—, —O—N=C—, —C=N—O—, —N=N— or O or S, Z is straight-chain or branched $C_1$–$C_{10}$-alkyl, $C_2$–$C_{10}$-alkenyl, $C_2$–$C_{10}$-alkynyl, phenyl, pyridyl, pyridazinyl, pyrimidinyl, pyrazinyl, quinolyl, isoquinolyl, naphthyridyl, quinoxalyl, thienyl, furyl, pyrrolyl, oxazolyl, isoxazolyl, pyrazolyl, imidazolyl, thiazolyl, isothiazolyl, benzothiazolyl, benzoisothiazolyl, benzoxazolyl, benzoisoxazolyl, benzopyrrazolyl, benzoimidazolyl, indolyl, isoindolyl, benzothiophenyl, isobenzothiophenyl, benzofuranyl, isobenzofuranyl or, only when Y is not oxymethylene, oxyethylene, oxycarbonyl, oxycarbonylmethylene, thiomethylene, thioethylene, —O—N=C—, —N=N—, O or S, straight-chain or branched $C_1$–$C_{10}$-alkoxy, $C_2$–$C_{10}$-alkenyloxy, phenyloxy, pyridyloxy, pyridazinyloxy, pyrimidinyloxy, pyrazinyloxy, quinolyloxy, isoquinolyloxy, naphthyridyloxy, quinoxalyloxy, thienyloxy, furyloxy, pyrrolyloxy, oxazolyloxy, isoxazolyloxy, pyrazolyloxy, imidazolyloxy, thiazolyloxy, isothiazolyloxy, benzothiazolyloxy, benzoisothiazolyloxy, benzoxazolyloxy, benzoisoxazolyloxy, benzopyrazolyloxy, benzoimidazolyloxy, indolyloxy, isoindolyloxy, benzothiophenoxy, isobenzothiophenoxy, benzofuranyloxy, isobenzofuranyloxy or, only when Y is not oxymethylene, oxyethylene, oxycarbonyl, oxycarbonylmethylene, —O—N=C—, —N=N— or O, straight-chain or branched $C_1$–$C_{10}$-alkylthio, $C_2$–$C_{10}$-alkenylthio, phenylthio, pyridylthio, pyridazinylthio, pyrimidinylthio, pyrazinylthio, quinolylthio, isoquinolylthio, naphthyridylthio, quinoxalylthio, thienylthio, furylthio, pyrrolylthio, oxazolylthio, isoxazolylthio, pyrazolylthio, imidazolylthio, thiazolylthio, isothiazolylthio, benzothiazolylthio, benzoisothiazolylthio, benzoxazolylthio, benzoisoxazolylthio, benzopyrazolylthio, benzoimidazolylthio, indolylthio, isoindolylthio, benzothiophenylthio, isobenzothiophenylthio, benzofuranylthio or isobenzofuranylthio, and the radicals stated for Z are unsubstituted or substituted by halogen, cyano, straight-chain or branched $C_1$–$C_4$-alkyl, $C_1$–$C_4$-alkenyl, $C_2$–$C_4$-alkynyl, hydroximino, $C_1$–$C_4$-carboxyalkoxy, $C_1$–$C_4$-alkanoyl, $C_1$–$C_4$-alkoxyalkyl, $C_1$–$C_4$-dialkoxyalkyl, O-alkyloximino, O-alkenyloximino, O-arylalkyloximino, $C_1$–$C_4$-dialkoxy-$C_1$–$C_4$-alkyl or formyl, X is hydrogen, halogen, cyano, straight-chain or branched $C_1$–$C_4$-alkyl, $C_1$–$C_4$-haloalkyl or $C_1$–$C_4$-alkoxy and m is an integer of from 1 to 4.

Other preferred compounds are oxime ethers of the G is

V is O—$R^6$,

R is $C_3$–$C_8$-cycloalkyl, unsubstituted or substituted $C_2$–$C_8$-alkenyl, unsubstituted or substituted $C_2$–$C_8$-alkynyl, unsubstituted or substituted hetaryl or

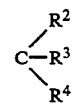

$R^1$ is $C_1$–$C_8$-alkyl, $R^2$ and $R^4$ are each hydrogen, $C_1$–$C_8$-alkyl or $C_3$–$C_8$-cycloalkyl or are each phenyl which is unsubstituted or substituted by $C_1$–$C_4$-alkyl, $C_1$–$C_4$-alkoxy or halogen, $R^3$ is hydrogen, methyl, cyano or —COO—A—, A is hydrogen, methyl, ethyl, isopropyl, propyl, n-butyl, sec-butyl-or tert-butyl or, where $R^3$ is —COO—$C_1$–$C_8$-alkyl, $R^2$ and $R^3$ together with the carbon atom of which they are substituents form a 5-membered to 8-membered lactone ring, or $R^2$ and $R^4$ together with the carbon atom of which they are substituents form a $C_3$–$C_8$-cycloalkyl ring, $R^6$ is hydrogen, $C_1$–$C_8$-alkyl or $C_1$–$C_4$-alkanoyl, $R^8$ is hydrogen or $C_1$–$C_8$-alkyl, Y is methylene, ethylene, ethenylene, ethynylene, methyleneoxy, ethyleneoxy, oxymethylene, thiomethylene, carbonyloxy, carbonyloxymethylene, aminocarbonyloxy, methylenethio, oxycarbonylmethylene, oxyethylene, ethylenethio, thioethylene, —C=N—O—CH$_2$—, —O—N=C—, —C=N—O—, —N=N— or O or S, Z is straight-chain or branched $C_1$–$C_{10}$-alkyl, $C_2$–$C_{10}$-alkenyl, $C_1$–$C_{10}$-alkynyl, phenyl, pyridyl, pyridazinyl, pyrimidinyl, pyrazinyl, quinolyl, isoquinolyl, naphthyridyl, quinoxalyl, thienyl, furyl, pyrrolyl, oxazolyl, isoxazolyl, pyrazolyl, imidazolyl, thiazolyl, isothiazolyl, benzothiazolyl, benzoisothiazolyl, benzoxazolyl, benzoisoxazolyl, benzopyrrazolyl, benzoimidazolyl, indolyl, isoindolyl, benzothiophenyl, isobenzothiophenyl, benzofuranyl, isobenzofuranyl or, only when Y is not oxymethylene, oxyethylene, oxycarbonyl, oxycarbonylmethylene, thiomethylene, thioethylene, —O—N=C—, —N=N—, O or S, straight-chain or branched $C_1$–$C_{10}$-alkoxy, $C_1$–$C_{10}$-alkenyloxy, phenyloxy, pyridyloxy, pyridazinyloxy, pyrimidinyloxy, pyrazinyloxy, quinolyloxy, isoquinolyloxy, naphthyridyloxy, quinoxalyloxy, thienyloxy, furyloxy, pyrrolyloxy, oxazolyloxy, isoxazolyloxy, pyrazolyloxy, imidazolyloxy, thiazolyloxy, isothiazolyloxy, benzothiazolyloxy, benzoisothiazolyloxy, benzoxazolyloxy, benzoisoxazolyloxy, benzopyrazolyloxy, benzoimidazolyloxy, indolyloxy, isoindolyloxy, benzothiophenoxy, isobenzothiophenoxy, benzofuranyloxy, isobenzofuranyloxy or, only when Y is not oxymethylene, oxyethylene, oxycarbonyl, oxycarbonylmethylene, —O—N=C—, —N=N— or O, straight-chain or branched $C_1$–$C_{10}$-alkylthio, $C_2$–$C_{10}$-alkenylthio, phenylthio, pyridylthio, pyridazinylthio, pyrimidinylthio, pyrazinylthio, quinolylthio, isoquinolylthio, naphthyridylthio, quinoxalylthio, thienylthio, furylthio, pyrrolylthio, oxazolylthio, isoxazolylthio, pyrazolylthio, imidazolylthio, thiazolylthio, isothiazolylthio, benzothiazolylthio, benzoisothiazolylthio, benzoxazolylthio, benzoisoxazolylthio, benzopyrazolylthio, benzoimidazolylthio, indolylthio, isoindolylthio, benzothiophenylthio, isobenzothiophenylthio, benzofuranylthio or isobenzofuranylthio, and the radicals stated for Z are unsubstituted or substituted by halogen, cyano, straight-chain or branched $C_1$–$C_4$-alkyl, $C_1$–$C_4$-alkenyl, $C_2$–$C_4$-alkynyl, hydroximino, $C_1$–$C_4$-carboxyalkoxy, $C_1$–$C_4$-alkanoyl, $C_1$–$C_4$-alkoxyalkyl, $C_1$–$C_4$-dialkoxyalkyl, O-alkyloximino, O-alkenyloximino, O-arylalkyloximino, $C_1$–$C_4$-dialkoxy-$C_1$–$C_4$-alkyl or formyl, X is hydrogen, halogen, cyano, straight-chain or branched $C_1$–$C_4$-alkyl, $C_1$–$C_4$-haloalkyl or $C_1$–$C_4$-alkoxy and m is an integer of from 1 to 4.

Other preferred compounds are oxime ethers of the formula I, where

G is

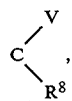

V is

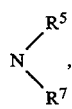

R is $C_3$–$C_8$-cycloalkyl, unsubstituted or substituted $C_2$–$C_8$-alkenyl, unsubstituted or substituted $C_2$–$C_8$-alkynyl, unsubstituted or substituted hetaryl or

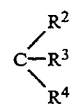

$R^1$ is $C_1$–$C_8$-alkyl, $R^2$ and $R^4$ are each hydrogen, $C_1$–$C_8$-alkyl or $C_3$–$C_8$-cycloalkyl or are each phenyl which is unsubstituted or substituted by $C_1$–$C_4$-alkyl, $C_1$–$C_4$-alkoxy or halogen, $R^3$ is hydrogen, methyl, cyano or —COO—A—, A is hydrogen, methyl, ethyl, isopropyl, propyl, n-butyl, sec-butyl or tert-butyl or, where $R^3$ is —COO—$C_1$–$C_8$-alkyl, $R^2$ and $R^3$ together with the carbon atom of which they are substituents form a 5-membered to 8-membered lactone ring, or $R^2$ and $R^4$ together with the carbon atom of which they are substituents form a $C_3$–$C_8$-cycloalkyl ring, $R^5$ is hydrogen, $C_1$–$C_8$-alkyl, $C_1$–$C_4$-arylalkyl, $C_3$–$C_6$-cycloalkyl, hydroxyl, $C_1$–$C_4$-alkoxy, $NH_2$, $C_1$–$C_4$-alkylamino or $C_1$–$C_4$-dialkylamino, $R^7$ is hydrogen, $C_1$–$C_8$-alkyl or $C_1$–$C_4$-alkanoyl, $R^8$ is hydrogen or $C_1$–$C_8$-alkyl, Y is methylene, ethylene, ethenylene, ethynylene, methyleneoxy, ethyleneoxy, oxymethylene, thiomethylene, carbonyloxy, carbonyloxymethylene, aminocarbonyloxy, methylenethio, oxycarbonylmethylene, oxyethylene, ethylenethio, thioethylene, —C=N—O—$CH_2$—, —O—N=C—, —C=N—O—, —N=N— or O or S, Z is straight-chain or branched $C_1$–$C_{10}$-alkyl, $C_2$–$C_{10}$-alkenyl, $C_2$–$C_{10}$-alkynyl, phenyl, pyridyl, pyridazinyl, pyrimidinyl, pyrazinyl, quinolyl, isoquinolyl, naphthyridyl, quinoxalyl, thienyl, furyl, pyrrolyl, oxazolyl, isoxazolyl, pyrazolyl, imidazolyl, thiazolyl, isothiazolyl, benzothiazolyl, benzoisothiazolyl, benzoxazolyl, benzoisoxazolyl, benzopyrrazolyl, benzoimidazolyl, indolyl, isoindolyl, benzothiophenyl, isobenzothiophenyl, benzofuranyl, isobenzofuranyl or, only when Y is not oxymethylene, oxyethylene, oxycarbonyl, oxycarbonylmethylene, thiomethylene, thioethylene, —O—N=C—, —N=N—, O or S, straight-chain or branched $C_1$–$C_{10}$-alkoxy, $C_1$–$C_{10}$-alkenyloxy, phenyloxy, pyridyloxy, pyridazinyloxy, pyrimidinyloxy, pyrazinyloxy, quinolyloxy, isoquinolyloxy, naphthyridyloxy, quinoxalyloxy, thienyloxy, furyloxy, pyrrolyloxy, oxazolyloxy, isoxazolyloxy, pyrazolyloxy, imidazolyloxy, thiazolyloxy, isothiazolyloxy, benzothiazolyloxy, benzoisothiazolyloxy, benzoxazolyloxy, benzoisoxazolyloxy, benzopyrazolyloxy, benzoimidazolyloxy, indolyloxy, isoindolyloxy, benzothiophenoxy, isobenzothiophenoxy, benzofuranyloxy, isobenzofuranyloxy or, only when Y is not oxymethylene, oxyethylene, oxycarbonyl, oxycarbonylmethylene, —O—N=C—, —N=N— or O, straight-chain or branched $C_1$–$C_{10}$-alkylthio, $C_2$–$C_{10}$-alkenylthio, phenylthio, pyridylthio, pyridazinylthio, pyrimidinylthio, pyrazinylthio, quinolylthio, isoquinolylthio, naphthyridylthio, quinoxalylthio, thienylthio, furylthio, pyrrolylthio, oxazolylthio, isoxazolylthio, pyrazolylthio, imidazolylthio, thiazolylthio, isothiazolylthio, benzothiazolylthio, benzoisothiazolylthio, benzoxazolylthio, benzoisoxazolylthio, benzopyrazolylthio, benzoimidazolylthio, indolylthio, isoindolylthio, benzothiophenylthio, isobenzothiophenylthio, benzofuranylthio or isobenzofuranylthio, which are unsubstituted or substituted by halogen, cyano, straight-chain or branched $C_1$–$C_4$-alkyl, $C_2$–$C_4$-alkenyl, $C_2$–$C_4$-alkynyl, hydroximino, $C_1$–$C_4$-carboxyalkoxy, $C_1$–$C_4$-alkanoyl, $C_1$–$C_4$-alkoxyalkyl, $C_1$-$C_4$-dialkoxyalkyl, O-alkyloximino, O-alkenyloximino, O-arylalkyloximino, $C_1$-$C_4$-dialkoxy-$C_1$-$C_4$-alkyl or formyl, X is hydrogen, halogen, cyano, straight-chain or branched $C_1$-$C_4$-alkyl, $C_1$-$C_4$-haloalkyl or $C_1$-$C_4$-alkoxy and m is an integer of from 1 to 4.

The compounds of the formula Ib and Ic can be prepared by reacting an O-alkyl oxime of a methyl phenylglyoxylate (European Patent 253,213) of the formula II

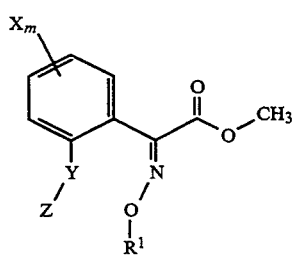

where $R^1$, Y, Z, X and m have the abovementioned meanings, with a compound of the formula III

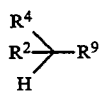

where $R^2$ and $R^4$ have the abovementioned meanings and $R^9$ is —CN or —COO—A and A has the abovementioned meanings, under basic conditions (E. V. P. Tao and G. S. Staten, *Org. Prep. Proc. Int. Briefs* 17 (1985), 235).

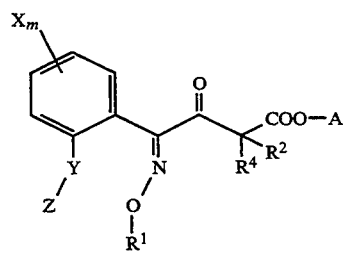

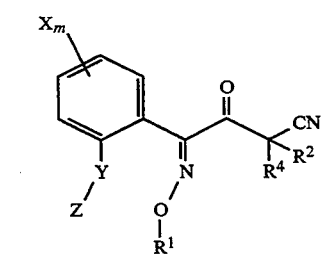

The compounds Ib can be further converted into compounds of type Ia (S. Takei and Y. Kawano, *Tetrahedron Lett.* 49 (1975), 4389).

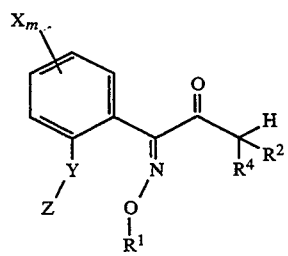

Starting from compounds of the formula II, the compounds of the formula Id can be obtained by another method. The compounds of the formula IV can readily be prepared in a known manner (S. Nahm and S. M. Weinreb, *Tetrahedron Lett.* 39 (1981), 3815).

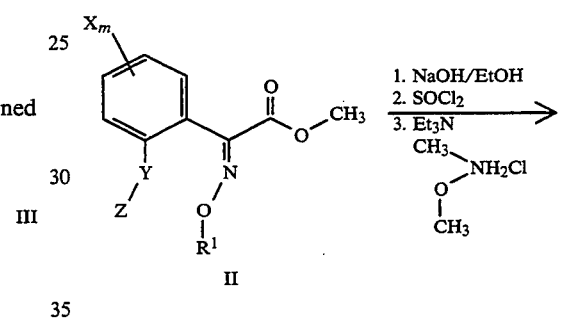

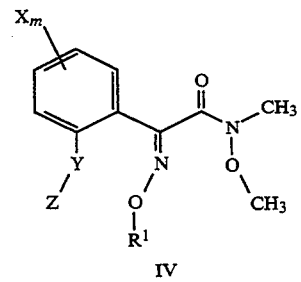

The further reaction of the amides IV with organolithium reagents (S. Nahm and S. M. Weinreb, *Tetrahedron Lett.* 39 (1981), 3815) gives the desired α-oximinoketones of the formula Id.

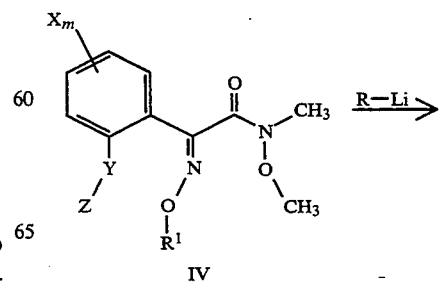

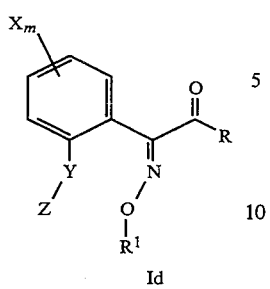

Id

It is also known that compounds of type Id react with amines, hydroxylamines and hydrazines and give compounds of type Ie (Advanced Organic Chemistry, J. March, Third Edition, pages 804–805).

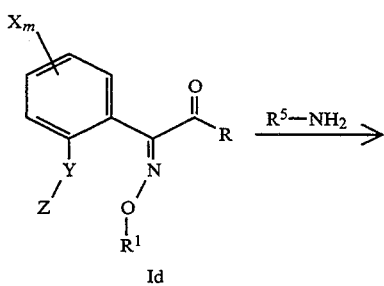

Id

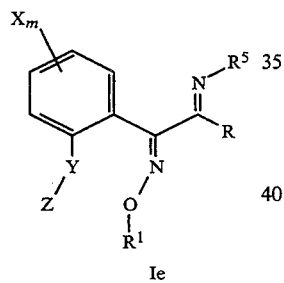

Ie

It is also known that imines, oximes and hydrazones of type Ie and ketones of type Id can be reduced by various reducing agents (Advanced Organic Chemistry, J. March, Third Edition, pages 694/814–815). When ketones Id are used, the reaction gives the corresponding alcohols If, and the corresponding amines, hydroxylamines and hydrazines Ig are formed when imines, oximes or hydrazones of type Ie are used.

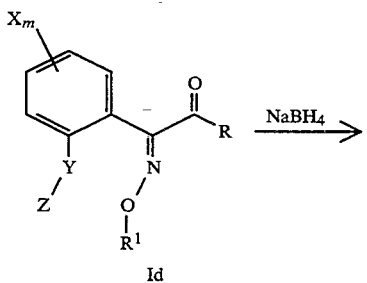

Id

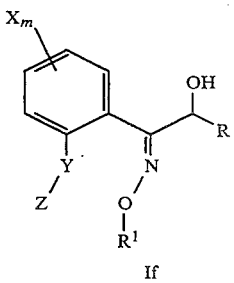

If

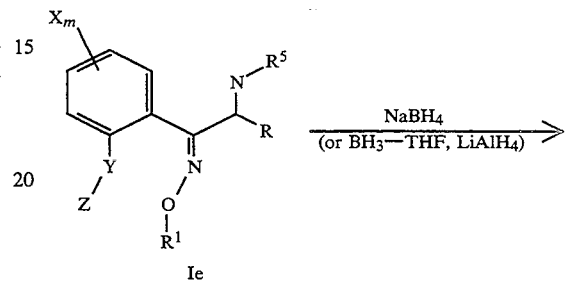

Ie

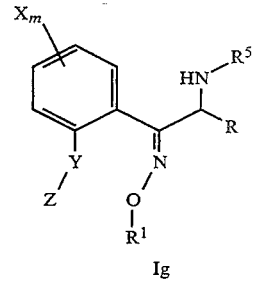

Ig

The compounds If and Ig can furthermore be alkylated or acylated in a known manner (Advanced Organic Chemistry, J. March, Third Edition, pages 342, 343 and 347, and Organikum, Fifteenth Edition, page 257, and Houben-Weyl, Methoden der organischen Chemie, Vol. IV/3, pages 295–324, H. Meerwein 1965) and give the compounds Ih and Ii.

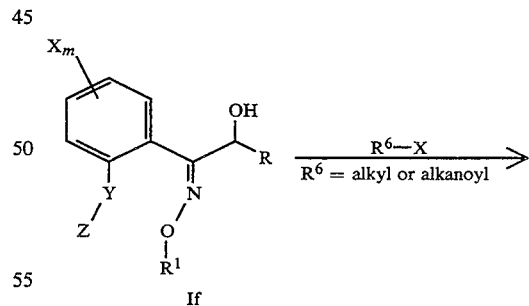

If

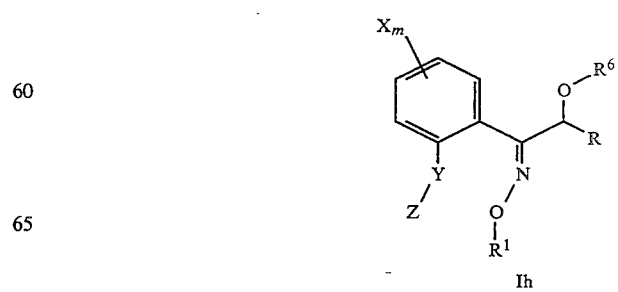

Ih

-continued

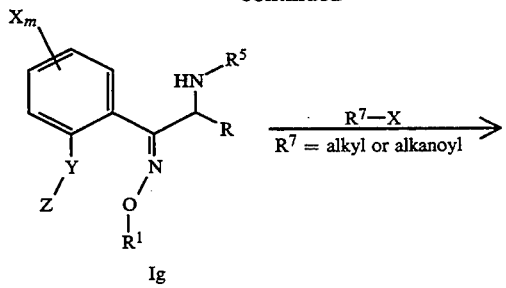

$R^7-X$ →
$R^7$ = alkyl or alkanoyl

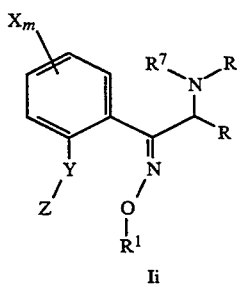

The Examples and methods which follow illustrate the preparation of the novel compounds and of the intermediates.

Preparation Examples

EXAMPLE 1

1-Methoximino-1-[2'-(2-methylphenoxymethyl)-phenyl]-3-cyanopropan-2-one (compound No. 2)

1.74 g of 50% strength NaH in 50 ml of cyclohexane are initially taken, 10 g (0.032 mol) of methyl 1-methoximino-1-[2'-(2-methylphenoxymethyl)]-phenylacetate in 40 ml of 1:1 cyclohexane/acetonitrile are added dropwise while refluxing, the mixture is boiled for a further 6 hours and is cooled. The organic phase is extracted with 100 ml of water, and the aqueous solution is acidified with hydrochloric acid and extracted with toluene. Drying and evaporation give 8.7 g (84%) of product No. 2 of melting point 65° C.

EXAMPLE 2

1-Methoximino-1-[2'-(2-methylphenoxymethyl)-phenyl]-3-carbomethoxybutan-2-one (compound No. 83)

10.5 g of 50% strength NaH in 150 ml of cyclohexane are initially taken, 60 g (0.032 mol) of methyl 1-methoximino-1-[2'-(2-methylphenoxymethyl)]-phenylacetate and 84 g (0.95 mol) of methyl propionate in 150 ml of cyclohexane are added dropwise while refluxing, and the mixture is boiled for a further 6 hours and is cooled. The organic phase is washed with 200 ml of water, the aqueous solution is acidified with hydrochloric acid and reextracted with cyclohexane, and the total organic phases are dried and evaporated down. 55 g (78%) of product No. 83 are obtained. IR (cm$^{-1}$): 1747, 1699, 1495, 1241, 1033)

EXAMPLE 3

1-Methoximino-1-[2'-(2-methylphenoxymethyl)-phenyl]-butan-2-one (compound No. 300)

50 g (0.135 mol) of compound No. 83 are dissolved in 500 ml of ethanol and 150 ml of water, the solution is refluxed, 50 ml of concentrated H$_2$SO$_4$ are slowly added and the mixture is boiled for a further 9 hours. After the mixture has been cooled, water is added, the mixture is neutralized by adding sodium hydroxide solution and extracted with methyl tert-butyl ether, and the organic phase is dried and evaporated down. The crude product is purified by column chromatography (9:1 cyclohexane/ethyl acetate) and gives 25.7 g (61%) of product No. 300. IR (cm$^{-1}$): 2938, 1695, 1495, 1241, 1033)

EXAMPLE. 4

1-Methoximino-1-[2'-(2-methylphenoxymethyl)-phenyl]-3-methylbutan-2-one (compound No. 380 )

0.9 g of LiCl and 0.16 g of water are added to 1.7 g (4.4 mmol) of 1-methoximino-1-[2'-(2-methylphenoxymethyl)-phenyl]-3-methyl-3-carbomethoxybutan-2-one in 15 ml of dimethyl sulfoxide and the mixture is heated to 140° C. After 20 hours, the reaction mixture is cooled, water is added, the mixture is extracted with methyl tert-butyl ether and the ether phase is washed three times with water, dried and evaporated down. 1.0 g (70%) of product No. 380 is obtained. $^1$H-NMR (CDCl$_3$): 7.60–6.70 (m, 8H); 4.85 (s, 2H); 4.05 (s, 3H); 3.70 (m, 1H); 2.25 (s, 3H); 1.15 (d, 6H)

EXAMPLE 5

1-Methoximino-1-(2'-methylphenyl)-3-carbomethoxy-3-methylbutan-2-one (compound No. 127)

37.5 g (0.143 mol) of 1-methoximino-1-(2'-methylphenyl)-3-carbomethoxybutan-2-one are dissolved in 100 ml of dimethylformamide together with 59 g of K$_2$CO$_3$ and 61 g of CH$_3$I, and the solution is stirred for 48 hours at room temperature. The K$_2$CO$_3$ is filtered off under suction and washed with dimethylformamide, water is added to the dimethylformamide solution, the aqueous solution is extracted with methyl tert-butyl ether and the organic phase is washed with water, dried and evaporated down. 34.3 g (90%) of product No. 127 are obtained. $^1$H-NMR (CDCl$_3$): 7.35–6.90 (m, 4H); 3.95 (s, 3H); 3.75 (s, 3H); 2.10 (s, 3H); 1.55 (s, 6H)

Method 1

1-Methoximino-1-(2,'-bromomethylphenyl)-3-carbomethoxy-3-methylbutan-2-one (compound No. 128)

15.4 g (0.058 mol) of compound No. 127, 12.4 g of N-bromosuccinimide and 0.1 g of benzoyl peroxide are dissolved in 150 ml of cyclohexane, the solution is refluxed for 4 hours and cooled, the succinimide is filtered off under suction and the mother liquor is evaporated down. Column chromatography (4:1 cyclohexane/ethyl acetate) gives 15.4 g (78%) of product No. 128. $^1$H-NMR (CDCl$_3$): 7.55–6.95 (m, 4H); 4.30 (s, 2H); 4.00 (s, 3H); 3.75 (s, 3H); 1.55 (s, 6H)

EXAMPLE 6

1-Methoximino-1-[2'-(4-acetylphenoxymethyl)-phenyl]-3-carbomethoxy-3-methylbutan-2-one (compound No. 129)

15 g (0.42 mol) of compound No. 128 and 7 g of KI are dissolved in 150 ml of dimethylformamide, 7.3 g of the potassium salt of 4-hydroxyacetophenone in 70 ml of dimethylformamide are added and the mixture is stirred overnight at room temperature. Water is then added, the aqueous solution is extracted with ether, and the organic phase is washed with sodium hydroxide solution and water, dried and evaporated down. 15.5 g (90%) of compound No. 129 are obtained. $^1$H-NMR (CDCl$_3$): 7.95–6.85 (m, 8H); 4.90 (s, 2H); 3.95 (s, 3H); 3.65 (s, 3H); 2.55 (s,3H); 1.50 (s, 6H)

Method 2

1-Methoximino-1-(2'-methylphenyl)-acetic acid 120 g (0.58 mol) of methyl 1-methoximino-1-(2'-methylphenyl)-acetate and 730 g of 1M aqueous KOH solution are initially taken and refluxed for 30 minutes, the mixture is cooled and is acidified to pH 1 with concentrated HCl and the product is filtered off under suction, washed with water and dried. 110 g (99%) of the desired product are obtained. $^1$H-NMR (CDCl$_3$): 7.40–7.05 (m, 4H); 5.60 (m, 1H); 4.05 (s, 3H); 2.20 (s, 3H)

Method 3

N-Methoxy-N-methyl-1-methoximino-1-(2'-methylphenyl)-acetamide 23.5 g (0.122 mol) of 1-methoximino-1-(2'-methylphenyl)-acetic acid in 22 g of SOCl$_2$ are heated for 2 hours and cooled, and excess SOCl$_2$ is stripped off. The crude acyl chloride is dissolved with 11.2 g of methyl-methoxyamine hydrochloride in 150 ml of CH$_2$Cl$_2$, 23.1 g of triethylamine are slowly added dropwise at 5° C. and the reaction mixture is stirred for a further 24 hours at room temperature. The triethylamine hydrochloride is filtered off under suction and washed with CH$_2$Cl$_2$, and the combined filtrates are washed with water, HCl solution and sodium hydroxide solution, dried and evaporated down. 23 g (94%) of the desired product of melting point 30° C. are obtained.

Method 4

N-Methoxy-N-methyl-1-methoximino-1-(2'-bromomethylphenyl)-acetamide 10 g (0.042 tool) of N-methoxy-N-methyl-1-methoximino-1-(2'-methylphenyl)-acetamide, 9.8 g of N-bromosuccinimide and 0.1 g of benzoyl peroxide are dissolved in 100 ml of CCl$_4$ and the solution is exposed to light for 4 hours. After cooling, the succinimide is filtered off under suction and washed with CH$_2$Cl$_2$, and the total organic phase is evaporated down. Column chromatography (7:3 cyclohexane/ethyl acetate) gives 8 g (60%) of the desired product. $^1$H-NMR (CDCl$_3$): 7.65–7.25 (m, 4H); 4.50 (s, 2H); 3.95 (s, 3H); 3.60 (s, 3H); 3.25 (s, 3H)

Method 5

N-Methoxy-N-methyl-1-methoximino-1-[2'-(2-methyl-4chlorophenoxymethyl)]-phenylacetamide 2.6 g (0.008 mol) of N-methoxy-N-methyl-1-methoximino-1-(2'-bromomethylphenyl)-acetamide and 1.4 g of KI are dissolved in 40 ml of EtOH, 1.5 g of the potassium salt of 4-chloro-2-methylphenol in 20 ml of EtOH are added and the mixture is stirred overnight at room temperature. Thereafter, water is added, the aqueous solution is extracted with methyl tert-butyl ether and the organic phase is washed with sodium hydroxide solution and water, dried and evaporated down. Column chromatography (4:1 cyclohexane/ethyl acetate) gives 1.2 g (39%) of the desired product. $^1$H-NMR (CDCl$_3$): 7.65–6.70 (m, 7H); 5.05 (s, 2H); 3.95 (s, 3H); 3.55 (s, 3H); 3.25 (s, 3H); 2.30 (s, 3H)

EXAMPLE 7

1-Methoximino-1-[2'-(2-methylphenoxymethyl)-phenyl]-pent-3-yn-2-one (compound No. 1134)

5 g (0.015 mol) of N-methoxy-N-methyl-1-methoximino-1-[2'-(2-methylphenoxymethyl)]-phenylacetamide are dissolved in 50 ml of absolute tetrahydrofuran under a nitrogen atmosphere, 18 ml of a 1M propynyllithium solution in solvent are slowly added dropwise at 0° C., the mixture is stirred for a further 30 minutes at 0° C., a 1M NH$_4$Cl solution is added, the mixture is extracted with methyl tert-butyl ether and the organic phase is dried and evaporated down. 4.5 g (93%) of compound No. 1134 are obtained. $^1$H-NMR (CDCl$_3$): 7.60–6.70 (m, 8H); 4.90 (s, 2H); 4.10 (s, 3H); 2.25 (s, 3H); 2.10 (s, 3H)

Method 6

1-Methoximino-1-(2'-bromomethylphenyl)-butan-2-one (compound No. 317)

10 g (0.049 mol) of 1-methoximino-1-(2'-methylphenyl)-butan-2-one, 11.3 g of N-bromosuccinimide and 0.1 g of benzoyl peroxide are dissolved in 100 ml of CCl$_4$ and the solution is exposed to light for 4 hours. After cooling, the succinimide is filtered off under suction and washed with CH$_2$Cl$_2$, and the total organic phase is evaporated down. 13.2 g (91%) of compound No. 317 are obtained. IR (cm$^{-1}$): 2975, 2937, 1697, 1032, 761

EXAMPLE 8

1-Methoximino-1-[2'-(2-methylcarboxyphenyl)-phenyl]-butan-2-one (compound No. 310)

2 g (0.007 mol) of compound No. . . . are mixed with 1.9 g of o-methylbenzoic acid, 1.9 g of K$_2$CO$_3$ and 0.1 g of KI in 50 ml of acetone and the mixture is stirred for 72 hours at room temperature. Water is added, the aqueous solution is extracted with methyl tert-butyl ether and the organic phase is washed with sodium hydroxide solution, dried and evaporated down. Column chromatography (4:1 cyclohexane/ethyl acetate) gives 0.5 g (20%) of compound No. 310. $^1$H-NMR (CDCl$_3$): 7.85–7.05 (m, 8H); 5.10 (s, 2H); 3.95 (s, 3H); 2.90 (q, 2H); 2.55 (s, 3H); 1.05 (t, 3H)

EXAMPLE 9

1-Methoximino-1-[2'-(2-methylphenoxymethyl)-phenyl]-2-methyliminopropane (compound No. 675)

4 g (0.013 mol) of 1-methoximino-1-[2'-(2-methylphenoxymethyl)-phenyl]-propan-2-one are dissolved in 60 ml of ethanol, 4 g of Na$_2$SO$_4$ are added, the mixture is cooled at −40° C., 13 g of methylamine are passed in over 20 minutes, the cooling means are removed and the mixture is stirred for 72 hours at room temperature. The sodium sulfate is filtered off under suction, the ethanol is evaporated, the residue is dissolved in methyl tert-butyl ether and the organic phase is washed three times with water, dried and evaporated down. 3.2 g (80%) of compound No. 675 of melting point 102°–104° C. are obtained.

EXAMPLE 10

1-Methoximino-1-[2'-(2-methylphenoxymethyl)-phenyl]-propan-2-ol (compound No. 891)

5 g (17 mmol) of 1-methoximino-1-[2'-(2-methylphenoxymethyl)-phenyl]-propan-2-one are dissolved in ethanol, and 0.7 g of NaBH₄ is added at room temperature. The mixture is further stirred overnight at room temperature, the solvent is evaporated, the residue is taken up in tert-butyl methyl ether and the solution is washed three times with water, dried and evaporated down. The crude product is purified by column chromatography (5:5 cyclohexane/ethyl acetate) and gives 3.8 g (76%) of compound No. 891. ¹H-NMR (CDCl₃): 7.70–6.75 (m, 8H); 4.95 (m, 2H); 4.65 (m, 1H); 3.85 (s, 3H); 2.95 (m, 1H); 2.25 (s, 3H); 1.35 (d, 3H).

EXAMPLE 11

2-Methoxy-1-methoximino-1-[2'-(2-methylphenoxymethyl)-phenyl]-propane (compound No. 946)

0.27 g (5.5 mmol) of 50% strength NaH is washed with pentane and initially taken in 10 ml of tetrahydrofuran together with 0.7 g of dimethyl sulfate. A solution of 1.5 g (5 mmol) of product (16) in 10 ml of tetrahydrofuran is added dropwise at room temperature and the mixture is stirred for a further 3 hours. Water and diethyl ether are added, and the organic phase is washed with sodium hydroxide solution, dried and evaporated down. 1.6 g (99%) of compound No. 946 are obtained. ¹H-NMR (CDCl₃): 7.70–6.75 (m, 8H); 4.95 (m, 2H); 4.15 (m, 1H); 3.90 (s, 3H); 3.45 (s, 3H); 2.30 (s, 3H); 1.20 (d, 3H).

The compounds listed in the Table below are prepared in a similar manner.

TABLE 1

Ph = Phenyl

Structure for Nos. 1–12: 2-(CH₂OZ)-phenyl-C(=NOCH₃)-C(=O)-CH₂CN

Structure for Nos. 13–18: 2-(CH₂-O-CO-Z)-phenyl-C(=NOCH₃)-C(=O)-CH₂CN

| No. | Y | Z | m.p. [°C] or IR(cm⁻¹) |
|---|---|---|---|
| 1 |   | —Ph | 72–74 |
| 2 |   | -(2-Me)Ph |   |
| 3 |   | -(2,4-DiMe)Ph |   |
| 4 |   | -(4-Cl, 2-Me)Ph |   |
| 5 |   | -(4-Cl)Ph |   |
| 6 |   | -(4-tBu, 2 Me)Ph |   |
| 7 |   | -(2,3,5-TriMe)Ph |   |
| 8 |   | -(4-Cyclohexyl, 2-Me)Ph |   |
| 9 |   | -(4-Phenyl)Ph |   |
| 10 |   | -(5-Me, 2-iPr)Ph |   |
| 11 |   | -(2,5-DiMe)Ph |   |
| 12 |   | -(2,5-DiEt)Ph |   |
| 13 |   | -(2-Me)Ph |   |
| 14 |   | -[1-(4-ClPhenyl)]cyclopropyl |   |
| 15 |   | -[1-(3,4-DiClPhenyl)]cyclopropyl |   |
| 16 |   | -[1-(4-Methoxyphenyl)]cyclopropyl |   |
| 17 |   | -(1-Methyl)cyclopropyl |   |
| 18 |   | -[2,2-DiMethyl, 3-(2,2′-dibromoethylene]cyclopropyl |   |

TABLE 1-continued

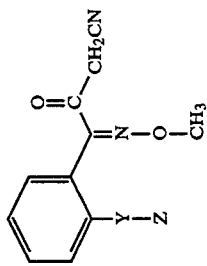
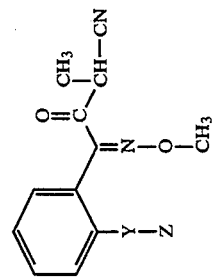

| | | | m.p. |
|---|---|---|---|
| 19 | —CH$_2$— | —H | |
| 20 | —CH$_2$O— | —Br | |
| 21 | — | -4-(1-oxo)Ethyl-Ph | |
| 22 | — | -4[1-(2-propenoxyimino)]Ethyl-Ph | |
| 23 | — | -4(1-Ethyloxyimino)Ethyl-Ph | |
| 24 | — | -4(1-Benzyloxyimino)Ethyl-Ph | |
| 25 | — | -4(2-propenoxyimino)Methyl-Ph | |
| 26 | — | -4(Ethyloxyimino)Methyl-Ph | |
| 27 | — | -4(Benzyloxyimino)Methyl-Ph | |
| 28 | —CH$_2$O— | —Ph | |
| 29 | — | -(2-Me)Ph | |
| 30 | — | -(2,4-DiMe)Ph | |
| 31 | — | -(4-Cl, 2-Me)Ph | |
| 32 | — | -(4-Cl)Ph | |
| 33 | — | -(4-tBu, 2-Me)Ph | |
| 34 | — | -(2,3,5-TriMe)Ph | |
| 35 | — | -(4-Cyclohexyl, 2-Me)Ph | |
| 36 | — | -(4-Phenyl)Ph | |
| 37 | — | -(5-Me, 2-iPr)Ph | |
| 38 | — | -(2,5-DiMe)Ph | |
| 39 | — | -(2,5-DiEt)Ph | |
| 40 | —CH$_2$—O—C(=O)— | -(2-Me)Ph | 92-93 |
| 41 | — | -[1-(4-ClPhenyl)]cyclopropyl | |
| 42 | — | -[1-(3,4-DiClPhenyl)]cyclopropyl | |
| 43 | — | -[1-(4-Methoxyphenyl)]cyclopropyl | |
| 44 | — | -(1-Methyl)cyclopropyl | |

TABLE 1-continued $$\text{structure: 2-substituted phenyl with } -C(=N-OCH_3)-C(=O)-CH_2-COOCH_3 \text{ group, and } -Y-Z \text{ at ortho position}$$

| No. | Y | Z | Ar substituent | IR |
|---|---|---|---|---|
| 45 | — | — | -[2,2-DiMethyl1,3-(2,2'-dibromoethylene)cyclopropyl] | |
| 46 | —CH₂ | — | —H | |
| 47 | —CH₂O | — | —Br | |
| 48 | — | — | 4-(1-oxo)Ethyl-Ph | |
| 49 | — | — | 4-[1-(2-propenoxyimino)]Ethyl-Ph | |
| 50 | — | — | 4[1-Ethyloxyimino)Ethyl-Ph | |
| 51 | — | — | 4(1-Benzyloxyimino)Ethyl-Ph | |
| 52 | — | — | 4(2-propenoxyimino)Methyl-Ph | |
| 53 | — | — | 4(Ethyloxyimino)Methyl-Ph | |
| 54 | — | — | 4(Benzyloxyimino)Methyl-Ph | |
| 55 | —CH₂O | — | —Ph | |
| 56 | — | — | -(2-Me)Ph | |
| 57 | — | — | -(2,4-DiMe)Ph | |
| 58 | — | — | -(4-Cl, 2-Me)Ph | |
| 59 | — | — | -(4-Cl)Ph | |
| 60 | — | — | -(4-tBu, 2 Me)Ph | |
| 61 | — | — | -(2,3,5-TriMe)Ph | |
| 62 | — | — | -(4-Cyclohexyl, 2-Me)Ph | |
| 63 | — | — | -(4-Phenyl)Ph | |
| 64 | — | — | -(5-Me, 2-iPr)Ph | |
| 65 | — | — | -(2,5-DiMe)Ph | IR: 1745, 1699, 1495, 1242, 1043 |
| 65 | — | — | -(2,5-DiMe)Ph | |
| 66 | — | — | -(2,5-DiEt)Ph | |
| 67 | —CH₂—O—C(=O) | | -(2-Me)Ph | IR: 1745, 1699, 1255, 1129, 1043 |
| 68 | — | — | -[1-(4-ClPhenyl)]cyclopropyl | |
| 69 | — | — | -[1-(3,4-DiClPhenyl)]cyclopropyl | |
| 70 | — | — | -[1-(4-Methoxyphenyl)]cyclopropyl | |
| 71 | — | — | -(1-Methyl)cyclopropyl | |
| 72 | — | — | -[2,2-Dimethyl,3-(2,2'-Dibromoethylene)cyclopropyl] | |
| 73 | —CH₂ | — | —H | |
| 74 | —CH₂O | — | —Br | |
| 75 | — | — | 4-(1-oxo)Ethyl-Ph | |
| 76 | — | — | 4[1-(2-propenoxyimino)]Ethyl-Ph | |
| 77 | — | — | 4(1-Ethyloxyimino)Ethyl-Ph | |
| 78 | — | — | 4(1-Benzyloxyimino)Ethyl-Ph | |
| 79 | — | — | 4(2-propenoxyimino)Methyl-Ph | |
| 80 | — | — | 4(Benzyloxyimino)Methyl-Ph | |

TABLE 1-continued

| # | | | |
|---|---|---|---|
| 81 | — | -4(Benzyloxyimino)Methyl-Ph | |
| 1.82 | —CH$_2$O— | -2-Methyl-4-(1-oxo)ethyl-Phenyl | |
| 1.83 | —CH$_2$O— | -2-Methyl-4-(1-methoxyimino)ethyl-Phenyl | |
| 1.84 | —CH$_2$O— | -2-Methyl-4-(1-ethoxyimino)ethyl-Phenyl | |
| 1.85 | —CH$_2$O— | -2-Methyl-4-(1-n-propyloxyimino)ethyl-Phenyl | |
| 1.86 | —CH$_2$O— | -2-Methyl-4-(1-isopropyloxyimino)ethyl-Phenyl | |
| 1.87 | —CH$_2$O— | -2-Methyl-4-(1-n-butyloxyimino)ethyl-Phenyl | |
| 1.88 | —CH$_2$O— | -2-Methyl-4-(1-isobutyloxyimino)ethyl-Phenyl | |
| 1.89 | —CH$_2$O— | -2-Methyl-4-[1-(2-propenoxyimino)]ethyl-Phenyl | |
| 1.90 | —CH$_2$O— | -2-Methyl-4-[1-(3-chloro-E-2-propenoxyimino)]ethyl-Phenyl | |
| 1.91 | —CH$_2$O— | -2-Methyl-4-(1-benzyloxyimino)ethyl-Phenyl | |
| 1.92 | —CH$_2$O— | -2-Methyl-4-(1-oxo)propyl-Phenyl | |
| 1.93 | —CH$_2$O— | -2-Methyl-4-(1-methoxyimino)propyl-Phenyl | |
| 1.94 | —CH$_2$O— | -2-Methyl-4-(1-ethoxyimino)propyl-Phenyl | |
| 1.95 | —CH$_2$O— | -2-Methyl-4-(1-n-propyloxyimino)propyl-Phenyl | |
| 1.96 | —CH$_2$O— | -2-Methyl-4-(1-iso-propyloxyimino)propyl-Phenyl | |
| 1.97 | —CH$_2$O— | -2-Methyl-4-[1-(2-propenoxyimino)]propyl-Phenyl | |
| 1.98 | —CH$_2$O— | -2-Methyl-4-[3-chloro-E-2-propenoxyimino)]propyl-Phenyl | |
| 1.99 | —CH$_2$O— | -2-Methyl-4-(1-benzyloxyimino)propyl-Phenyl | |
| 1.100 | —CH$_2$O— | -2,5-Dimethyl-4-(1-oxo)ethyl-Phenyl | |
| 1.101 | —CH$_2$O— | -2,5-Dimethyl-4-(1-methoxyimino)ethyl-Phenyl | |
| 1.102 | —CH$_2$O— | -2,5-Dimethyl-4-(1-ethoxyimino)ethyl-Phenyl | |
| 1.103 | —CH$_2$O— | -2,5-Dimethyl-4-(1-n-propyloxyimino)ethyl-Phenyl | |
| 1.104 | —CH$_2$O— | -4,5-Dimethyl-4-(1-iso-propyloxyimino)ethyl-Phenyl | |
| 1.105 | —CH$_2$O— | -2,5-Dimethyl-4-[1-(2-propenoxyimino)]ethyl-Phenyl | |
| 1.106 | —CH$_2$O— | -2,5-Dimethyl-4-[1-(3-chloro-E-2-propenoxyimino)]ethyl-Phenyl | |
| 1.107 | —CH$_2$O— | -2,5-Dimethyl-4-(1-benzyloxyimino)ethyl-Phenyl | |
| 1.108 | —CH$_2$—O—N=C— CH$_3$ | -3,5-Dichlorophenyl | IR: 1745, 1327, 1246, 1149, 1042 |
| 1.109 | —CH$_2$—O—N=C— CH$_3$ | -4-Trifluoromethyl-phenyl | |
| 1.110 | —CH$_2$—O—N=C— CH$_3$ | -3-Trifluoromethyl-phenyl | |
| 1.111 | —CH$_2$—O—N=C— CH$_3$ | -4-Bromophenyl | |
| 1.112 | —CH$_2$—O—N=C— CH$_3$ | -4-tert-Butyl-phenyl | |
| 1.113 | —CH$_2$—O—N=C— CH$_3$ | -2,4-Dimethyl-phenyl | |

TABLE 1-continued
| No. | | |
|---|---|---|
| 1.114 | —CH₂—O—N=C(—)CH₃ | -3,4-Dichlor-phenyl |
| 1.115 | —CH₂—O—N=C(—)CH₃ | -2-Methyl-phenyl |
| 1.116 | —CH₂—O—N=C(—)CH₃ | -4-Nitro-phenyl |
| 1.117 | —CH₂—O—N=C(—)CH₃ | -4-Methyl-phenyl |
| 1.118 | —CH₂—O—N=C(—)CH₃ | -2-Pyrazinyl |
| 1.119 | —CH₂—O—N=C(—)CH₃ | -4-Pyrimidinyl |
| 1.120 | —CH₂—O—N=C(—)CH₃ | -3-Pyridinyl |
| 1.121 | —CH₂—O—N=C(—)CH₃ | -2-Furyl |
| 1.122 | —CH₂—O—N=C(—)CH₃ | -2-Thienyl |
| 1.123 | —O— | -Phenyl |
| 1.124 | —O— | -3-Methoxy-phenyl |
| 1.125 | 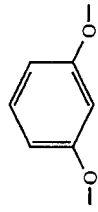 | -Phenyl |
| 1.126 | 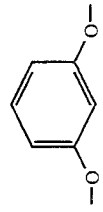 | -2-Fluorophenyl |

TABLE 1-continued
| | | |
|---|---|---|
| 1.127 | 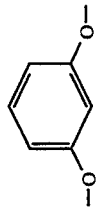 | -2-Chlorophenyl |
| 1.128 | 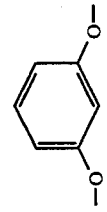 | -2-Cyano-phenyl |
| 1.129 | 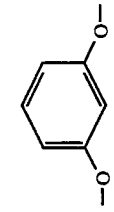 | -2-Methyl-phenyl |
| 1.130 | 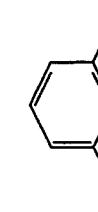 | -2-Nitro-phenyl |
| 1.131 | 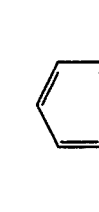 | -2-Trifluoromethyl-phenyl |
| 1.132<br>1.133<br>1.134<br>1.135 | 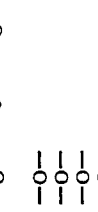<br>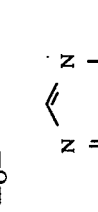<br>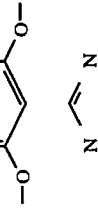<br>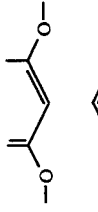 | -4-Methylpyridin-2-yl<br>-4-Trifluoropyridin-2-yl<br>-5-Chloropyridin-2-yl<br>-4-Chloroprimidin-2-yl |
| 1.136 | 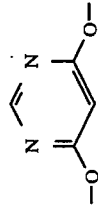 | -Phenyl |
| 1.137 | 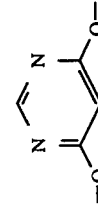 | -2-Fluorophenyl |
| 1.138 | 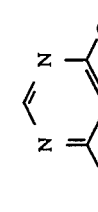 | -2-Chlorophenyl |

TABLE 1-continued

| | Structure | Substituent |
|---|---|---|
| 1.139 | pyrimidine-4,6-diyloxy | -2-Bromophenyl |
| 1.140 | pyrimidine-4,6-diyloxy | -2-Cyanophenyl |
| 1.141 | pyrimidine-4,6-diyloxy | 2-(NH$_2$—C(=S)—)Phenyl |
| 1.142 | pyrimidine-4,6-diyloxy | -2-Nitrophenyl |
| 1.143 | pyrimidine-4,6-diyloxy | -2-Methoxyphenyl |
| 1.144 | pyrimidine-4,6-diyloxy | -2-Methylphenyl |
| 1.145 | pyrimidine-4,6-diyloxy | -2-Trifluoromethyl-phenyl |
| 1.146 | pyrimidine-4,6-diyloxy | -2-Cyano-4-chlorophenyl |
| 1.147 | pyrimidine-4,6-diyloxy | -2,6-Difluorophenyl |

TABLE 1-continued

[Structure: phenyl ring with ortho Y-N substituent, connected to C(=N-O-CH₃) group, which is attached to C(=O)-C(CH₃)(CH-COOCH₃)]

| # | | Y | | IR |
|---|---|---|---|---|
| 1.148 | ![pyrimidine structure with OCH₃ groups] | -Phenyl | | |
| 1.149 | ![pyrimidine structure with OCH₃ groups] | -2-Cyanophenyl | | |
| 82 | —CH₂O— | —Ph | | IR: 1747, 1699, 1495, 1312, 1033 |
| 83 | — | -(2-Me)Ph | | |
| 84 | — | -(2,4-DiMe)Ph | | |
| 85 | — | -(4-Cl, 2-Me)Ph | | |
| 86 | — | -(4-Cl)Ph | | |
| 87 | — | -(4-tBu, 2-Me)Ph | | |
| 88 | — | -(2,3,5-TriMe)Ph | | |
| 89 | — | -(4-Cyclohexyl, 2-Me)Ph | | |
| 90 | — | -(4-Phenyl)Ph | | |
| 91 | — | -(5-Me, 2-iPr)Ph | | |
| 92 | — | -(2,5-DiMe)Ph | | |
| 93 | — | -(2,5-DiEt)Ph | | |
| 94 | —CH₂—O—C(=O)— | -(2-Me)Ph | | |
| 95 | — | -[1-(4-ClPhenyl)]cyclopropyl | | |
| 96 | — | -[1-(3,4-DiClPhenyl)]cyclopropyl | | |
| 97 | — | -[1-(4-Methoxyphenyl)]cyclopropyl | | |
| 98 | —CH₂— | -(1-Methyl)cyclopropyl | | |
| 99 | — | -[2,2-DiMethyl,3-(2,2′-Dibromoethylene)]cyclopropyl | | |
| 100 | —CH₂O— | —H | | |
| 101 | — | —Br | | |
| 102 | — | 4-(1-oxo)Ethyl-Ph | | |
| 103 | — | 4-[1-(2-propenoxyimino)]Ethyl-Ph | | |
| 104 | — | 4-(1-Ethyloxyimino)Ethyl-Ph | | |
| 105 | — | 4-(1-Benzyloxyimino)Ethyl-Ph | | |
| 106 | — | 4-(2-propenoxyimino)Methyl-Ph | | |

TABLE 1-continued

| | | | |
|---|---|---|---|
| 107 | — | -4(Ethyloxyimino)Methyl-Ph | |
| 108 | — | -4(Benzyloxyimino)Methyl-Ph | |
| 1.150 | —CH$_2$O | -2-Methyl-4-(1-oxo)ethyl-Phenyl | |
| 1.151 | —CH$_2$O | -2-Methyl-4-(1-methoxyimino)ethyl-Phenyl | IR: 1747, 1505, 1245, 1050, 1035 cm$^{-1}$ |
| 1.152 | —CH$_2$O | -2-Methyl-4-(1-ethoxyimino)ethyl-Phenyl | IR: 1748, 1505, 1245, 1049, 1036 cm$^{-1}$ |
| 1.153 | —CH$_2$O | -2-Methyl-4-(1-n-propyloxyimino)ethyl-Phenyl | IR: 1505, 1245, 1047, 1036, 1011 cm$^{-1}$ |
| 1.154 | —CH$_2$O | -2-Methyl-4-(1-isopropyloxyimino)ethyl-Phenyl | IR: 1505, 1368, 1244, 1007, 968 cm$^{-1}$ |
| 1.155 | —CH$_2$O | -2-Methyl-4-(1-n-butyloxuimino)ethyl-Phenyl | IR: 1505, 1505, 1318, 1245, 1033 cm$^{-1}$ |
| 1.156 | —CH$_2$O | -2-Methyl-4-(1-isobutyloxyimino)ethyl-Phenyl | IR: 2935, 1506, 1318, 1245, 1040 cm$^{-1}$ |
| 1.157 | —CH$_2$O | -2-Methyl-4-[1-(2-propenoxyimino)]ethyl-Phenyl | IR: 2155, 1505, 1317, 1245, 1034 cm$^{-1}$ |
| 1.158 | —CH$_2$O | -2-Methyl-4-[1-(3-chloro-E-2-propenoxyimino)]ethyl-Phenyl | IR: 1747, 1505, 1318, 1246, 1144, 1035 cm$^{-1}$ |
| 1.159 | —CH$_2$O | -2-Methyl-4-(1-benzyloxyimino)ethyl-Phenyl | |
| 1.160 | —CH$_2$O | -2-Methyl-4-(1-oxo)propyl-Phenyl | |
| 1.161 | —CH$_2$O | -2-Methyl-4-(1-methoxyimino)propyl-Phenyl | |
| 1.162 | —CH$_2$O | -2-Methyl-4-(1-ethoxyimino)propyl-Phenyl | |
| 1.163 | —CH$_2$O | -2-Methyl-4-(1-n-propyloxyimino)propyl-Phenyl | |

| No. | Col2 | Col3 | IR |
|---|---|---|---|
| 1.164 | —CH₂O | -2-Methyl-4-(1-iso-propoxyimino)propyl-Phenyl | |
| 1.165 | —CH₂O | -2-Methyl-4-[1-(2-propenoxyimino)]propyl-Phenyl | |
| 1.166 | —CH₂O | -2-Methyl-4-[3-chloro-E-2-propenoxyimino)]propyl-Phenyl | |
| 1.167 | —CH₂O | -2-Methyl-4-(1-benzyloxyimino)propyl-Phenyl | |
| 1.168 | —CH₂O | -2,5-Dimethyl-4-(1-oxo)ethyl-Phenyl | |
| 1.169 | —CH₂O | -2,5-Dimethyl-4-(1-methoxyimino)ethyl-Phenyl | IR: 1748, 1327, 1246, 1147, 1044 cm⁻¹ |
| 1.170 | —CH₂O | -2,5-Dimethyl-4-(1-ethoxyimino)ethyl-Phenyl | IR: 1748, 1326, 1150, 1046, 1037 cm⁻¹ |
| 1.171 | —CH₂O | -2,5-Dimethyl-4-(1-n-propyloxyimino)ethyl-Phenyl | IR: 1748, 1326, 1245, 1147, 1036 cm⁻¹ |
| 1.172 | —CH₂O | -2,5-Dimethyl-4-(1-iso-propyloxyimino)ethyl-Phenyl | IR: 1322, 1246, 1156, 1140, 1035 cm⁻¹ |
| 1.173 | —CH₂O | -4,5-Dimethyl-4-[1-(2-propenoxyimino)]ethyl-Phenyl | IR: 1748, 1326, 1245, 1150, 1035 cm⁻¹ |
| 1.174 | —CH₂O | -2,5-Dimethyl-4-[1-(3-chloro-E-2-propenoxyimino)]ethyl-Phenyl | IR: 1747, 1326, 1246, 1150, 1036 cm⁻¹ |
| 1.175 | —CH₂O | -2,5-Dimethyl-4-[1-benzyloxyimino)ethyl-Phenyl | IR: 1747, 1326, 1247, 1150, 1035 cm⁻¹ |
| 1.176 | —CH₂—O—N=C(CH₃)— | -3,5-Dichlorophenyl | |
| 1.177 | —CH₂—O—N=C(CH₃)— | -4-Trifluoromethyl-phenyl | |
| 1.178 | —CH₂—O—N=C(CH₃)— | -3-Trifluoromethyl-phenyl | |
| 1.179 | —CH₂—O—N=C(CH₃)— | -4-Bromophenyl | |
| 1.180 | —CH₂—O—N=C(CH₃)— | -4-tert-Butyl-phenyl | |
| 1.181 | —CH₂—O—N=C(CH₃)— | -2,4-Dimethyl-phenyl | |
| 1.182 | —CH₂—O—N=C(CH₃)— | -3,4-Dichlorophenyl | |
| 1.183 | —CH₂—O—N=C(CH₃)— | -2-Methyl-phenyl | |
| 1.184 | —CH₂—O—N=C(CH₃)— | -4-Nitro-phenyl | |
| 1.185 | —CH₂—O—N=C(CH₃)— | -4-Methyl-phenyl | |

-continued

| | | | |
|---|---|---|---|
| 1.186 | —CH₂—O—N=C(CH₃)— | -2-Pyrazinyl | |
| 1.187 | —CH₂—O—N=C(CH₃)— | -4-Pyrimidinyl | |
| 1.188 | —CH₂—O—N=C(CH₃)— | -3-Pyridinyl | |
| 1.189 | —CH₂—O—N=C(CH₃)— | -2-Furyl | |
| 1.190 | —CH₂—O—N=C(CH₃)— | -2-Thienyl | |
| 1.191 | —O— | -Phenyl | |
| 1.192 | —O— | -3-Methoxy-phenyl | |
| 1.193 | 1,4-phenylene-dioxy | -Phenyl | IR: 1746, 1699, 1483, 1237, 1028 cm⁻¹ |
| 1.194 | 1,4-phenylene-dioxy | -2-Fluorophenyl | |
| 1.195 | 1,4-phenylene-dioxy | -2-Chlorophenyl | |
| 1.196 | 1,4-phenylene-dioxy | 2-Cyano-phenyl | |
| 1.197 | 1,4-phenylene-dioxy | -2-Methyl-phenyl | |

-continued

| | | |
|---|---|---|
| 1.198 | [2,6-disubstituted phenyl] | -2-Nitro-phenyl |
| 1.199 | [2,6-disubstituted phenyl] | -2-Trifluoromethyl-phenyl |
| 1.200 | —O— | -4-Methylpyridin-2-yl |
| 1.201 | —O— | -4-Trifluoromethylpyridin-2-yl |
| 1.202 | —O— | -5-Chloropyridin-2-yl |
| 1.203 | —O— | -4-Chloropyrimidin-2-yl |
| 1.204 | [2,6-dioxy pyridinyl] | -Phenyl |
| 1.205 | [2,6-dioxy pyridinyl] | -2-Fluorophenyl |
| 1.206 | [2,6-dioxy pyridinyl] | -2-Chlorophenyl |
| 1.207 | [2,6-dioxy pyridinyl] | -2-Bromophenyl |
| 1.208 | [2,6-dioxy pyridinyl] | -2-Cyanophenyl |
| 1.209 | [2,6-dioxy pyridinyl] | 2-(NH$_2$—C(=S)—)Phenyl |

-continued
| | | |
|---|---|---|
| 1.210 | 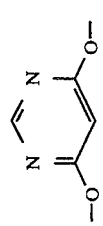 | -2-Nitrophenyl |
| 1.211 | 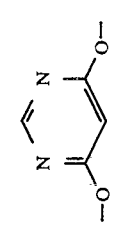 | -2-Methoxyphenyl |
| 1.212 | 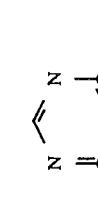 | -2-Methylphenyl |
| 1.213 | 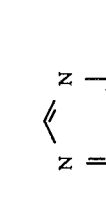 | -2-Trifluorophenyl |
| 1.214 | 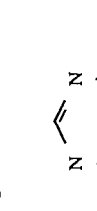 | -2-Cyano-4-chlorophenyl |
| 1.215 | 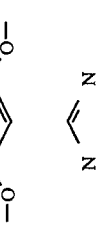 | -2,6-Difluorophenyl |
| 1.216 |  | -Phenyl |
| 1.217 | 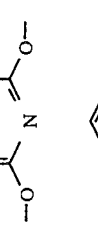 | -2-Cyanophenyl |

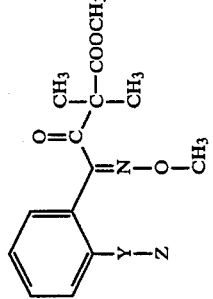
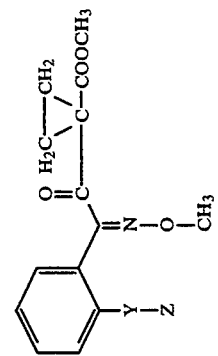

| | | | |
|---|---|---|---|
| 109 | —CH₂O— | — | —Ph |
| 110 | — | — | -(2-Me)Ph |
| 111 | — | — | -(2,4-DiMe)Ph |
| 112 | — | — | -(4-Cl, 2-Me)Ph |
| 113 | — | — | -(4-Cl)Ph |
| 114 | — | — | -(4-tBu, 2 Me)Ph |
| 115 | — | — | -(2,3,5-TriMe)Ph |
| 116 | — | — | -(4-Cyclohexyl, 2-Me)Ph |
| 117 | — | — | -(4-Phenyl)Ph |
| 118 | — | — | -(5-Me, 2-iPr)Ph |
| 119 | — | — | -(2,5-DiMe)Ph |
| 120 | — | — | -(2,5-DiEt)Ph |
| 121 | —CH₂—O—C(O)= | — | -(2-Me)Ph |
| 122 | — | — | -[1-(4-ClPhenyl)]cyclopropyl |
| 123 | — | — | -[1-(3,4-DiClPhenyl)]cyclopropyl |
| 124 | — | — | -[1-(4-Methoxyphenyl)]cyclopropyl |
| 125 | — | — | -(1-Methyl)cyclopropyl |
| 126 | —CH₂— | — | -[2,2-DiMethyl,3-(2,2'-Dibromoethylene)]cyclopropyl |
| 127 | —CH₂O— | — | —H |
| 128 | — | — | —Br |
| 129 | — | — | 4-(1-oxo)Ethyl-Ph |
| 130 | — | — | 4[1-(2-propenoxyimino)Ethyl-Ph |
| 131 | — | — | 4(1-Ethoxyimino)Ethyl-Ph |
| 132 | — | — | 4(1-Benzyloxyimino)Ethyl-Ph |
| 133 | — | — | 4(2-propenoxyimino)Methyl-Ph |
| 134 | — | — | 4(Ethyloxyimino)Methyl-Ph |
| 135 | — | — | 4(Benzyloxyimino)Methyl-Ph |

-continued

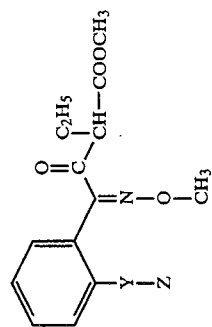

| | | |
|---|---|---|
| 136 | —CH₂O— | —Ph |
| 137 | — | -(2-Me)Ph |
| 138 | — | -(2,4-DiMe)Ph |
| 139 | — | -(4-Cl, 2-Me)Ph |
| 140 | — | -(4-Cl)Ph |
| 141 | — | -(4-tBu, 2 Me)Ph |
| 142 | — | -(2,3,5-TriMe)Ph |
| 143 | — | -(4-Cyclohexyl, 2-Me)Ph |
| 144 | — | -(4-Phenyl)Ph |
| 145 | — | -(5-Me, 2-iPr)Ph |
| 146 | — | -(2,5-DiMe)Ph |
| 147 | — | -(2,5-DiEt)Ph |
| 148 | —CH₂—O—C(=O)— | -(2-Me)Ph |
| 149 | — | -[1-(4-ClPhenyl)]cyclophenyl |
| 150 | — | -[1-(3,4-DiClPhenyl)]cyclopropyl |
| 151 | — | -[1-(4-Methoxyphenyl)]cyclopropyl |
| 152 | — | -(1-Methyl)cyclopropyl |
| 153 | — | -[2,2-DiMethyl,3-(2,2'-Dibromoethylene)]cyclopropyl |
| 154 | —CH₂— | —H |
| 155 | —CH₂O— | —Br |
| 156 | — | 4-(1-oxo)Ethyl-Ph |
| 157 | — | 4[1-(2-propenoxyimino)]Ethyl-Ph |
| 158 | — | 4(1-Ethyloxyimino)Ethyl-Ph |
| 159 | — | 4(1-Benzyloxyimino)Ethyl-Ph |
| 160 | — | 4(2-propenoxyimino)Methyl-Ph |
| 161 | — | 4(Ethyloxyimino)Methyl-Ph |
| 162 | — | 4(Benzyloxyimino)Methyl-Ph |
| 163 | —CH₂O— | —Ph |
| 164 | — | -(2-Me)Ph |
| 165 | — | -(2,4-DiMe)Ph |
| 166 | — | -(4-Cl, 2-Me)Ph |
| 167 | — | -(4-Cl)Ph |
| 168 | — | -(4-tBu, 2 Me)Ph |
| 169 | — | -(2,3,5-TriMe)Ph |
| 170 | — | -(4-Cyclohexyl, 2-Me)Ph |
| 171 | — | -(4-Phenyl)Ph |
| 172 | — | -(5-Me, 2-iPr)Ph |

-continued

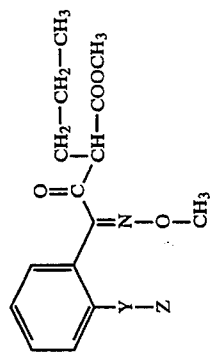

| | | |
|---|---|---|
| 173 | = | -(2,5-DiMe)Ph |
| 174 | = | -(2,5-DiEt)Ph |
| 175 | —CH₂—O—C(=O)— | -(2-Me)Ph |
| 176 | = | -[1-(4-ClPhenyl)]cyclopropyl |
| 177 | = | -[1-(3,4-DiClPhenyl)]cyclopropyl |
| 178 | = | -[1-(4-Methoxyphenyl)]cyclopropyl |
| 179 | = | -(1-Methyl)cyclopropyl |
| 180 | —CH₂— | -[2,2-DiMethyl,3-(2,2'-Dibromoethylene)]cyclopropyl |
| 181 | —CH₂O— | —H |
| 182 | = | —Br |
| 183 | = | 4-(1-oxo)Ethyl-Ph |
| 184 | = | 4[1-(2-propenoxyimino)]Ethyl-Ph |
| 185 | = | 4(1-Ethyloxyimino)Ethyl-Ph |
| 186 | = | 4(1-Benzyloxyimino)Ethyl-Ph |
| 187 | = | 4(2-propenoxyimino)Methyl-Ph |
| 188 | = | 4(Ethyloxyimino)Methyl-Ph |
| 189 | = | 4(Benzyloxyimino)Methyl-Ph |
| 190 | —CH₂O— | —Ph |
| 191 | = | -(2-Me)Ph |
| 192 | = | -(2,4-DiMe)Ph |
| 193 | = | -(4-Cl, 2-Me)Ph |
| 194 | = | -(4-Cl)Ph |
| 195 | = | -(4-tBu, 2 Me)Ph |
| 196 | = | -(2,3,5-TriMe)Ph |
| 197 | = | -(4-Cyclohexyl, 2-Me)Ph |
| 198 | = | -(4-Phenyl)Ph |
| 199 | = | -(5-Me, 2-iPr)Ph |
| 200 | = | -(2,5-DiMe)Ph |
| 201 | = | -(2,5-DiEt)Ph |
| 202 | —CH₂—O—C(=O)— | -(2-Me)Ph |
| 203 | = | -[1-(4-ClPhenyl)]cyclopropyl |
| 204 | = | -[1-(3,4-DiClPhenyl)]cyclopropyl |
| 205 | = | -[1-(4-Methoxyphenyl)]cyclopropyl |
| 206 | = | -(1-Methyl)cyclopropyl |

-continued
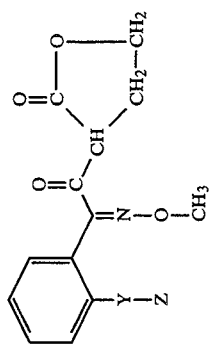
| | | | NMR: 7.70–6.70 (m,8H); 4.90 (m,3H); 4.55–4.25 (m,2H); 4.05 (s,3H); 2.80–2.10 (m,5H) ppm |
|---|---|---|---|
| 207 | —CH₂— | -[2,2-DiMethyl,3-(2,2'-Dibromoethylene)]cyclopropyl | |
| 208 | — | —H | |
| 209 | —CH₂O— | —Br | |
| 210 | — | 4-(1-oxo)Ethyl-Ph | |
| 211 | — | 4-[1-(2-propenoxyimino)]Ethyl-Ph | |
| 212 | — | 4-(1-Ethyloxyimino)Ethyl-Ph | |
| 213 | — | 4-(1-Benzyloxyimino)Ethyl-Ph | |
| 214 | — | 4-(2-propenoxyimino)Methyl-Ph | |
| 215 | — | 4-(Ethyloxyimino)Methyl-Ph | |
| 216 | — | 4-(Benzyloxyimino)Methyl-Ph | |
| 217 | —CH₂O— | —Ph | |
| 218 | — | -(2-Me)Ph | |
| 219 | — | -(2,4-DiMe)Ph | |
| 220 | — | -(4-Cl, 2-Me)Ph | |
| 221 | — | -(4-Cl)Ph | |
| 222 | — | -(4-tBu, 2-Me)Ph | |
| 223 | — | -(2,3,5-TriMe)Ph | |
| 224 | — | -(4-Cyclohexyl, 2-Me)Ph | |
| 225 | — | -(4-Phenyl)Ph | |
| 226 | — | -(5-Me, 2-iPr)Ph | |
| 227 | — | -(2,5-DiMe)Ph | |
| 228 | — | -(2,5-DiEt)Ph | |
| 229 | —CH₂—O—C(=O)— | -(2-Me)Ph | |

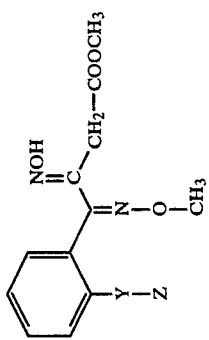

| No. | Y | Z |
|-----|---|---|
| 230 | — | -[1-(4-ClPhenyl)]cyclopropyl |
| 231 | — | -[1-(3,4-DiClPhenyl)]cyclopropyl |
| 232 | — | -[1-(4-Methoxyphenyl)]cyclopropyl |
| 233 | — | -(1-Methyl)cyclopropyl |
| 234 | — | -[2,2-DiMethyl,3-(2,2'-Dibromoethylene)]cyclopropyl |
| 235 | —CH₂— | —H |
| 236 | —CH₂O— | —Br |
| 237 | — | -4-(1-oxo)Ethyl-Ph |
| 238 | — | -4[1-(2-propenoxyimino)]Ethyl-Ph |
| 239 | — | -4(1-Ethoxyimino)Ethyl-Ph |
| 240 | — | -4(1-Benzyloxyimino)Ethyl-Ph |
| 241 | — | -4(2-propenoxyimino)Methyl-Ph |
| 242 | — | -4(Ethyloxyimino)Methyl-Ph |
| 243 | — | -4(Benzyloxyimino)Methyl-Ph |
| 244 | —CH₂O— | —Ph |
| 245 | — | -(2-Me)Ph |
| 246 | — | -(2,4-DiMe)Ph |
| 247 | — | -(4-Cl, 2-Me)Ph |
| 248 | — | -(4-Cl)Ph |
| 249 | — | -(4-tBu, 2 Me)Ph |
| 250 | — | -(2,3,5-TriMe)Ph |
| 251 | — | -(4-Cyclohexyl, 2-Me)Ph |
| 252 | — | -(4-Phenyl)Ph |
| 253 | — | -(5-Me, 2-iPr)Ph |
| 254 | — | -(2,5-DiMe)Ph |
| 255 | — | -(2,5-DiEt)Ph |
| 256 | —CH₂—O—C(=O)— | -(2-Me)Ph |
| 257 | — | -[1-(4-ClPhenyl)]cyclopropyl |
| 258 | — | -[1-(3,4-DiClPhenyl)]cyclopropyl |
| 259 | — | -[1-(4-Methoxyphenyl)]cyclopropyl |
| 260 | — | -(1-Methyl)cyclopropyl |
| 261 | — | -[2,2-DiMethyl,3-(2,2'-Dibromoethylene)]cyclopropyl |
| 262 | —CH₂— | —H |
| 263 | —CH₂O— | —Br |
| 264 | — | -4-(1-oxo)Ethyl-Ph |
| 265 | — | -4[1-(2-propenoxyimino)]Ethyl-Ph |
| 266 | — | -4(1-Ethoxyimino)Ethyl-Ph |
| 267 | — | -4(1-Benzyloxyimino)Ethyl-Ph |

-continued

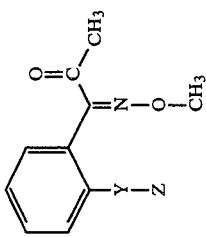

| # | Y | Z | IR |
|---|---|---|---|
| 268 | — | -4(2-propenoxyimino)Methyl-Ph | |
| 269 | — | -4(Ethyloxyimino)Methyl-Ph | |
| 270 | — | -4(Benzyloxyimino)Methyl-Ph | |
| 271 | —CH$_2$O— | —Ph | IR: 1694, 1495, 1462, 1241, 1123 |
| 272 | — | -(2-Me)Ph | |
| 273 | — | -(2,4-DiMe)Ph | IR: 16,94 1503, 1224, 1061, 1009 |
| 274 | — | -(4-Cl, 2-Me)Ph | IR: 1693, 1492, 1244, 1190, 1010 |
| 275 | — | -(4-Cl)Ph | |
| 276 | — | -(4-tBu, 2 Me)Ph | IR: 1694, 1491, 1241, 1061, 1009 |
| 277 | — | -(2,3,5-TriMe)Ph | |
| 278 | — | -(4-Cyclohexyl, 2-Me)Ph | IR: 1681, 1104, 1056, 1001, 757 |
| 279 | — | -(4-Pheny])Ph | |
| 280 | — | -(5-Me, 2-iPr)Ph | |
| 281 | — | -(2,5-DiMe)Ph | IR: 1686, 1130, 1056, 1042, 1003 |
| 282 | — | -(2,5-DiEt)Ph | |
| 283 | —CH$_2$—O—C(=O)— | -(2-Me)Ph | |
| 284 | — | -[1-(4-ClPhenyl)]cyclopropyl | |
| 285 | — | -[1-(3,4-DiClPhenyl)]cyclopropyl | |
| 286 | — | -[1-(4-Methoxyphenyl)]cyclopropyl | |
| 287 | — | -(1-Methyl)cyclopropyl | |
| 288 | —CH$_2$— | -[2,2-DiMethyl,3-(2,2'-Dibromoethylene)]cyclopropyl | |
| 289 | — | —H | |
| 290 | —CH$_2$O— | —Br | |
| 291 | — | -4-(1-oxo)Ethyl-Ph | |
| 292 | — | -4[1-(2-propenoxyimino)]Ethyl-Ph | |
| 293 | — | -4(1-Ethyloxyimino)Ethyl-Ph | |
| 294 | — | -4(1-Benzyloxyimino)Ethyl-Ph | |
| 295 | — | -4(2-propenoxyimino)Ethyl-Ph | |
| 296 | — | -4(Ethyloxyimino)Methyl-Ph | |
| 297 | — | -4(Benzyloxyimino)Methyl-Ph | |
| 1.298 | —CH$_2$O— | -2-Methyl-4-(1-oxo)ethyl-Ph | IR: 1672, 1597, 1259, 1244, 1010 |
| 1.299 | —CH$_2$O— | -2-Methyl-4-(1-benzyloxyimino)ethyl-Ph | IR: 1674, 1599, 1263, 995, 987 |
| 1.300 | —CH$_2$O— | -2-Methyl-4-(1-ethyloxyimino)ethyl-Ph | IR: 1668, 1598, 1264, 1064, 989 |
| 1.301 | —CH$_2$O— | -2-Methyl-4-(1-methyloxyimino)ethyl-Ph | IR: 1693, 1504, 1243, 1051, 1009 |
| 1.302 | —CH$_2$O— | -2-Methyl-4-(1-cyclohexylmethyloxyimino)ethyl-Ph | IR: 1679, 1230, 1146, 1036, 987 |
| 1.303 | —CH$_2$O— | -2-Methyl-4-(1-n-propyloxyimino)ethyl-Phenyl | |
| 1.304 | —CH$_2$O— | -2-Methyl-4-(1-isopropyloxyimino)ethyl-Phenyl | |
| 1.305 | —CH$_2$O— | -2-Methyl-4-(1-n-butyloxyimino)ethyl-Phenyl | |

-continued

| No. | | Substituent | IR |
|---|---|---|---|
| 1.306 | —CH$_2$O— | 2-Methyl-4-(1-isobutyloxyimino)ethyl-Phenyl | |
| 1.307 | —CH$_2$O— | 2-Methyl-4-[1-(2-propenoxyimino)ethyl]-Phenyl | |
| 1.308 | —CH$_2$O— | 2-Methyl-4-[1-(2-propenoxyimino)ethyl]-Phenyl | |
| 1.309 | —CH$_2$O— | 2-Methyl-4-(1-oxo)propyl-Phenyl | |
| 1.310 | —CH$_2$O— | 2-Methyl-4-(1-methoxyimino)propyl-Phenyl | |
| 1.311 | —CH$_2$O— | 2-Methyl-4-(1-ethoxyimino)propyl-Phenyl | |
| 1.312 | —CH$_2$O— | 2-Methyl-4-(1-n-propyloxyimino)propyl-Phenyl | |
| 1.313 | —CH$_2$O— | 2-Methyl-4-(1-iso-propyloxyimino)propyl-Phenyl | |
| 1.314 | —CH$_2$O— | 2-Methyl-4-[1-(2-propenoxyimino)propyl-Phenyl | |
| 1.315 | —CH$_2$O— | 2-Methyl-4-[3-chloro-E-2-propenoxyimino)propyl-Phenyl | |
| 1.316 | —CH$_2$O— | 2-Methyl-4-(1-benzyloxyimino)propyl-Phenyl | |
| 1.317 | —CH$_2$O— | 2,5-Dimethyl-4-(1-oxo)ethyl-Phenyl | |
| 1.318 | —CH$_2$O— | 2,5-Dimethyl-4-(1-methoxyimino)ethyl-Phenyl | |
| 1.319 | —CH$_2$O— | 2,5-Dimethyl-4-(1-ethoxyimino)ethyl-Phenyl | |
| 1.320 | —CH$_2$O— | 2,5-Dimethyl-4-(1-n-propyloxyimino)ethyl-Phenyl | |
| 1.321 | —CH$_2$O— | 4,5-Dimethyl-4-(1-iso-propyloxyimino)ethyl-Phenyl | |
| 1.322 | —CH$_2$O— | 2,5-Dimethyl-4-[1-(2-propenoxyimino)ethyl-Phenyl | |
| 1.323 | —CH$_2$O— | 2,5-Dimethyl-4-[1-(3-chloro-E-2-propenoxyimino)ethyl-Phenyl | |
| 1.324 | —CH$_2$O— | 2,5-Dimethyl-4-(1-benzyloxyimino)ethyl-Phenyl | |
| 1.325 | —CH$_2$—O—N=C(CH$_3$)— | -3,5-Dichlorophenyl | 1693, 1508, 1061, 1045, 1009 cm$^{-1}$ |
| 1.326 | —CH$_2$—O—N=C(CH$_3$)— | -4-Trifluoromethyl-phenyl | |
| 1.327 | —CH$_2$—O—N=C(CH$_3$)— | -3-Trifluoromethyl-phenyl | |
| 1.328 | —CH$_2$—O—N=C(CH$_3$)— | -4-Bromophenyl | |
| 1.329 | —CH$_2$—O—N=C(CH$_3$)— | -4-tert-Butyl-phenyl | |
| 1.330 | —CH$_2$—O—N=C(CH$_3$)— | -2,4-Dimethyl-phenyl | |
| 1.331 | —CH$_2$—O—N=C(CH$_3$)— | -3,4-Dichlorophenyl | |
| 1.332 | —CH$_2$—O—N=C(CH$_3$)— | -2-Methyl-phenyl | |
| 1.333 | —CH$_2$—O—N=C(CH$_3$)— | -4-Nitro-phenyl | |

-continued

| | | |
|---|---|---|
| 1.334 | -CH$_2$-O-N=C(CH$_3$)- | -4-Methyl-phenyl |
| 1.335 | -CH$_2$-O-N=C(CH$_3$)- | -2-Pyrazinyl |
| 1.336 | -CH$_2$-O-N=C(CH$_3$)- | -4-Pyrimidinyl |
| 1.337 | -CH$_2$-O-N=C(CH$_3$)- | -3-Pyridinyl |
| 1.338 | -CH$_2$-O-N=C(CH$_3$)- | -2-Furyl |
| 1.339 | -CH$_2$-O-N=C(CH$_3$)- | -2-Thienyl |
| 1.340 | -O- | -Phenyl |
| 1.341 | -O- | -3-Methoxy-phenyl |
| 1.342 | 1,3-phenylene-dioxy | -Phenyl |
| 1.343 | 1,3-phenylene-dioxy | -2-Fluorophenyl |
| 1.344 | 1,3-phenylene-dioxy | -2-Chlorophenyl |
| 1.345 | 1,3-phenylene-dioxy | 2-Cyano-phenyl |

-continued

| | | |
|---|---|---|
| 1.346 | [3-substituted phenyl ring] | -2-Methyl-phenyl |
| 1.347 | [3-substituted phenyl ring] | -2-Nitro-phenyl |
| 1.348 | [3-substituted phenyl ring] | -2-Trifluoromethyl-phenyl |
| 1.349 | — | -4-Methylpyridin-2-yl |
| 1.350 | — | -4-Trifluoromethylpyridin-2-yl |
| 1.351 | — | -5-Chloropyridin-2-yl |
| 1.352 | — | -4-Chloropyrimidin-2-yl |
| 1.353 | [pyrimidine ring] | -Phenyl |
| 1.354 | [pyrimidine ring] | -2-Fluorophenyl |
| 1.354 | [pyrimidine ring] | -2-Chlorophenyl |
| 1.356 | [pyrimidine ring] | -2-Bromophenyl |
| 1.357 | [pyrimidine ring] | -2-Cyanophenyl |

-continued

| # | Structure | Substituent |
|---|---|---|
| 1.358 | pyrimidine-4,6-diyl-dioxy | 2-(NH₂—C(=S))Phenyl |
| 1.359 | pyrimidine-4,6-diyl-dioxy | -2-Nitrophenyl |
| 1.360 | pyrimidine-4,6-diyl-dioxy | -2-Methoxyphenyl |
| 1.361 | pyrimidine-4,6-diyl-dioxy | -2-Methylphenyl |
| 1.362 | pyrimidine-4,6-diyl-dioxy | -2-Trifluoromethyl-phenyl |
| 1.363 | pyrimidine-4,6-diyl-dioxy | -2-Cyano-4-chlorophenyl |
| 1.364 | pyrimidine-4,6-diyl-dioxy | -2,6-Difluorophenyl |
| 1.365 | pyrimidine-2,4-diyl-dioxy | -Phenyl |
| 1.366 | pyrimidine-2,4-diyl-dioxy | -2-Cyanophenyl |

-continued

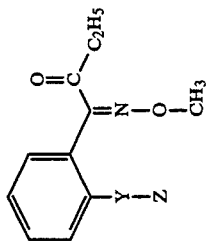

| # | Y | N | mp/IR |
|---|---|---|---|
| 298 | —CH₂O | —Ph | |
| 299 | — | -(2-Me)Ph | |
| 300 | — | -(2,4-DiMe)Ph | |
| 301 | — | -(4-Cl, 2-Me)Ph | |
| 302 | — | -(4-Cl)Ph | |
| 303 | — | -(4-tBu, 2 Me)Ph | |
| 304 | — | -(2,3,5-TriMe)Ph | |
| 305 | — | -(4-Cyclohexyl, 2-Me)Ph | |
| 306 | — | -(4-Phenyl)Ph | |
| 307 | — | -(5-Me, 2-iPr)Ph | |
| 308 | — | -(2,5-DiMe)Ph | |
| 309 | — | -(2,5-DiEt)Ph | |
| 310 | —CH₂—O—C(O)= | -(2-Me)Ph | 107° C. |
| 311 | — | -[1-(4-ClPhenyl)]cyclopropyl | |
| 312 | — | -[1-(3,4-DiClPhenyl)]cyclopropyl | |
| 313 | — | -[1-(4-Methoxyphenyl)]cyclopropyl | |
| 314 | — | -(1-Methyl)cyclopropyl | |
| 315 | —CH₂ | -[2,2-DiMethyl,3-(2,2'-Dibromoethylene)]cyclopropyl | |
| 316 | — | —H | |
| 317 | —CH₂O | —Br | |
| 318 | — | 4-(1-oxo)Ethyl-Ph | |
| 319 | — | 4[1-(2-propenoxyimino)]Ethyl-Ph | |
| 320 | — | 4(1-Ethyloxyimino)Ethyl-Ph | |
| 321 | — | 4(1-Benzyloxyimino)Ethyl-Ph | |
| 322 | — | 4(2-propenoxyimino)Methyl-Ph | |
| 323 | — | 4(Ethyloxyimino)Methyl-Ph | |
| 324 | — | 4(Benzyloxyimino)Methyl-Ph | |
| 1.367 | —CH₂O | 2-Methyl-4-(1-oxo)ethyl-Phenyl | IR: 2975, 2937, 1697, 1032, 761 |
| 1.368 | —CH₂O | 2-Methyl-4-(1-methoxyimino)ethyl-Phenyl | |
| 1.369 | —CH₂O | 2-Methyl-4-(1-ethoxyimino)ethyl-Phenyl | |
| 1.370 | —CH₂O | 2-Methyl-4-(1-n-propyloxyimino)ethyl-Phenyl | |
| 1.371 | —CH₂O | 2-Methyl-4-(1-isopropyloxyimino)ethyl-Phenyl | |
| 1.372 | —CH₂O | 2-Methyl-4-(1-n-butyloxyimino)ethyl-Phenyl | |
| 1.373 | —CH₂O | 2-Methyl-4-(1-isobutyloxyimino)ethyl-Phenyl | |
| 1.374 | —CH₂O | 2-Methyl-4-[1-(2-propenoxyimino)]ethyl-Phenyl | |
| 1.375 | —CH₂O | 2-Methyl-4-[1-(3-chloro-E-2-propenoxyimino)]ethyl-Phenyl | |
| 1.376 | —CH₂O | 2-Methyl-4-(1-benzyloxyimino)ethyl-Phenyl | |
| 1.377 | —CH₂O | 2-Methyl-4-(1-oxo)propyl-Phenyl | IR: 1694, 1505, 1244, 1050, 1033 |

-continued

| No. | | Aryl | IR |
|---|---|---|---|
| 1.378 | —CH₃O | 2-Methyl-4-(1-methoxyimino)propyl-Phenyl | |
| 1.379 | —CH₃O | 2-Methyl-4-(1-ethoxyimino)propyl-Phenyl | |
| 1.380 | —CH₃O | 2-Methyl-4-(1-n-propyloxyimino)propyl-Phenyl | |
| 1.381 | —CH₃O | 2-Methyl-4-(1-iso-propyloxyimino)propyl-Phenyl | |
| 1.382 | —CH₃O | 2-Methyl-4-[1-(2-propenoxyimino)]propyl-Phenyl | |
| 1.383 | —CH₃O | 2-Methyl-4-[3-chlor-E-2-propenoxyimino)]propyl-Phenyl | |
| 1.384 | —CH₃O | 2-Methyl-4-(1-benzyloxyimino)propyl-Phenyl | |
| 1.385 | —CH₃O | 2,5-Dimethyl-4-(1-oxo)ethyl-Phenyl | |
| 1.386 | —CH₃O | 2,5-Dimethyl-4-(1-methoxyimino)ethyl-Phenyl | |
| 1.387 | —CH₃O | 2,5-Dimethyl-4-(1-ethoxyimino)ethyl-Phenyl | |
| 1.388 | —CH₃O | 2,5-Dimethyl-4-(1-n-propyloxyimino)ethyl-Phenyl | |
| 1.389 | —CH₃O | 4,5-Dimethyl-4-(1-iso-propyloxyimino)ethyl-Phenyl | |
| 1.390 | —CH₃O | 2,5-Dimethyl-4-[1-(2-propenoxyimino)]ethyl-Phenyl | |
| 1.391 | —CH₃O | 2,5-Dimethyl-4-[1-(3-chloro-E-2-propenoxyimino)]ethyl-Phenyl | |
| 1.392 | —CH₃O | 2,5-Dimethyl-4-(1-benzyloxyimino)ethyl-Phenyl | |
| 1.393 | —CH₂—O—N=C(CH₃)— | 3,5-Dichlorophenyl | |
| 1.394 | —CH₂—O—N=C(CH₃)— | 4-Trifluoromethyl-phenyl | |
| 1.395 | —CH₂—O—N=C(CH₃)— | 3-Trifluoromethyl-phenyl | |
| 1.396 | —CH₂—O—N=C(CH₃)— | 4-Bromophenyl | |
| 1.397 | —CH₂—O—N=C(CH₃)— | 4-tert-Butyl-phenyl | |
| 1.398 | —CH₂—O—N=C(CH₃)— | 2,4-Dimethyl-phenyl | |
| 1.399 | —CH₂—O—N=C(CH₃)— | 3,4-Dichlorophenyl | |
| 1.400 | —CH₂—O—N=C(CH₃)— | 2-Methyl-phenyl | |
| 1.401 | —CH₂—O—N=C(CH₃)— | 4-Nitro-phenyl | |
| 1.402 | —CH₂—O—N=C(CH₃)— | 4-Methyl-phenyl | IR: 1694, 1508, 1246, 1150, 1034 |

| No. | | | |
|---|---|---|---|
| 1.403 | —CH₂—O—N=C(CH₃)— | -2-Pyrazinyl | |
| 1.404 | —CH₂—O—N=C(CH₃)— | -4-Pyrimidinyl | |
| 1.405 | —CH₂—O—N=C(CH₃)— | -3-Pyridinyl | |
| 1.406 | —CH₂—O—N=C(CH₃)— | -2-Furyl | |
| 1.407 | —CH₂—O—N=C(CH₃)— | -2-Thienyl | |
| 1.408 | —O— | -Phenyl | |
| 1.409 | —O— | -3-Methoxy-phenyl | |
| 1.410 | 1,3-phenylene-di-oxy | -Phenyl | |
| 1.411 | 1,3-phenylene-di-oxy | -2-Fluorophenyl | |
| 1.412 | 1,3-phenylene-di-oxy | -2-Chlorophenyl | |
| 1.413 | 1,3-phenylene-di-oxy | -2-Cyano-phenyl | IR: 1697, 1483, 1235, 1035, 753 cm⁻¹ |
| 1.414 | 1,3-phenylene-di-oxy | -2-Methyl-phenyl | |

-continued

| | | |
|---|---|---|
| 1.415 | (1,3-disubstituted phenyl) | -2-Nitro-phenyl |
| 1.416 | (1,3-disubstituted phenyl) | -2-Trifluoromethyl-phenyl |
| 1.417 | —O— | -4-Methylpyridin-2-yl |
| 1.418 | —O— | -4-Trifluoromethylpyridin-2-yl |
| 1.419 | —O— | -5-Chloropyridin-2-yl |
| 1.420 | —O— | -4-Chloropyrimidin-2-yl |
| 1.421 | (pyridine-2,4-diyl dioxy) | -Phenyl |
| 1.422 | (pyridine-2,4-diyl dioxy) | -2-Fluorophenyl |
| 1.423 | (pyridine-2,4-diyl dioxy) | -2-Chlorophenyl |
| 1.424 | (pyridine-2,4-diyl dioxy) | -2-Bromophenyl |
| 1.425 | (pyridine-2,4-diyl dioxy) | -2-Cyanophenyl |
| 1.426 | (pyridine-2,4-diyl dioxy) | 2-(NH$_2$—C(=S)—)Phenyl |

-continued

| | Structure | Substituent |
|---|---|---|
| 1.427 | 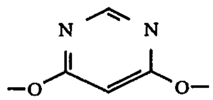 | -2-Nitrophenyl |
| 1.428 | 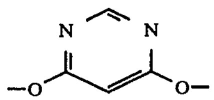 | -2-Methoxyphenyl |
| 1.429 | 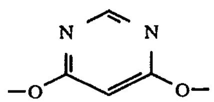 | -2-Methylphenyl |
| 1.430 | 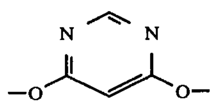 | -2-Trifluoromethyl-phenyl |
| 1.431 | 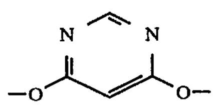 | -2-Cyano-4-chlorophenyl |
| 1.432 | 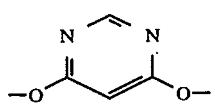 | -2,6-Difluorophenyl |
| 1.433 | 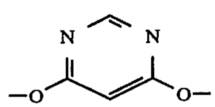 | -Phenyl |
| 1.434 | 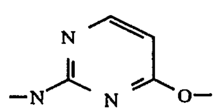 | -2-Cyanophenyl |

-continued

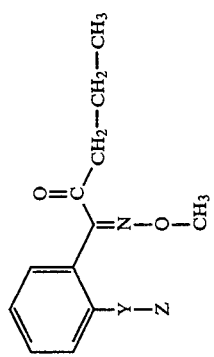

| | | | |
|---|---|---|---|
| 325 | —CH₂O— | | —Ph |
| 326 | — | | -(2-Me)Ph |
| 327 | — | | -(2,4-DiMe)Ph |
| 328 | — | | -(4-Cl, 2-Me)Ph |
| 329 | — | | -(4-Cl)Ph |
| 330 | — | | -(4-tBu, 2-Me)Ph |
| 331 | — | | -(2,3,5-TriMe)Ph |
| 332 | — | | -(4-Cyclohexyl, 2-Me)Ph |
| 333 | — | | -(4-Phenyl)Ph |
| 334 | — | | -(5-Me, 2-iPr)Ph |
| 335 | — | | -(2,5-DiMe)Ph |
| 336 | — | | -(2,5-DiEt)Ph |
| 337 | —CH₂—O—C(=O)— | | -(2-Me)Ph |
| 338 | — | | -[1-(4-ClPhenyl)]cyclopropyl |
| 339 | — | | -[1-(3,4-DiClPhenyl)]cyclopropyl |
| 340 | — | | -[1-(4-Methoxyphenyl)]cyclopropyl |
| 341 | — | | -(1-Methyl)cyclopropyl |
| 342 | — | | -[2,2-DiMethyl,3-(2,2′-Dibromoethylene)]cyclopropyl |
| 343 | —CH₂— | | —H |
| 344 | —CH₂O— | | —Br |
| 345 | — | | -4-(1-oxo)Ethyl-Ph |
| 346 | — | | -4[1-(2-propenoxyimino)]Ethyl-Ph |
| 347 | — | | -4(1-Ethyloxyimino)Ethyl-Ph |
| 348 | — | | -4(1-Benzyloxyimino)Ethyl-Ph |
| 349 | — | | -4(2-propenoxyimino)Methyl-Ph |
| 350 | — | | -4(Ethyloxyimino)Methyl-Ph |
| 351 | — | | -4(Benzyloxyimino)Methyl-Ph |

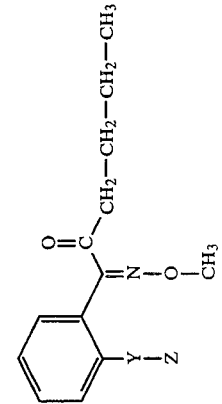

-continued

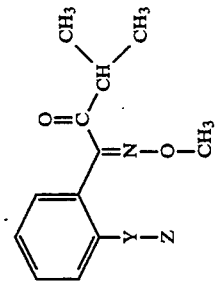

| # | Linker | R |
|---|---|---|
| 352 | —CH₂O— | —Ph |
| 353 | — | -(2-Me)Ph |
| 354 | — | -(2,4-DiMe)Ph |
| 355 | — | -(4-Cl, 2-Me)Ph |
| 356 | — | 4(4-Cl)Ph |
| 357 | — | -(4-tBu, 2 Me)Ph |
| 358 | — | -(2,3,5-TriMe)Ph |
| 359 | — | -(4-Cyclohexyl, 2-Me)Ph |
| 360 | — | -(4-Phenyl)Ph |
| 361 | — | -(5-Me, 2-iPr)Ph |
| 362 | — | -(2,5-DiMe)Ph |
| 363 | — | -(2,5-DiEt)Ph |
| 364 | —CH₂—O—C(=O)— | -(2-Me)Ph |
| 365 | — | -[1-(4-ClPhenyl)]cyclopropyl |
| 366 | — | -[1-(3,4-DiClPhenyl)]cyclopropyl |
| 367 | — | -[1-(4-Methoxyphenyl)]cyclopropyl |
| 368 | — | -(1-Methyl)cyclopropyl |
| 369 | — | -[2,2-DiMethyl,3-(2,2'-Dibromoethylene)]cyclopropyl |
| 370 | —CH₂— | —H |
| 371 | —CH₂O— | —Br |
| 372 | — | 4-(1-oxo)Ethyl-Ph |
| 373 | — | 4[1-(2-propenoxyimino)]Ethyl-Ph |
| 374 | — | 4(1-Ethyloxyimino)Ethyl-Ph |
| 375 | — | 4(1-Benzyloxyimino)Ethyl-Ph |
| 376 | — | 4(2-propenoxyimino)Methyl-Ph |
| 377 | — | 4(Ethyloxyimino)Methyl-Ph |
| 378 | — | 4(Benzyloxyimino)Methyl-Ph |
| 379 | —CH₂O— | —Ph |
| 380 | — | -(2-Me)Ph |
| 381 | — | -(2,4-DiMe)Ph |
| 382 | — | -(4-Cl, 2-Me)Ph |
| 383 | — | -(4-Cl)Ph |
| 384 | — | -(4-tBu, 2 Me)Ph |
| 385 | — | -(2,3,5-TriMe)Ph |
| 386 | — | -(4-Cyclohexyl, 2-Me)Ph |
| 387 | — | -(4-Phenyl)Ph |
| 388 | — | -(5-Me, 2-iPr)Ph |

-continued

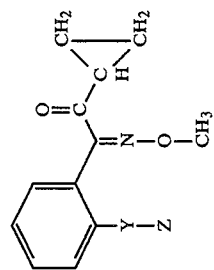

| # | Y | Z | Substituent | IR |
|---|---|---|---|---|
| 389 | — | — | -(2,5-DiMe)Ph | |
| 390 | — | — | -(2,5-DiEt)Ph | |
| 391 | -CH₂—O—C(O)= | | -(2-Me)Ph | |
| 392 | — | — | -[1-(4-ClPhenyl)]cyclopropyl | |
| 393 | — | — | -[1-(3,4-DiClPhenyl)]cyclopropyl | |
| 394 | — | — | -[1-(4-Methoxyphenyl)]cyclopropyl | |
| 395 | — | — | -(1-Methyl)cyclopropyl | |
| 396 | — | — | -[2,2-DiMethyl,3-(2,2'-Dibromoethylene)]cyclopropyl | |
| 397 | -CH₂ | | —H | |
| 398 | -CH₂O | | —Br | |
| 399 | — | — | -4-(1-oxo)Ethyl-Ph | |
| 400 | — | — | -4[1-(2-propenoxyimino)]Ethyl-Ph | |
| 401 | — | — | -4(1-Ethyloxyimino)Ethyl-Ph | |
| 402 | — | — | -4(1-Benzyloxyimino)Ethyl-Ph | |
| 403 | — | — | -4-(2-propenoxyimino)Methyl-Ph | |
| 404 | — | — | -4(Ethyloxyimino)Methyl-Ph | IR: 1691, 1512, 1246, 1177, 1030 |
| 405 | — | — | -4(Benzyloxyimino)Methyl-Ph | IR: 1691, 1511, 1246, 1049, 1030 |
| 406 | -CH₂O | | —Ph | IR: 1691, 1511, 1247, 1177, 1029 |
| 407 | — | — | -(2-Me)Ph | |
| 408 | — | — | -(2,4-DiMe)Ph | |
| 409 | — | — | -(4-Cl, 2-Me)Ph | |
| 410 | — | — | -(4-Cl)Ph | |
| 411 | — | — | -(4-tBu, 2 Me)Ph | |
| 412 | — | — | -(2,3,5-TriMe)Ph | |
| 413 | — | — | -(4-Cyclohexyl, 2-Me)Ph | |
| 414 | — | — | -(4-Phenyl)Ph | |
| 415 | — | — | -(5-Me, 2-iPr)Ph | |
| 416 | — | — | -(2,5-DiMe)Ph | |
| 417 | — | — | -(2,5-DiEt)Ph | |
| 418 | -CH₂—O—C(O)= | | -(2-Me)Ph | |
| 419 | — | — | -[1-(4-ClPhenyl)]cyclopropyl | |
| 420 | — | — | -[1-(3,4-DiClPhenyl)]cyclopropyl | |
| 421 | — | — | -[1-(4-Methoxyphenyl)]cyclopropyl | |
| 422 | — | — | -(1-Methyl)cyclopropyl | |

-continued

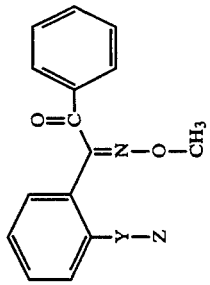

NMR: 8.05(d,2H); 7.60–7.15(m,14H); 6.90(d,2H); 5.00(s,2H); 3.90(s,3H)

| | Y | |
|---|---|---|
| 423 | —CH₂— | -[2,2-DiMethyl,3-(2,2'-Dibromoethylene)]cyclopropyl |
| 424 | —CH₂O— | —H |
| 425 | — | —Br |
| 426 | — | 4-(1-oxo)Ethyl-Ph |
| 427 | — | 4[1-(2-propenoxyimino)]Ethyl-Ph |
| 428 | — | 4(1-Ethyloxyimino)Ethyl-Ph |
| 429 | — | 4(1-Benzyloxyimino)Ethyl-Ph |
| 430 | — | 4(2-propenoxyimino)Methyl-Ph |
| 431 | — | 4(Ethyloxyimino)Methyl-Ph |
| 432 | — | 4(Benzyloxyimino)Methyl-Ph |
| 433 | —CH₂O— | -Ph |
| 434 | — | -(2-Me)Ph |
| 435 | — | -(2,4-DiMe)Ph |
| 436 | — | -(4-Cl, 2-Me)Ph |
| 437 | — | -(4-Cl)Ph |
| 438 | — | -(4-tBu, 2 Me)Ph |
| 439 | — | -(2,3,5-TriMe)Ph |
| 440 | — | -(4-Cyclohexyl, 2-Me)Ph |
| 441 | — | -(4-Phenyl)Ph |
| 442 | — | -(5-Me, 2-iPr)Ph |
| 443 | — | -(2,5-DiMe)Ph |
| 444 | — | -(2,5-DiEt)Ph |
| 445 | —CH₂—O—C(O)— | -(2-Me)Ph |
| 446 | — | -[1-(4-ClPhenyl)]cyclopropyl |
| 447 | — | -[1-(3,4-DiClPhenyl)]cyclopropyl |
| 448 | — | -[1-(4-Methoxyphenyl)]cyclopropyl |
| 449 | — | -(1-Methyl)cyclopropyl |
| 450 | — | -[2,2-DiMethyl,3-(2,2'-Dibromoethylene)]cyclopropyl |
| 451 | —CH₂— | —H |
| 452 | —CH₂O— | —Br |
| 453 | — | 4-(1-oxo)Ethyl-Ph |
| 454 | — | 4[1-(2-propenoxyimino)]Ethyl-Ph |
| 455 | — | 4(1-Ethyloxyimino)Ethyl-Ph |
| 456 | — | 4(1-Benzyloxyimino)Ethyl-Ph |
| 457 | — | 4(2-propenoxyimino)Methyl-Ph |
| 458 | — | 4(Ethyloxyimino)Methyl-Ph |
| 459 | — | 4(Benzyloxyimino)Methyl-Ph |

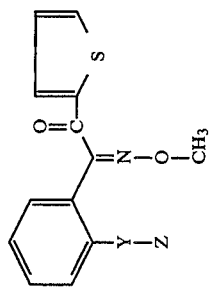
| | | Y—Z | |
|---|---|---|---|
| 460 | —CH₂O— | | —Ph |
| 461 | | | -(2-Me)Ph |
| 462 | | | -(2,4-DiMe)Ph |
| 463 | | | -(4-Cl, 2-Me)Ph |
| 464 | | | -(4-Cl)Ph |
| 465 | | | -(4-tBu, 2-Me)Ph |
| 466 | | | -(2,3,5-TriMe)Ph |
| 467 | | | -(4-Cyclohexyl, 2-Me)Ph |
| 468 | | | -(4-Phenyl)Ph |
| 469 | | | -(5-Me, 2-iPr)Ph |
| 470 | | | -(2,5-DiMe)Ph |
| 471 | | | -(2,5-DiEt)Ph |
| 472 | —CH₂—O—C(=O)— | | -(2-Me)Ph |

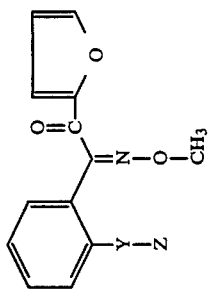

IR: 1649, 1462, 1028, 1017, 752

| # | | Y-N |
|---|---|---|
| 473 | — | -[1-(4-ClPhenyl)]cyclopropyl |
| 474 | — | -[1-(3,4-DiClPhenyl)]cyclopropyl |
| 475 | — | -[1-(4-Methoxyphenyl)]cyclopropyl |
| 476 | — | -(1-Methyl)cyclopropyl |
| 477 | — | -[2,2-DiMethyl,3-(2,2'-Dibromoethylene)]cyclopropyl |
| 478 | —CH$_2$— | —H |
| 479 | —CH$_2$O— | —Br |
| 480 | — | -4-(1-oxo)Ethyl-Ph |
| 481 | — | -4[1-(2-propenoxyimino)]Ethyl-Ph |
| 482 | — | -4(1-Ethyloxyimino)Ethyl-Ph |
| 483 | — | -4(1-Benzyloxyimino)Ethyl-Ph |
| 484 | — | -4(2-propenoxyimino)Methyl-Ph |
| 485 | — | -4(Ethyloxyimino)Methyl-Ph |
| 486 | — | -4(Benzyloxyimino)Methyl-Ph |
| 487 | —CH$_2$O— | —Ph |
| 488 | — | -(2-Me)Ph |
| 489 | — | -(2,4-DiMe)Ph |
| 490 | — | -(4-Cl, 2-Me)Ph |
| 491 | — | -(4-Cl)Ph |
| 492 | — | -(4-tBu, 2 Me)Ph |
| 493 | — | -(2,3,5-TriMe)Ph |
| 494 | — | -(4-Cyclohexyl, 2-Me)Ph |
| 495 | — | -(4-Phenyl)Ph |
| 496 | — | -(5-Me, 2-iPr)Ph |
| 497 | — | -(2,5-DiMe)Ph |
| 498 | — | -(2,5-DiEt)Ph |
| 499 | —CH$_2$—O—C(=O)— | -(2-Me)Ph |
| 500 | — | -[1-(4-ClPhenyl)]cyclopropyl |
| 501 | — | -[1-(3,4-DiClPhenyl)]cyclopropyl |
| 502 | — | -[1-(4-Methoxyphenyl)]cyclopropyl |
| 503 | — | -(1-Methyl)cyclopropyl |
| 504 | — | -[2,2-DiMethyl,3-(2,2'-Dibromoethylene)]cyclopropyl |
| 505 | —CH$_2$— | —H |
| 506 | —CH$_2$O— | —Br |
| 507 | — | -4-(1-oxo)Ethyl-Ph |
| 508 | — | -4[1-(2-propenoxyimino)]Ethyl-Ph |
| 509 | — | -4(1-Ethyloxyimino)Ethyl-Ph |
| 510 | — | -4(1-Benzyloxyimino)Ethyl-Ph |

-continued

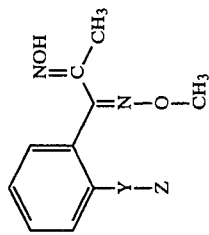

| | Y | Z |
|---|---|---|
| 511 | — | 4(2-propenoxyimino)Methyl-Ph |
| 512 | — | 4(Ethyloxyimino)Methyl-Ph |
| 513 | — | 4(Benzyloxyimino)Methyl-Ph |
| 514 | —CH$_2$O | —Ph |
| 515 | — | -(2-Me)Ph |
| 516 | — | -(2,4-DiMe)Ph |
| 517 | — | -(4-Cl, 2-Me)Ph |
| 518 | — | -(4-Cl)Ph |
| 519 | — | -(4-tBu, 2 Me)Ph |
| 520 | — | -(2,3,5-TriMe)Ph |
| 521 | — | -(4-Cyclohexyl, 2-Me)Ph |
| 522 | — | -(4-Phenyl)Ph |
| 523 | — | -(5-Me, 2-iPr)Ph |
| 524 | — | -(2,5-DiMe)Ph |
| 525 | — | -(2,5-DiEt)Ph |
| 526 | —CH$_2$—O—C(=O)— | -(2-Me)Ph |
| 527 | — | -[1-(4-ClPhenyl)]cyclopropyl |
| 528 | — | -[1-(3,4-DiClPhenyl)]cyclopropyl |
| 529 | — | -[1-(4-Methoxyphenyl)]cyclopropyl |
| 530 | — | -(1-Methyl)cyclopropyl |
| 531 | —CH$_2$ | -[2,2-DiMethyl,3-(2,2'-Dibromoethylene)]cyclopropyl |
| 532 | —CH$_2$O | —H |
| 533 | — | —Br |
| 534 | — | 4-(1-oxo)Ethyl-Ph |
| 535 | — | 4[1-(2-propenoxyimino)]Ethyl-Ph |
| 536 | — | 4(1-Ethyloxyimino)Ethyl-Ph |
| 537 | — | 4(1-Benzyloxyimino)Ethyl-)Ph |
| 538 | — | 4(2-propenoxyimino)Methyl-Ph |
| 539 | — | 4(Ethyloxyimino)Methyl-Ph |
| 540 | — | 4(Benzyloxyimino)Methyl-Ph |

-continued

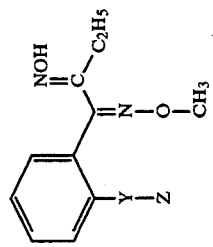         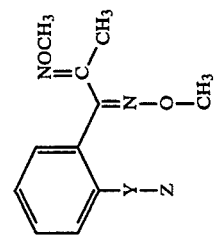

| No. | Y | Z |
|---|---|---|
| 541 | —CH₂O | —Ph |
| 542 | — | -(2-Me)Ph |
| 543 | — | -(2,4-DiMe)Ph |
| 544 | — | -(4-Cl, 2-Me)Ph |
| 545 | — | -(4-Cl)Ph |
| 546 | — | -(4-tBu, 2-Me)Ph |
| 547 | — | -(2,3,5-TriMe)Ph |
| 548 | — | -(4-Cyclohexyl, 2-Me)Ph |
| 549 | — | -(4-Phenyl)Ph |
| 550 | — | -(5-Me, 2-iPr)Ph |
| 551 | — | -(2,5-DiMe)Ph |
| 552 | — | -(2,5-DiEt)Ph |
| 553 | —CH₂—O—C(=O)— | -(2-Me)Ph |
| 554 | — | -[1-(4-ClPhenyl)]cyclopropyl |
| 555 | — | -[1-(3,4-DiClPhenyl)]cyclopropyl |
| 556 | — | -[1-(4-Methoxyphenyl)]cyclopropyl |
| 557 | —CH₂ | -(1-Methyl)cyclopropyl |
| 558 | — | -[2,2-DiMethyl,3-(2,2'-Dibromoethylene)]cyclopropyl |
| 559 | —CH₂O | —H |
| 560 | — | —Br |
| 561 | — | 4-(1-oxo)Ethyl-Ph |
| 562 | — | 4[1-(2-propenoxyimino)]Ethyl-Ph |
| 563 | — | 4(1-Ethyloxyimino)Ethyl-Ph |
| 564 | — | 4(1-Benzyloxyimino)Ethyl-Ph |
| 565 | — | 4(2-propenoxyimino)Methyl-Ph |
| 566 | — | 4(Ethyloxyimino)Methyl-Ph |
| 567 | — | 4(Benzyloxyimino)Methyl-Ph |

-continued

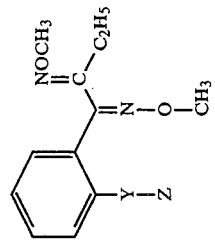

| No. | Link | Substituent | Data |
|---|---|---|---|
| 568 | —CH₂O— | —Ph | |
| 569 | ‖ | -(2-Me)Ph | |
| 570 | ‖ | -(2,4-DiMe)Ph | |
| 571 | ‖ | -(4-Cl, 2-Me)Ph | |
| 572 | ‖ | -(4-Cl)Ph | |
| 573 | ‖ | -(4-tBu, 2 Me)Ph | |
| 574 | ‖ | -(2,3,5-TriMe)Ph | |
| 575 | ‖ | -(4-Cyclohexyl, 2-Me)Ph | |
| 576 | ‖ | -(4-Phenyl)Ph | |
| 577 | ‖ | -(5-Me, 2-iPr)Ph | |
| 578 | ‖ | -(2,5-DiMe)Ph | |
| 579 | ‖ | -(2,5-DiEt)Ph | |
| 580 | —CH₂—O—C(=O)— | -(2-Me)Ph | 73–75° C. |
| 581 | ‖ | -[1-(4-ClPhenyl)]cyclopropyl | |
| 582 | ‖ | -[1-(3,4-DiClPhenyl)]cyclopropyl | |
| 583 | ‖ | -[1-(4-Methoxyphenyl)]cyclopropyl | |
| 584 | ‖ | -(1-Methyl)cyclopropyl | |
| 585 | —CH₂— | -[2,2-DiMethyl,3-(2,2'-Dibromoethylene)]cyclopropyl | |
| 586 | ‖ | —H | |
| 587 | —CH₂O— | —Br | |
| 588 | ‖ | 4-(1-oxo)Ethyl-Ph | |
| 589 | ‖ | 4[1-(2-propenoxyimino)]Ethyl-Ph | |
| 590 | ‖ | 4(1-Ethyloxyimino)Ethyl-Ph | |
| 591 | ‖ | 4(1-Benzyloxyimino)Ethyl-Ph | |
| 592 | ‖ | 4(2-propenoxyimino)Ethyl-Ph | |
| 593 | ‖ | 4(Ethyloxyimino)Methyl-Ph | |
| 594 | ‖ | 4(Benzyloxyimino)Methyl-Ph | |
| 1,595 | —CH₂O— | -2-Methyl-4-(1-methyloxyimino)ethyl-Ph | IR: 1505, 1245, 1052, 1020, 877 |
| 595 | —CH₂O— | —Ph | |
| 596 | ‖ | -(2-Me)Ph | |
| 597 | ‖ | -(2,4-DiMe)Ph | |
| 598 | ‖ | -(4-Cl, 2-Me)Ph | |
| 599 | ‖ | -(4-Cl)Ph | |
| 600 | ‖ | -(4-tBu, 2 Me)Ph | |
| 601 | ‖ | -(2,3,5-TriMe)Ph | |
| 602 | ‖ | -(4-Cyclohexyl, 2-Me)Ph | |
| 603 | ‖ | -(4-Phenyl)Ph | |

-continued

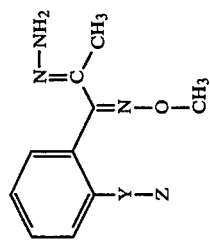

109° C.

| | | | |
|---|---|---|---|
| 604 | | | -(5-Me, 2-iPr)Ph |
| 605 | | | -(2,5-DiMe)Ph |
| 606 | | | -(2,5-DiEt)Ph |
| 607 | —CH₂—O—C(=O) | | -(2-Me)Ph |
| 608 | | | -[1-(4-ClPhenyl)]cyclopropyl |
| 609 | | | -[1-(3,4-DiClPhenyl)]cyclopropyl |
| 610 | | | -[1-(4-Methoxyphenyl)]cyclopropyl |
| 611 | | | -(1-Methyl)cyclopropyl |
| 612 | | | -[2,2-DiMethyl,3-(2,2'-Dibromoethylene)]cyclopropyl |
| 613 | —CH₂ | | —H |
| 614 | —CH₂O | | —Br |
| 615 | | | 4-(1-oxo)Ethyl-Ph |
| 616 | | | 4[1-(2-propenoxyimino)]Ethyl-Ph |
| 617 | | | 4(1-Ethyloxyimino)Ethyl-Ph |
| 618 | | | 4(1-Benzyloxyimino)Ethyl-Ph |
| 619 | | | 4(2-propenoxyimino)Methyl-Ph |
| 620 | | | 4(Ethyloxyimino)Methyl-Ph |
| 621 | | | 4(Benzyloxyimino)Methyl-Ph |
| 622 | —CH₂O | | —Ph |
| 623 | | | -(2-Me)Ph |
| 624 | | | -(2,4-DiMe)Ph |
| 625 | | | -(4-Cl, 2-Me)Ph |
| 626 | | | -(4-Cl)Ph |
| 627 | | | -(4-tBu, 2 Me)Ph |
| 628 | | | -(2,3,5-TriMe)Ph |
| 629 | | | -(4-Cyclohexyl, 2-Me)Ph |
| 630 | | | -(4-Phenyl)Ph |
| 631 | | | -(5-Me, 2-iPr)Ph |
| 632 | | | -(2,5-DiMe)Ph |
| 633 | | | -(2,5-DiEt)Ph |
| 634 | —CH₂—O—C(=O) | | -(2-Me)Ph |
| 635 | | | -[1-(4-ClPhenyl)]cyclopropyl |
| 636 | | | -[1-(3,4-DiClPhenyl)]cyclopropyl |
| 637 | | | -[1-(4-Methoxyphenyl)]cyclopropyl |

-continued

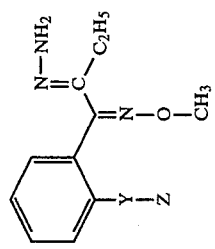

94° C.

| | | |
|---|---|---|
| 638 | — | -(1-Methyl)cyclopropyl |
| 639 | —CH₂— | -[2,2-DiMethyl,3-(2,2'-Dibromoethylene)]cyclopropyl |
| 640 | —CH₂O— | —H |
| 641 | — | 4-(1-oxo)Ethyl-Ph |
| 642 | — | 4[1-(2-propenoxymino)]Ethyl-Ph |
| 643 | — | 4-(1-Ethyloxyimino)Ethyl-Ph |
| 644 | — | 4-(1-Benzyloxyimino)Ethyl-Ph |
| 645 | — | 4-(2-propenoxyimino)Methyl-Ph |
| 646 | — | 4(Ethyloxyimino)Methyl-Ph |
| 647 | — | 4(Benzyloxyimino)Methyl-Ph |
| 648 | —CH₂O— | —Ph |
| 649 | — | -(2-Me)Ph |
| 650 | — | -(2,4-DiMe)Ph |
| 651 | — | -(4-Cl, 2-Me)Ph |
| 652 | — | -(4-Cl)Ph |
| 653 | — | -(4-tBu, 2 Me)Ph |
| 654 | — | -(2,3,5-TriMe)Ph |
| 655 | — | -(4-Cyclohexyl, 2-Me)Ph |
| 656 | — | -(4-Phenyl)Ph |
| 657 | — | -(5-Me, 2-iPr)Ph |
| 658 | — | -(2,5-DiMe)Ph |
| 659 | — | -(2,5-DiEt)Ph |
| 660 | —CH₂—O—C(=O)— | -(2-Me)Ph |
| 661 | — | -[1-(4-ClPhenyl)]cyclopropyl |
| 662 | — | -[1-(3,4-DiClPhenyl)]cyclopropyl |
| 663 | — | -[1-(4-Methoxyphenyl)]cyclopropyl |
| 664 | — | -(1-Methyl)cyclopropyl |
| 665 | —CH₂— | -[2,2-DiMethyl,3-(2,2'-Dibromoethylene)]cyclopropyl |
| 666 | —CH₂O— | —H |
| 667 | — | 4-(1-oxo)Ethyl-Ph |
| 668 | — | 4[1-(2-propenoxymino)]Ethyl-Ph |
| 669 | — | 4-(1-Ethyloxyimino)Ethyl-Ph |
| 670 | — | 4-(1-Benzyloxyimino)Ethyl-Ph |
| 671 | — | 4(2-propenoxyimino)Methyl-Ph |
| 672 | — | 4(Ethyloxyimino)Methyl-Ph |
| 673 | — | 4(Benzyloxyimino)Methyl-Ph |

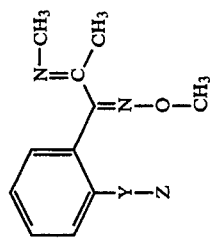
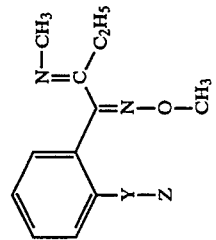

| | | | |
|---|---|---|---|
| 674 | —CH₂O | —Ph | |
| 675 | — | -(2-Me)Ph | |
| 676 | — | -(2,4-DiMe)Ph | |
| 677 | — | -(4-Cl, 2-Me)Ph | |
| 678 | — | -(4-Cl)Ph | |
| 679 | — | -(4-tBu, 2 Me)Ph | |
| 680 | — | -(2,3,5-TriMe)Ph | |
| 681 | — | -(4-Cyclohexyl, 2-Me)Ph | |
| 682 | — | -(4-Phenyl)Ph | |
| 683 | — | -(5-Me, 2-iPr)Ph | |
| 684 | — | -(2,5-DiMe)Ph | |
| 685 | — | -(2,5-DiEt)Ph | |
| 686 | —CH₂—O—C(=O)— | -(2-Me)Ph | |
| 687 | — | -[1-(4-ClPhenyl)]cyclopropyl | |
| 688 | — | -[1-(3,4-DiClPhenyl)]cyclopropyl | |
| 689 | — | -[1-(4-Methoxyphenyl)]cyclopropyl | |
| 690 | — | -(1-Methyl)cyclopropyl | |
| 691 | —CH₂ | -[2,2-DiMethyl,3-(2,2′-Dibromoethylene)cyclopropyl | |
| 692 | —CH₂O | —H | |
| 693 | — | —Br | |
| 694 | — | 4-(1-oxo)Ethyl-Ph | 102–104° C. |
| 695 | — | 4[1-(2-propenoxyimino)]Ethyl-Ph | |
| 696 | — | 4(1-Ethyloxyimino)Ethyl-Ph | |
| 697 | — | 4(1-Benzyloxyimino)Ethyl-Ph | |
| 698 | — | 4(2-propenoxyimino)Methyl-Ph | |
| 699 | — | 4(Ethyloxyimino)Methyl-Ph | |
| 700 | — | 4(Benzyloxyimino)Methyl-Ph | |

-continued

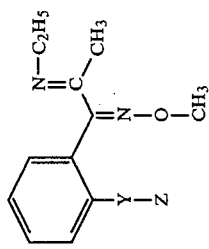

IR: 1495, 1241, 1069, 1010, 750

| | | |
|---|---|---|
| 701 | —CH₂O | —Ph |
| 702 | — | -(2-Me)Ph |
| 703 | — | -(2,4-DiMe)Ph |
| 704 | — | -(4-Cl, 2-Me)Ph |
| 705 | — | -(4-Cl)Ph |
| 706 | — | -(4-tBu, 2 Me)Ph |
| 707 | — | -(2,3,5-TriMe)Ph |
| 708 | — | -(4-Cyclohexyl, 2-Me)Ph |
| 709 | — | -(4-Phenyl)Ph |
| 710 | — | -(5-Me, 2-iPr)Ph |
| 711 | — | -(2,5-DiMe)Ph |
| 712 | — | -(2,5-DiEt)Ph |
| 713 | —CH₂—O—C(=O) | -(2-Me)Ph |
| 714 | — | -[1-(4-ClPhenyl)]cyclopropyl |
| 715 | — | -[1-(3,4-DiClPhenyl)]cyclopropyl |
| 716 | — | -[1-(4-Methoxyphenyl)]cyclopropyl |
| 717 | — | -(1-Methyl)cyclopropyl |
| 718 | — | -[2,2-DiMethyl,3-(2,2'-Dibromoethylene)]cyclopropyl |
| 719 | —CH₂ | —H |
| 720 | —CH₂O | —Br |
| 721 | — | 4-(1-oxo)Ethyl-Ph |
| 722 | — | 4[1-(2-propenoxyimino)Ethyl-Ph |
| 723 | — | 4(1-Ethyloxyimino)Ethyl-Ph |
| 724 | — | 4(1-Benzyloxyimino)Ethyl-Ph |
| 725 | — | 4(2-propenoxyimino)Methyl-Ph |
| 726 | — | 4(Ethyloxyimino)Methyl-Ph |
| 727 | — | 4(Benzyloxyimino)Methyl-Ph |
| 728 | —CH₂O | —Ph |
| 729 | — | -(2-Me)Ph |
| 730 | — | -(2,4-DiMe)Ph |
| 731 | — | -(4-Cl, 2-Me)Ph |
| 732 | — | -(4-Cl)Ph |
| 733 | — | -(4-tBu, 2 Me)Ph |
| 734 | — | -(2,3,5-TriMe)Ph |
| 735 | — | -(4-Cyclohexyl, 2-Me)Ph |
| 736 | — | -(4-Phenyl)Ph |
| 737 | — | -(5-Me, 2-iPr)Ph |

-continued

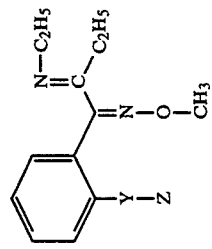

IR: 1495, 1242, 1051, 1028, 750

| # | | |
|---|---|---|
| 738 | — | -(2,5-DiMe)Ph |
| 739 | — | -(2,5-DiEt)Ph |
| 740 | —CH₂—O—C(=O) | -(2-Me)Ph |
| 741 | — | -[1-(4-ClPhenyl)]cyclopropyl |
| 742 | — | -[1-(3,4-DiClPhenyl)]cyclopropyl |
| 743 | — | -[1-(4-Methoxyphenyl)]cyclopropyl |
| 744 | — | -(1-Methyl)cyclopropyl |
| 745 | — | -[2,2-DiMethyl,3-(2,2'-Dibromoethylene)]cyclopropyl |
| 746 | —CH₂ | —H |
| 747 | —CH₂O | —Br |
| 748 | — | 4-(1-oxo)Ethyl-Ph |
| 749 | — | 4[1-(2-propenoxyimino)]Ethyl-Ph |
| 750 | — | 4(1-Ethyloxyimino)Ethyl-Ph |
| 751 | — | 4(1-Benzyloxyimino)Ethyl-Ph |
| 752 | — | 4(2-propenoxyimino)Methyl-Ph |
| 753 | — | 4(Ethyloxyimino)Methyl-Ph |
| 754 | — | 4(Benzyloxyimino)Methyl-Ph |
| 755 | —CH₂O | —Ph |
| 756 | — | -(2-Me)Ph |
| 757 | — | -(2,4-DiMe)Ph |
| 758 | — | -(4-Cl, 2-Me)Ph |
| 759 | — | -(4-Cl)Ph |
| 760 | — | -(4-tBu, 2 Me)Ph |
| 761 | — | -(2,3,5-TriMe)Ph |
| 762 | — | -(4-Cyclohexyl, 2-Me)Ph |
| 763 | — | -(4-Phenyl)Ph |
| 764 | — | -(5-Me, 2-iPr)Ph |
| 765 | — | -(2,5-DiMe)Ph |
| 766 | — | -(2,5-DiEt)Ph |
| 767 | —CH₂—O—C(=O) | -(2-Me)Ph |
| 768 | — | -[1-(4-ClPhenyl)]cyclopropyl |
| 769 | — | -[1-(3,4-DiClPhenyl)]cyclopropyl |
| 770 | — | -[1-(4-Methoxyphenyl)]cyclopropyl |
| 771 | — | -(1-Methyl)cyclopropyl |

-continued

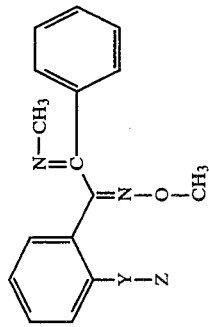

| No. | Y | Z |
|---|---|---|
| 772 | —CH₂— | -[2,2-DiMethyl,3-(2,2'-Dibromoethylene)]cyclopropyl |
| 773 | — | —H |
| 774 | —CH₂O— | —Br |
| 775 | — | 4-(1-oxo)Ethyl-Ph |
| 776 | — | 4[1-(2-propenoxyimino)]Ethyl-Ph |
| 777 | — | 4(1-Ethyloxyimino)Ethyl-Ph |
| 778 | — | 4(1-Benzyloxyimino)Ethyl-Ph |
| 779 | — | 4(2-propenoxyimino)Methyl-Ph |
| 780 | — | 4(Ethyloxyimino)Methyl-Ph |
| 781 | — | 4(Benzyloxyimino)Methyl-Ph |
| 782 | —CH₂O— | —Ph |
| 783 | — | -(2-Me)Ph |
| 784 | — | -(2,4-DiMe)Ph |
| 785 | — | -(4-Cl, 2-Me)Ph |
| 786 | — | -(4-Cl)Ph |
| 787 | — | -(4-tBu, 2 Me)Ph |
| 788 | — | -(2,3,5-TriMe)Ph |
| 789 | — | -(4-Cyclohexyl, 2-Me)Ph |
| 790 | — | -(4-Phenyl)Ph |
| 791 | — | -(5-Me, 2-iPr)Ph |
| 792 | — | -(2,5-DiMe)Ph |
| 793 | — | -(2,5-DiEt)Ph |
| 794 | —CH₂—O—C(=O)— | -(2-Me)Ph |
| 795 | — | -[1-(4-ClPhenyl)]cyclopropyl |
| 796 | — | -[1-(3,4-DiClPhenyl)]cyclopropyl |
| 797 | — | -[1-(4-Methoxyphenyl)]cyclopropyl |
| 798 | — | -(1-Methyl)cyclopropyl |
| 799 | — | -[2,2-DiMethyl,3-(2,2'-Dibromoethylene)]cyclopropyl |
| 800 | —CH₂— | —H |
| 801 | —CH₂O— | —Br |
| 802 | — | 4-(1-oxo)Ethyl-Ph |
| 803 | — | 4[1-(2-propenoxyimino)]Ethyl-Ph |
| 804 | — | 4(1-Ethyloxyimino)Ethyl-Ph |
| 805 | — | 4(1-Benzyloxyimino)Ethyl-Ph |
| 806 | — | 4(2-propenoxyimino)Methyl-Ph |
| 807 | — | 4(Ethyloxyimino)Methyl-Ph |
| 808 | — | 4(Benzyloxyimino)Methyl-Ph |

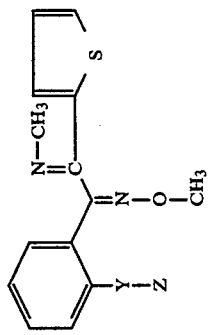
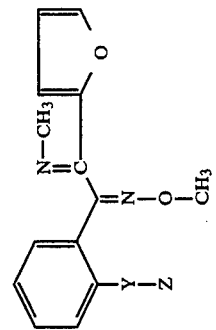

| | | | |
|---|---|---|---|
| 809 | —CH₂O | | —Ph |
| 810 | — | | -(2-Me)Ph |
| 811 | — | | -(2,4-DiMe)Ph |
| 812 | — | | -(4-Cl, 2-Me)Ph |
| 813 | — | | -(4-Cl)Ph |
| 814 | — | | -(4-tBu, 2-Me)Ph |
| 815 | — | | -(2,3,5-TriMe)Ph |
| 816 | — | | -(4-Cyclohexyl, 2-Me)Ph |
| 817 | — | | -(4-Phenyl)Ph |
| 818 | — | | -(5-Me, 2-iPr)Ph |
| 819 | — | | -(2,5-DiMe)Ph |
| 820 | — | | -(2,5-DiEt)Ph |
| 821 | —CH₂—O—C(=O) | | -(2-Me)Ph |
| 822 | — | | -[1-(4-ClPhenyl)]cyclopropyl |
| 823 | — | | -[1-(3,4-DiClPhenyl)]cyclopropyl |
| 824 | — | | -[1-(4-Methoxyphenyl)]cyclopropyl |
| 825 | — | | -(1-Methyl)cyclopropyl |
| 826 | —CH₂ | | -[2,2-DiMethyl,3-(2,2'-Dibromoethylene)]cyclopropyl |
| 827 | — | | —H |
| 828 | — | | —Br |
| 829 | —CH₂O | | -4-(1-oxo)Ethyl-Ph |
| 830 | — | | -4[1-(2-propenoxyimino)]Ethyl-Ph |
| 831 | — | | -4(1-Ethyloxyimino)Ethyl-Ph |
| 832 | — | | -4(1-Benzyloxyimino)Ethyl-Ph |
| 833 | — | | -4(2-propenoxyimino)Methyl-Ph |
| 834 | — | | -4(Ethyloxyimino)Methyl-Ph |
| 835 | — | | -4(Benzyloxyimino)Methyl-Ph |

-continued

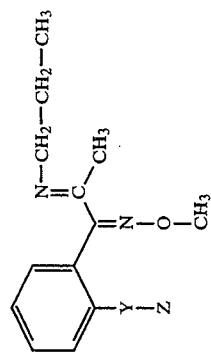

| | | | |
|---|---|---|---|
| 836 | —CH$_2$O | —Ph | |
| 837 | — | -(2-Me)Ph | |
| 838 | — | -(2,4-DiMe)Ph | |
| 839 | — | -(4-Cl, 2-Me)Ph | |
| 840 | — | -(4-Cl)Ph | |
| 841 | — | -(4-tBu, 2 Me)Ph | |
| 842 | — | -(2,3,5-TriMe)Ph | |
| 843 | — | -(4-Cyclohexyl, 2-Me)Ph | |
| 844 | — | -(4-Phenyl)Ph | |
| 845 | — | -(5-Me, 2-iPr)Ph | |
| 846 | — | -(2,5-DiMe)Ph | |
| 847 | — | -(2,5-DiEt)Ph | |
| 848 | —CH$_2$—O—C(O)= | -(2-Me)Ph | |
| 849 | — | -[1-(4-ClPhenyl)]cyclopropyl | |
| 850 | — | -[1-(3,4-DiClPhenyl)]cyclopropyl | |
| 851 | — | -[1-(4-Methoxyphenyl)]cyclopropyl | |
| 852 | — | -(1-Methyl)cyclopropyl | |
| 853 | —CH$_2$ | -[2,2-DiMethyl,3-(2,2'-Dibromoethylene)]cyclopropyl | |
| 854 | —CH$_2$O | —H | |
| 855 | — | —Br | |
| 856 | — | 4-(1-oxo)Ethyl-Ph | |
| 857 | — | 4[1-(2-propenoxyimino)Ethyl-Ph | |
| 858 | — | 4(1-Ethyloxyimino)Ethyl-Ph | |
| 859 | — | 4(1-Benzyloxyimino)Ethyl-Ph | |
| 860 | — | 4(2-propenoxyimino)Methyl-Ph | |
| 861 | — | 4(Ethyloxyimino)Methyl-Ph | |
| 862 | — | 4(Benzyloxyimino)Methyl-Ph | |
| 863 | —CH$_2$O | —Ph | NMR: 7.55–6.70(m,8H); 4.90(s,2H); 3.95(s,3H); 3.35 (t,2H); 2.30(s,3H); 2.15(s,3H); 1.55(m,2H); 0.85(t,3H) ppm |
| 864 | — | -(2-Me)Ph | |
| 865 | — | -(2,4-DiMe)Ph | |
| 866 | — | -(4-Cl, 2-Me)Ph | |
| 867 | — | -(4-Cl)Ph | |
| 868 | — | -(4-tBu, 2 Me)Ph | |
| 869 | — | -(2,3,5-TriMe)Ph | |
| 870 | — | -(4-Cyclohexyl, 2-Me)Ph | |

-continued

| | | |
|---|---|---|
| 871 | — | -(4-Phenyl)Ph |
| 872 | — | -(5-Me, 2-iPr)Ph |
| 873 | — | -(2,5-DiMe)Ph |
| 874 | — | -(2,5-DiEt)Ph |
| 875 | —CH$_2$—O—C(=O)— | -(2-Me)Ph |

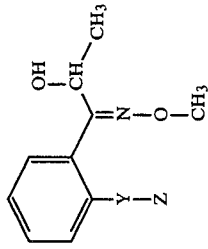

| # | | Y | Z |
|---|---|---|---|
| 876 | — | — | -[1-(4-ClPhenyl)]cyclopropyl |
| 877 | — | — | -[1-(3,4-DiClPhenyl)]cyclopropyl |
| 878 | — | — | -[1-(4-Methoxyphenyl)]cyclopropyl |
| 879 | — | — | -(1-Methyl)cyclopropyl |
| 880 | —CH₂ | — | -[2,2-DiMethyl,3-(2,2'-Dibromoethylene)]cyclopropyl |
| 881 | —CH₂O | — | —H |
| 882 | — | — | —Br |
| 883 | — | — | 4-(1-oxo)Ethyl-Ph |
| 884 | — | — | 4[1-(2-propenoxyimino)]Ethyl-Ph |
| 885 | — | — | 4(1-Ethyloxyimino)Ethyl-Ph |
| 886 | — | — | 4(1-Benzyloxyimino)Ethyl-Ph |
| 887 | — | — | 4(2-propenoxyimino)Methyl-Ph |
| 888 | — | — | 4(Ethyloxyimino)Methyl-Ph |
| 889 | — | — | 4(Benzyloxyimino)Methyl-Ph |
| 890 | —CH₂O | — | —Ph |
| 891 | — | — | -(2-Me)Ph |
| 892 | — | — | -2,4-DiMe)Ph |
| 893 | — | — | -(4-Cl, 2-Me)Ph |
| 894 | — | — | -(4-Cl)Ph |
| 895 | — | — | -(4-tBu, 2 Me)Ph |
| 896 | — | — | -2,3,5-TriMe)Ph |
| 897 | — | — | -(4-Cyclohexyl, 2-Me)Ph |
| 898 | — | — | -(4-Phenyl)Ph |
| 899 | — | — | -(5-Me, 2-iPr)Ph |
| 900 | — | — | -(2,5-DiMe)Ph |
| 901 | — | — | -(2,5-DiEt)Ph |
| 902 | —CH₂—O—C(=O)— | | -(2-Me)Ph |
| 903 | — | — | -[1-(4-ClPhenyl)]cyclopropyl |
| 904 | — | — | -[1-(3,4-DiClPhenyl)]cyclopropyl |
| 905 | — | — | -[1-(4-Methoxyphenyl)]cyclopropyl |
| 906 | — | — | -(1-Methyl)cyclopropyl |
| 907 | —CH₂ | — | -[2,2-DiMethyl,3-(2,2'-Dibromoethylene)]cyclopropyl |
| 908 | —CH₂O | — | —H |
| 909 | — | — | —Br |
| 910 | — | — | 4-(1-oxo)Ethyl-Ph |
| 911 | — | — | 4[1-(2-propenoxyimino)]Ethyl-Ph |
| 912 | — | — | 4(1-Ethyloxyimino)Ethyl-Ph |
| 913 | — | — | 4(1-Benzyloxyimino)Ethyl-Ph |

-continued

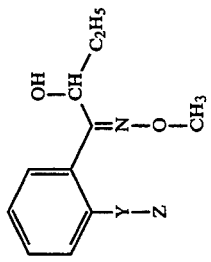

| | | | |
|---|---|---|---|
| 914 | — | -4(2-propenoxyimino)Methyl-Ph | |
| 915 | — | -4(Ethyloxyimino)Methyl-Ph | |
| 916 | — | -4(Benzyloxyimino)Methyl-Ph | |
| 917 | —CH₂O— | —Ph | |
| 918 | — | -(2-Me)Ph | |
| 920 | — | -(2,4-DiMe)Ph | |
| 921 | — | -(4-Cl, 2-Me)Ph | |
| 922 | — | -(4-Cl)Ph | |
| 923 | — | -(4-tBu, 2 Me)Ph | |
| 924 | — | -(2,3,5-TriMe)Ph | |
| 925 | — | -(4-Cyclohexyl, 2-Me)Ph | |
| 926 | — | -(4-Phenyl)Ph | |
| 927 | — | -(5-Me, 2-iPr)Ph | |
| 928 | — | -(2,5-DiMe)Ph | |
| 929 | — | -(2,5-DiEt)Ph | |
| 930 | —CH₂—O—C(=O)— | -(2-Me)Ph | |
| 931 | — | -[1-(4-ClPhenyl)]cyclopropyl | |
| 932 | — | -[1-(3,4-DiClPhenyl)]cyclopropyl | |
| 933 | — | -[1-(4-Methoxyphenyl)]cyclopropyl | |
| 934 | — | -(1-Methyl)cyclopropyl | |
| 935 | — | -[2,2-DiMethyl,3-(2,2'-Dibromoethylene)]cyclopropyl | |
| 936 | —CH₂— | —H | |
| 937 | —CH₂O— | —Br | |
| 938 | — | 4-(1-oxo)Ethyl-Ph | |
| 939 | — | 4[1-(2-propenoxyimino)]Ethyl-Ph | |
| 940 | — | 4(1-Ethyloxyimino)Ethyl-Ph | |
| 941 | — | 4(1-Benzyloxyimino)Ethyl-Ph | |
| 942 | — | 4(2-propenoxyimino)Methyl-Ph | |
| 943 | — | 4(Ethyloxyimino)Methyl-Ph | |
| 944 | — | 4(Benzyloxyimino)Methyl-Ph | NMR: 7.70–6.70(m,8H); 4.95(m,2H); 4.45(m,1H); 3.90(s,3H); 2.30(s,3H); 1.60(m,2H); 1.00(t,3H) ppm |

-continued

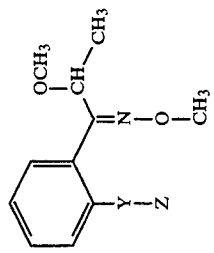 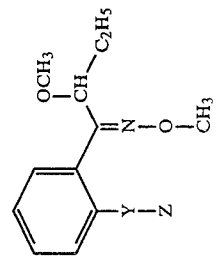

| | | | |
|---|---|---|---|
| 945 | —CH₂O— | — | —Ph |
| 946 | | — | -(2-Me)Ph |
| 947 | | — | -(2,4-DiMe)Ph |
| 948 | | — | -(4-Cl, 2-Me)Ph |
| 949 | | — | -(4-Cl)Ph |
| 950 | | — | -(4-tBu, 2 Me)Ph |
| 951 | | — | -(2,3,5-TriMe)Ph |
| 952 | | — | -(4-Cyclohexyl, 2-Me)Ph |
| 953 | | — | -(4-Phenyl)Ph |
| 954 | | — | -(5-Me, 2-iPr)Ph |
| 955 | | — | -(2,5-DiMe)Ph |
| 956 | | — | -(2,5-DiEt)Ph |
| 957 | —CH₂—O—C(=O)— | — | -(2-Me)Ph |
| 958 | | — | -[1-(4-ClPhenyl)]cyclopropyl |
| 959 | | — | -[1-(3,4-DiClPhenyl)]cyclopropyl |
| 960 | | — | -[1-(4-Methoxyphenyl)]cyclopropyl |
| 961 | | — | -(1-Methyl)cyclopropyl |
| 962 | | — | -[2,2-DiMethyl,3-(2,2′-Dibromoethylene)]cyclopropyl |
| 963 | —CH₂— | — | —H |
| 964 | —CH₂O— | — | —Br |
| 965 | | — | 4-(1-oxo)Ethyl-Ph |
| 966 | | — | 4[1-(2-propenoxyimino)]Ethyl-Ph |
| 967 | | — | 4(1-Ethyloxyimino)Ethyl-Ph |
| 968 | | — | 4(1-Benzyloxyimino)Ethyl-Ph |
| 969 | | — | 4(2-propenoxyimino)Methyl-Ph |
| 970 | | — | 4(Ethyloxyimino)Methyl-Ph |
| 971 | | — | 4(Benzyloxyimino)Methyl-Ph |

-continued

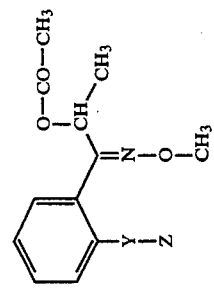

| # | | | | NMR |
|---|---|---|---|---|
| 972 | —CH₂O | — | —Ph | NMR: 7.70-6.75(m,8H);5.50-4.80(m,2H);3.85(m,4H); 3.45(s,3H);2.30(s,3H);1.75-1.35(m,2H); 0.95(t,3H)ppm |
| 973 | | | -(2-Me)Ph | |
| 974 | | | -(2,4-DiMe)Ph | |
| 975 | | | -(4-Cl, 2-Me)Ph | |
| 976 | | | -(4-Cl)Ph | |
| 977 | | | -(4-tBu, 2 Me)Ph | |
| 978 | | | -(2,3,5-TriMe)Ph | |
| 979 | | | -(4-Cyclohexyl, 2-Me)Ph | |
| 980 | | | -(4-Phenyl)Ph | |
| 981 | | | -(5-Me, 2-iPr)Ph | |
| 982 | | | -(2,5-DiMe)Ph | |
| 983 | | | -(2,5-DiEt)Ph | |
| 984 | —CH₂—O—C(=O)— | | -(2-Me)Ph | |
| 985 | | | -[1-(4-ClPhenyl)]cyclopropyl | |
| 986 | | | -[1-(3,4-DiClPhenyl)]cyclopropyl | |
| 987 | | | -[1-(4-Methoxyphenyl)]cyclopropyl | |
| 988 | | | -(1-Methyl)cyclopropyl | |
| 989 | —CH₂ | | -[2,2-DiMethyl,3-(2,2'-Dibromoethylene)]cyclopropyl | |
| 990 | —CH₂O | | —H | |
| 991 | | | —Br | |
| 992 | | | -4-(1-oxo)Ethyl-Ph | |
| 993 | | | -4[1-(2-propenoxyimino)]Ethyl-Ph | |
| 994 | | | -4(1-Ethyloxyimino)Ethyl-Ph | |
| 995 | | | -4(1-Benzyloxyimino)Ethyl-Ph | |
| 996 | | | -4(2-propenoxyimino)Methyl-Ph | |
| 997 | | | -4(Ethyloxyimino)Methyl-Ph | |
| 998 | | | -4(Benzyloxyimino)Methyl-Ph | |
| 998 | —CH₂O | | —Ph | NMR: 7.70-6.70(m,8H); isomer A 5.75 (q,1H); isomer B 5.65 (q,1H); 4.95 (m,2H); 3.85 (m,3H); 2.30 (s,3H); 2.00 (m,3H); 1.45 (m,3H) ppm |
| 999 | | | -(2-Me)Ph | |
| 1000 | | | -(2,4-DiMe)Ph | |
| 1001 | | | -(4-Cl, 2-Me)Ph | |
| 1002 | | | -(4-Cl)Ph | |
| 1003 | | | -(4-tBu, 2 Me)Ph | |
| 1004 | | | -(2,3,5-TriMe)Ph | |

-continued

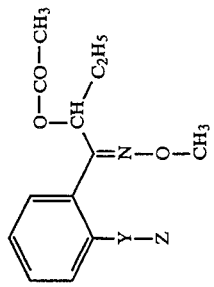

| | | | |
|---|---|---|---|
| 1005 | — | -(4-Cyclohexyl, 2-Me)Ph | |
| 1006 | — | -(4-Phenyl)Ph | |
| 1007 | — | -(5-Me, 2-iPr)Ph | |
| 1008 | — | -(2,5-DiMe)Ph | |
| 1009 | — | -(2,5-DiEt)Ph | |
| 1010 | —CH₂—O—C(=O)— | -(2-Me)Ph | |
| 1011 | — | -[1-(4-ClPhenyl)]cyclopropyl | |
| 1012 | — | -[1-(3,4-DiClPhenyl)]cyclopropyl | |
| 1013 | — | -[1-(4-Methoxyphenyl)]cyclopropyl | |
| 1014 | — | -(1-Methyl)cyclopropyl | |
| 1015 | — | -[2,2-DiMethyl,3-(2,2'-Dibromoethylene)]cyclopropyl | |
| 1016 | —CH₂— | —H | |
| 1017 | —CH₂O— | —Br | |
| 1018 | — | 4-(1-oxo)Ethyl-Ph | |
| 1019 | — | 4{1-(2-propenoxyimino)]Ethyl-Ph | |
| 1020 | — | 4-(1-Ethyloxyimino)Ethyl-Ph | |
| 1021 | — | 4-(1-Benzyloxyimino)Ethyl-Ph | |
| 1022 | — | 4-(2-propenoxyimino)Methyl-Ph | |
| 1023 | — | 4-(Ethyloxyimino)Methyl-Ph | |
| 1024 | — | 4-(Benzyloxyimino)Methyl-Ph | |
| 1025 | —CH₂O— | —Ph | |
| 1026 | — | -(2-Me)Ph | NMR: 7.70–6.75(m,8H); isomer A 5.60 (m,1H); isomer B 5.45 (m,1H); 4.95 (m,2H); 3.85 (m,2H); 2.30 (s,3H); 2.10–1.65 (m,5H); 0.95 (t,3H) ppm |
| 1027 | — | -(2,4-DiMe)Ph | |
| 1028 | — | -(4-Cl, 2-Me)Ph | |
| 1029 | — | -(4-Cl)Ph | |
| 1030 | — | -(4-tBu, 2-Me)Ph | |
| 1031 | — | -(2,3,5-TriMe)Ph | |
| 1032 | — | -(4-Cyclohexyl, 2-Me)Ph | |
| 1033 | — | -(4-Pheny)Ph | |
| 1034 | — | -(5-Me, 2-iPr)Ph | |
| 1035 | — | -(2,5-DiMe)Ph | |
| 1036 | — | -(2,5-DiEt)Ph | |
| 1037 | —CH₂—O—C(=O)— | -(2-Me)Ph | |

-continued

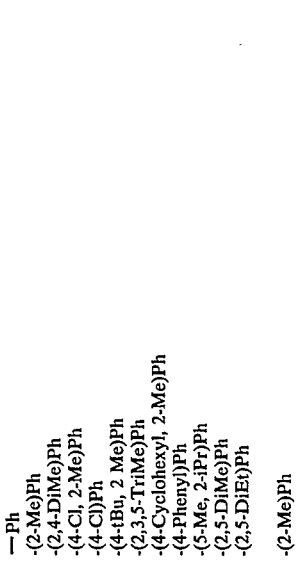

IR: 1495, 1242, 1230, 1066, 752

| | Y | Z |
|---|---|---|
| 1038 | — | -[1-(4-ClPhenyl)]cyclopropyl |
| 1039 | — | -[1-(3,4-DiClPhenyl)]cyclopropyl |
| 1040 | — | -[1-(4-Methoxyphenyl)]cyclopropyl |
| 1041 | — | -(1-Methyl)cyclopropyl |
| 1042 | —CH₂ | -[2,2-DiMethyl,3-(2,2'-Dibromoethylene)]cyclopropyl |
| 1043 | —CH₂O | —H |
| 1044 | — | —Br |
| 1045 | — | 4-(1-oxo)Ethyl-Ph |
| 1046 | — | 4[1-(2-propenoxyimino)]Ethyl-Ph |
| 1047 | — | 4(1-Ethyloxyimino)Ethyl-Ph |
| 1048 | — | 4(1-Benzyloxyimino)Ethyl-Ph |
| 1049 | — | 4(2-propenoxyimino)Methyl-Ph |
| 1050 | — | 4(Ethyloxyimino)Methyl-Ph |
| 1051 | — | 4(Benzyloxyimino)Methyl-Ph |
| 1052 | —CH₂O | -Ph |
| 1053 | — | -(2-Me)Ph |
| 1054 | — | -(2,4-DiMe)Ph |
| 1055 | — | -(4-Cl, 2-Me)Ph |
| 1056 | — | -(4-Cl)Ph |
| 1057 | — | -(4-tBu, 2 Me)Ph |
| 1058 | — | -(2,3,5-TriMe)Ph |
| 1059 | — | -(4-Cyclohexyl, 2-Me)Ph |
| 1060 | — | -(4-Phenyl)Ph |
| 1061 | — | -(5-Me, 2-iPr)Ph |
| 1062 | — | -(2,5-DiMe)Ph |
| 1063 | — | -(2,5-DiEt)Ph |
| 1064 | —CH₂—O—C(=O) | -(2-Me)Ph |
| 1065 | — | -[1-(4-ClPhenyl)]cyclopropyl |
| 1066 | — | -[1-(3,4-DiClPhenyl)]cyclopropyl |
| 1067 | — | -[1-(4-Methoxyphenyl)]cyclopropyl |
| 1068 | — | -(1-Methyl)cyclopropyl |
| 1069 | —CH₂ | -[2,2-DiMethyl,3-(2,2'-Dibromoethylene)]cyclopropyl |
| 1070 | —CH₂O | —H |
| 1071 | — | —Br |
| 1072 | — | 4-(1-oxo)Ethyl-Ph |
| 1073 | — | 4[1-(2-propenoxyimino)]Ethyl-Ph |
| 1074 | — | 4(1-Ethyloxyimino)Ethyl-Ph |

-continued

| | |
|---|---|
| 1075 | —4(1-Benzyloxyimino)Ethyl-Ph |
| 1076 | —4(2-propenoxyimino)Methyl-Ph |
| 1077 | —4(Ethyloxyimino)Methyl-Ph |
| 1078 | —4(Benzyloxyimino)Methyl-Ph |

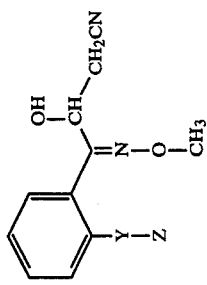
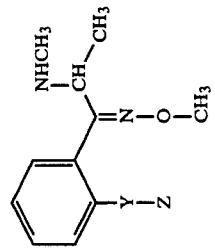

IR: 1495, 1240, 1052, 1020, 753

| | | | |
|---|---|---|---|
| 1079 | —CH₂O— | — | —Ph |
| 1080 | — | — | -(2-Me)Ph |
| 1081 | — | — | -(2,4-DiMe)Ph |
| 1082 | — | — | -(4-Cl, 2-Me)Ph |
| 1083 | — | — | -(4-Cl)Ph |
| 1084 | — | — | -(4-tBu, 2-Me)Ph |
| 1085 | — | — | -(2,3,5-TriMe)Ph |
| 1086 | — | — | -(4-Cyclohexyl, 2-Me)Ph |
| 1087 | — | — | -(4-Phenyl)Ph |
| 1088 | — | — | -(5-Me, 2-iPr)Ph |
| 1089 | — | — | -(2,5-DiMe)Ph |
| 1090 | — | — | -(2,5-DiEt)Ph |
| 1091 | —CH₂—O—C(=O)— | — | -(2-Me)Ph |
| 1092 | — | — | -[1-(4-ClPhenyl)]cyclopropyl |
| 1093 | — | — | -[1-(3,4-DiClPhenyl)]cyclopropyl |
| 1094 | — | — | -[1-(4-Methoxyphenyl)]cyclopropyl |
| 1095 | — | — | -(1-Methyl)cyclopropyl |
| 1096 | — | — | -[2,2-DiMethyl,3-(2,2'-Dibromoethylene)]cyclopropyl |
| 1097 | —CH₂— | — | —H |
| 1098 | —CH₂O— | — | —Br |
| 1099 | — | — | 4-(1-oxo)Ethyl-Ph |
| 1100 | — | — | 4[1-(2-propenoxyimino)]Ethyl-Ph |
| 1101 | — | — | 4(1-Ethyloxyimino)Ethyl-Ph |
| 1102 | — | — | 4(1-Benzyloxyimino)Ethyl-Ph |
| 1103 | — | — | 3(2-propenoxyimino)Methyl-Ph |
| 1104 | — | — | 4(Ethyloxyimino)Methyl-Ph |
| 1105 | — | — | 4(Benzyloxyimino)Methyl-Ph |

-continued

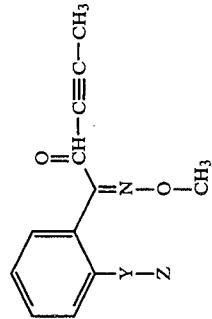

| | | | NMR |
|---|---|---|---|
| 1106 | —CH$_2$O— | —Ph | NMR: 7.70–6.75(m,8H); 4.95 (m,2H); 3.85 (s,3H); 3.50(m,1H); 2.50(m,3H); 2.30(s,3H); 1.1(m,3H) ppm |
| 1107 | — | -(2-Me)Ph | |
| 1108 | — | -(2,4-DiMe)Ph | |
| 1109 | — | -(4-Cl, 2-Me)Ph | |
| 1110 | — | -(4-Cl)Ph | |
| 1111 | — | -(4-tBu, 2 Me)Ph | |
| 1112 | — | -(2,3,5-TriMe)Ph | |
| 1113 | — | -(4-Cyclohexyl, 2-Me)Ph | |
| 1114 | — | -(4-Pheny])Ph | |
| 1115 | — | -(5-Me, 2-iPr)Ph | |
| 1116 | — | -(2,5-DiMe)Ph | |
| 1117 | — | -(2,5-DiEt)Ph | |
| 1118 | —CH$_2$—O—C(=O)— | -(2-Me)Ph | |
| 1119 | — | -[1-(4-ClPhenyl)]cyclopropyl | |
| 1120 | — | -[1-(3,4-DiClPhenyl)]cyclopropyl | |
| 1121 | — | -[1-(4-Methoxyphenyl)]cyclopropyl | |
| 1122 | — | -(1-Methyl)cyclopropyl | |
| 1123 | —CH$_2$— | -[2,2-DiMethyl,3-(2,2'-Dibromoethylene)cyclopropyl | |
| 1124 | —CH$_2$O— | —H | |
| 1125 | — | —Br | |
| 1126 | — | 4-(1-oxo)Ethyl-Ph | |
| 1127 | — | 4[1-(2-propenoxyimino)]Ethyl-Ph | |
| 1128 | — | 4(1-Ethyloxyimino)Ethyl-Ph | |
| 1129 | — | 4(1-Benzyloxyimino)Ethyl-Ph | |
| 1130 | — | 4(2-propenoxyimino)Methyl-Ph | |
| 1131 | — | 4(Ethyloxyimino)Methyl-Ph | |
| 1132 | — | 4(Benzyloxyimino)Methyl-Ph | |
| 1133 | —CH$_2$O— | —Ph | |
| 1134 | — | -(2-Me)Ph | |
| 1135 | — | -(2,4-DiMe)Ph | |
| 1136 | — | -(4-Cl, 2-Me)Ph | |
| 1137 | — | -(4-Cl)Ph | |
| 1138 | — | -(4-tBu, 2 Me)Ph | |
| 1139 | — | -(2,3,5-TriMe)Ph | |
| 1140 | — | -(4-Cyclohexyl, 2-Me)Ph | |
| 1141 | — | -(4-Pheny])Ph | |

-continued

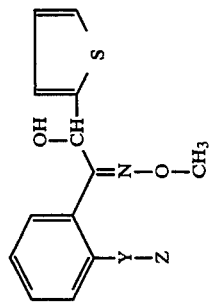

IR: 1494, 1243, 1229, 1021, 751

| | | |
|---|---|---|
| 1142 | — | -(5-Me, 2-iPr)Ph |
| 1143 | — | -(2,5-DiMe)Ph |
| 1144 | — | -(2,5-DiEt)Ph |
| 1145 | —CH₂—O—C(=O)— | -(2-Me)Ph |
| 1146 | — | -[1-(4-ClPhenyl)]cyclopropyl |
| 1147 | — | -[1-(3,4-DiClPhenyl)]cyclopropyl |
| 1148 | — | -[1-(4-Methoxyphenyl)]cyclopropyl |
| 1149 | — | -(1-Methyl)cyclopropyl |
| 1150 | — | -[2,2-DiMethyl,3-(2,2'-Dibromoethylene)]cyclopropyl |
| 1151 | —CH₂— | —H |
| 1152 | —CH₂O— | —Br |
| 1153 | — | 4-(1-oxo)Ethyl-Ph |
| 1154 | — | 4-[1-(2-propenoxyimino)Ethyl-Ph |
| 1155 | — | 4-(1-Ethyloxyimino)Ethyl-Ph |
| 1156 | — | 4-(1-Benzyloxyimino)Ethyl-Ph |
| 1157 | — | 4-(2-propenoxyimino)Methyl-Ph |
| 1158 | — | 4-(Ethyloxyimino)Methyl-Ph |
| 1159 | — | 4-(Benzyloxyimino)Methyl-Ph |
| 1160 | —CH₂O— | —Ph |
| 1161 | — | -(2-Me)Ph |
| 1162 | — | -(2,4-DiMe)Ph |
| 1163 | — | -(4-Cl, 2-Me)Ph |
| 1164 | — | -(4-Cl)Ph |
| 1165 | — | -(4-tBu, 2 Me)Ph |
| 1166 | — | -(2,3,5-TriMe)Ph |
| 1167 | — | -(4-Cyclohexyl, 2-Me)Ph |
| 1168 | — | -(4-Phenyl)Ph |
| 1169 | — | -(5-Me, 2-iPr)Ph |
| 1170 | — | -(2,5-DiMe)Ph |
| 1171 | — | -(2,5-DiEt)Ph |
| 1172 | —CH₂—O—C(=O)— | -(2-Me)Ph |
| 1173 | — | -[1-(4-ClPhenyl)]cyclopropyl |
| 1174 | — | -[1-(3,4-DiClPhenyl)]cyclopropyl |
| 1175 | — | -[1-(4-Methoxyphenyl)]cyclopropyl |

-continued

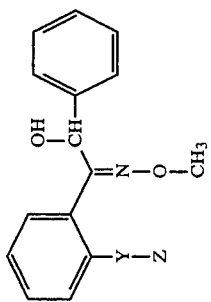

| | | | 1494, 1243, 1229, 1036, 751 |
|---|---|---|---|
| 1176 | — | -(1-Methyl)cyclopropyl | |
| 1177 | —CH₂— | -[2,2-DiMethyl,1,3-(2,2'-Dibromoethylene)]cyclopropyl | |
| 1178 | —CH₂O— | —H | |
| 1179 | — | —Br | |
| 1180 | — | -4-(1-oxo)Ethyl-Ph | |
| 1181 | — | 4[1-(2-propenoxyimino)]Ethyl-Ph | |
| 1182 | — | 4-(1-Ethyloxyimino)Ethyl-Ph | |
| 1183 | — | 4-(1-Benzyloxyimino)Ethyl-Ph | |
| 1184 | — | 4-(2-propenoxyimino)Methyl-Ph | |
| 1185 | — | 4(Ethyloxyimino)Methyl-Ph | |
| 1186 | — | 4(Benzyloxyimino)Methyl-Ph | |
| 1187 | —CH₂O— | —Ph | |
| 1188 | — | -(2-Me)Ph | |
| 1189 | — | -(2,4-DiMe)Ph | |
| 1190 | — | -(2-Cl, 2-Me)Ph | |
| 1191 | — | -(4-Cl)Ph | |
| 1192 | — | -(4-tBu, 2 Me)Ph | |
| 1193 | — | -(2,3,5-TriMe)Ph | |
| 1194 | — | -(4-Cyclohexyl, 2-Me)Ph | |
| 1195 | — | -(4-Phenyl)Ph | |
| 1196 | — | -(5-Me, 2-iPr)Ph | |
| 1197 | — | -(2,5-DiMe)Ph | |
| 1198 | — | -(2,5-DiEt)Ph | |
| 1199 | —CH₂—O—C(=O)— | -(2-Me)Ph | |
| 1200 | — | -[1-(4-ClPhenyl)]cyclopropyl | |
| 1201 | — | -[1-(3,4-DiClPhenyl)]cyclopropyl | |
| 1202 | — | -[1-(4-Methoxyphenyl)]cyclopropyl | |
| 1203 | — | -(1-Methyl)cyclopropyl | |
| 1204 | —CH₂— | -[2,2-DiMethyl,1,3-(2,2'-Dibromoethylene)]cyclopropyl | |
| 1205 | —CH₂O— | —H | |
| 1206 | — | —Br | |
| 1207 | — | -4-(1-oxo)Ethyl-Ph | |
| 1208 | — | 4[1-(2-propenoxyimino)]Ethyl-Ph | |
| 1209 | — | 4-(1-Ethyloxyimino)Ethyl-Ph | |
| 1210 | — | 4-(1-Benzyloxyimino)Ethyl-Ph | |
| 1211 | — | 4-(2-propenoxyimino)Methyl-Ph | |
| 1212 | — | 4(Ethyloxyimino)Methyl-Ph | |
| 1213 | — | 4(Benzyloxyimino)Methyl-Ph | |

| | | | |
|---|---|---|---|
| 1214 | —CH$_2$O | 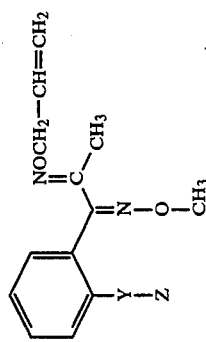 -2-Methyl-4-[1-(2-propen)oxyimino]ethyl-Ph | IR: 1506, 1232, 1066, 1007, 993 |
| 1215 | —CH$_2$O | 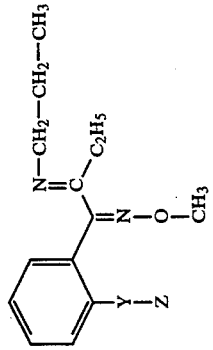 -(2-Me)Ph | IR: 1495, 1242, 1228, 1071, 749 |
| 1216 | —CH$_2$O | 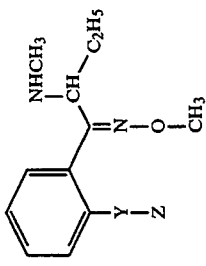 —Ph | IR: 1495, 1241, 1229, 1013, 750 |
| 1217 | — | -(2-Me)Ph | |
| 1218 | — | -(2,4-DiMe)Ph | |
| 1219 | — | -(4-Cl, 2-Me)Ph | |
| 1220 | — | -(4-Cl)Ph | |
| 1221 | — | -(4-tBu, 2 Me)Ph | |
| 1222 | — | -(2,3,5-TriMe)Ph | |
| 1223 | — | -(4-Cyclohexyl, 2-Me)Ph | |
| 1224 | — | -(4-Phenyl)Ph | |
| 1225 | — | -(5-Me, 2-iPr)Ph | |
| 1226 | — | -(2,5-DiMe)Ph | |
| 1227 | — | -(2,5-DiEt)Ph | |

-continued

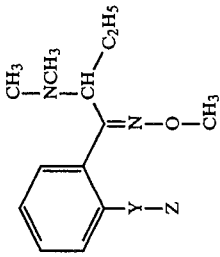

| | | | |
|---|---|---|---|
| 1228 | —CH₂—O—C(=O) | -(2-Me)Ph | |
| 1229 | — | -[1-(4-ClPhenyl)]cyclopropyl | |
| 1230 | — | -[1-(3,4-DiClPhenyl)]cyclopropyl | |
| 1231 | — | -[1-(4-Methoxyphenyl)]cyclopropyl | |
| 1232 | — | -(1-Methyl)cyclopropyl | |
| 1233 | —CH₂— | -[2,2-DiMethyl,3-(2,2'-DiBrom-Ethylen)]cyclopropyl | |
| 1234 | —CH₂O— | —H | |
| 1235 | — | —Br | |
| 1236 | — | 4-(1-oxo)Ethyl-Ph | |
| 1237 | — | 4[1-(2-propenoxyimino)]Ethyl-Ph | |
| 1238 | — | 4(1-Ethyloxyimino)Ethyl-Ph | |
| 1239 | — | 4(1-Benzyloxyimino)Ethyl-Ph | |
| 1240 | — | 4(2-propenoxyimino)Methyl-Ph | |
| 1241 | — | 4(Ethyloxyimino)Methyl-Ph | |
| 1242 | — | 4(Benzyloxyimino)Methyl-Ph | |
| 1243 | —CH₂O— | —Ph | |
| 1244 | — | -(2-Me)Ph | |
| 1245 | — | -(2,4-DiMe)Ph | |
| 1246 | — | -(4-Cl, 2-Me)Ph | |
| 1247 | — | -(4-Cl)Ph | |
| 1248 | — | -(4-tBu, 2 Me)Ph | |
| 1249 | — | -(2,3,5-TriMe)Ph | |
| 1250 | — | -(4-Cyclohexyl, 2-Me)Ph | |
| 1251 | — | -(4-Phenyl)Ph | |
| 1252 | — | -(5-Me, 2-iPr)Ph | |
| 1253 | — | -(2,5-DiMe)Ph | |
| 1254 | — | -(2,5-DiEt)Ph | |
| 1255 | —CH₂—O—C(=O) | -(2-Me)Ph | IR: 1495, 1241, 1228, 1015, 750 |
| 1256 | — | -[1-(4-ClPhenyl)]cyclopropyl | |
| 1257 | — | -[1-(3,4-DiClPhenyl)]cyclopropyl | |
| 1258 | — | -[1-(4-Methoxyphenyl)]cyclopropyl | |
| 1259 | — | -(1-Methyl)cyclopropyl | |
| 1260 | — | -[2,2-DiMethyl,3-(2,2'-Dibromoethylene)]cyclopropyl | |
| 1261 | —CH₂— | —H | |
| 1262 | — | —Br | |

-continued

| | | |
|---|---|---|
| 1263 | —CH₂O | -4-(1-oxo)Ethyl-Ph |
| 1264 | — | -4[1-(2-propenoxyimino)]Ethyl-Ph |
| 1265 | — | -4(1-Ethyloxyimino)Ethyl-Ph |
| 1266 | — | -4(1-Benzyloxyimino)Ethyl-Ph |
| 1267 | — | -4(2-propenoxyimino)Methyl-Ph |
| 1268 | — | -4(Ethyloxyimino)Methyl-Ph |
| 1269 | — | -4(Benzyloxyimino(Methyl-Ph |

TABLE 2

NMR data of selected compounds from Table 1. The chemical shift (4) is given in ppm relative to tetramethylsilane. The solvent is CDCl₃.

| Compound No. | |
|---|---|
| 56 | IR 1745, 1699, 1495, 1242, 1043 |
| 83 | IR 1747, 1699, 1495, 1312, 1033 |
| 272 | IR 1694, 1495, 1462, 1241, 1123 |
| 191 | 0.9S 3H; 1.3S 2H; 1.9S 2H; 2.25S 3H; 3.6S 3H; 4.05S 3H; 4.45S 1H; 4.85S 2H; 6.7–7.75M 8H |
| 137 | 1.4–1.55M 4H; 2.25S 3H; 3.65S 3H; 4.0S 3H; 4.9S 1H; 6.75–7.65M 8H |
| 316 | 1.2T 3H; 2.1S 3H; 3.0Q 2H; 4.0S 3H; 6.95–7.35M 4H |
| 110 | 1.5S 6H; 2.25S 3H; 3.6S 3H; 4.0S 3H; 4.85S 2H; 6.7–7.6M 8H |
| 353 | 0.9T 3H; 1.25–1.65M 4H; 2.2S 3H; 2.9T 2H; 4.0S 3H; 4.85S 2H; 6.7–7.5M 8H |
| 380 | 1.15D 6H; 2.25S 3H; 3.7M 1H; 4.0S 3H; 4.85S 2H; 6.7–7.6M 8H |
| 127 | 1.55A 6H; 2.10S 3H; 3.75S 3H; 3.95S 3H; 7.35–6.90M 4H |
| 128 | 1.55S 6H; 3.75S 3H; 4.00S 3H; 4.30S 2H; 7.55–6.95M 4H |
| 129 | 1.50S 6H; 2.55S 3H; 3.65S 3H; 3.95S 3H; 4.9S 2H; 7.95–6.85M 8H |
| 399 | 1.15D 6H; 2.55S 3H; 3.7Q 1H; 4.05S 3H; 4.85S 2H; 6.8–7.9M 8H |
| 383 | 1.20S 3H; 4.85S 2H; 4.0S 3H; 4.8S 2H; 6.7–7.5M 8H |
| 381 | 1.2D 6H; 2.2D 6H; 3.7M 1H; 4.0S 3H; 4.85S 2H; 6.6–7.55M 7H |
| 382 | 1.2D 6H; 2.2S 3H; 3.7M 1H; 4.0S 3H; 4.85S 2H; 6.6–7.5M 7H |
| 385 | 1.2D 6H; 2.05S 3H; 2.2Dup 6H; 3.7M 1H; 4.0S 3H; 4.8S 2H; 6.6–7.55M 6H |
| 85 | 1.4S 3H; 2.2S 3H; 3.65S 3H; 4.0S 3H; 4.45D 1H; 4.8S 2H; 5.5–7.5M 7H |
| 84 | 1.4D 3H; 2.25D 6H; 3.65S 3H; 4.0S 3H; 4.45D 1H; 4.8S 2H; 6.6–7.55M 7H |
| 88 | 1.4D 3H; 2.1S 3H; 2.25D 6H; 3.65S 3H; 4.0S 3H; 4.45M 1H; 4.8S 2H; 6.45–7.6M 6H |
| 87 | 1.3S 9H; 1.4D 3H; 2.3S 3H; 3.65S 3H; 4.0S 3H; 4.45M 1H; 4.85S 2H; 6.65–7.6M 7H |
| 86 | 1.4D 3H; 3.65S 3H; 4.0S 3H; 4.45D 1H; 4.85S 2H; 6.75–7.55M 8H |
| 91 | 1.25T 6H; 1.4D 3H; 2.2D 3H; 3.3M 1H; 3.65S 3H; 4.0S 3H; 4.45D 1H; 4.8S 2H; 6.55–7.6M 7H |
| 92 | 1.4D 3H; 2.2S 3H; 2.25S 3H; 3.65S 3H; 4.0S 3H; 4.45D 1H; 4.8S 2H; 6.55–7.6M 7H |
| 93 | 1.2T 6H; 1.4D 3H; 2.55Q 4H; 3.65S 3H; 4.0S 3H; 4.45D 1H; 4.8S 2H; 6.5–7.55M 7H |
| 300 | 1.1T 3H; 2.1S 3H; 2.15S 3H; 2.9Q 2H; 4.0S 3H; 4.8S 2H; 6.6–7.55M 7H |
| 301 | 1.1T 3H; 2.15S 3H; 2.9Q 2H; 4.0S 3H; 4.8S 2H; 6.6–7.55M 7H |
| 302 | 1.1T 3H; 2.9Q 2H; 4.0S 3H; 4.8S 2H; 6.75–7.5M 8H |
| 308 | 1.1T 3H; 2.1S 3H; 2.25S 3H; 2.9Q 2H; 4.0S 3H; 4.8S 2H; 6.55–7.55M 7H |
| 304 | 1.1T 3H; 2.05S 3H; 2.2 je 1×S 6H; 2.9Q 2H; 4.0S 3H; 4.8S 2H; 6.45–7.55M 6H |
| 303 | 1.1T 3H; 1.3S 9H; 2.2S 3H; 2.9Q 2H; 4.0S 3H; 4.8S 2H; 6.65–7.55M 7H |
| 307 | 1.1T 3H; 1.15D 6H; 2.25S 3H; 2.9Q 2H; 3.3M 1H; 4.0S 3H; 4.8S 2H; 6.55–7.6M 7H |
| 309 | 1.05–1.2M 9H; 2.55Q 4H; 2.9Q 2H; 4.0S 3H; 4.8S 2H; 6.5–7.5M 7H |
| 434 | 2.1S 3H; 4.0S 3H; 4.95S 2H; 6.8–8.0M 13H |
| 305 | 1.1T 3H; 1.2–1.9M 10H; 2.2S 3H; 2.9Q 2H; 4.0S 3H; 4.8S 2H; 6.6–7.6M 7H |
| 276 | 1.25S 9H; 2.2S 3H; 2.45S 3H; 4.0S 3H; 4.8S 2H; 6.65–7.5M 7H |
| 278 | 1.2–1.85M 10H; 2.2S 3H; 2.45 5 3H; 4.0S 3H; 4.8S 2H; 6.65–7.5M 7H |
| 461 | 2.1S 3H; 4.05S 3H; 4.95S 2H; 6.7–8.05M 11H |
| 386 | 1.05–1.95M 16H; 2.20S. 3H; 2.40M 1H; 3.75M 1H; 4.85S 2H; 6.60–7.80M 7H |
| 313 | 1.2–1.6M 7H; 2.95Q 2H; 3.8S 3H; 4.0S 3H; 4.85S 2H; 6.8–7.4M 8H |
| 315 | 1.1–1.6M 10H; 2.15S 1H; 3.00Q 2H; 4.05S 3H; 4.90M 2H; 6.15D 1H; 7.00–7.60M 4H |
| 440 | 2.15S 3H; 2.3M 5H; 4.0S 3H; 4.95S 2H; 6.6–7.7M 12H |
| 245 | 3.25S 3H; 3.65S 3H; 3.8S 2H; 3.9S 3H; 4.95S 2H; 6.8–7.65M 8H |
| 299 | 1.1T 3H; 2.2S 3H; 2.95Q 2H; 4.0S 3H; 4.85S 2H; 6.6–7.6M 8H |
| 596 | 1.1T 3H; 2.15S 3H; 2.7Q 2H; 3.75S 3H; 3.95S 3H; 4.95S 2H; 6.75–7.6M 8H |
| 515 | 2.1S 3H; 2.2S 3H; 3.9S 3H; 4.85S 2H; 6.75–7.6M 8H |
| 542 | 1.1T 3H; 2.2S 3H; 2.7Q 2H. 3.9S 3H; 4.85S 2H; 6.7–7.6M 8H |
| 174 | 1.1Q 3H; 2.2S 3H; 2.5S 3H; 3.5D 1H; 3.85S 3H; 4.95S 2H; 6.8–7.7M 8H |
| 702 | 1.05T 3H; 2.25S 3H; 2.65Q 2H; 3.25S 3H; 3.9S 3H; 4.9S 2H; 6.7–7.6M 8H |
| 310 | 1.05T 3H; 2.55S 3H; 2.90Q 2H; 3.95S 3H; 5.10S 2H; 7.05–7.85M 8H |
| 451 | 2.25S 3H; 4.0S 3H; 6.95–8.2M 9H |
| 326 | 1.6M 2H; 2.2S 3H; 2.85T 2H; 4.0S 3H; 4.8S 2H; 6.65–7.6M 8H |
| 312 | 1.15Q 5H; 1.7Q 2H; 2.95Q 2H; 4.0S 3H; 4.85S 2H; 6.95–7.4M 7H |
| 311 | 1.1–1.6M 7H; 2.95Q 2H; 4.00S 3H; 4.85S 2H; 6.95–7.60M 8H |
| 289 | 2.1S 3H; 2.55S 3H; 4.05S 3H; 6.9–7.4M 4H |
| 314 | 1.2M 10H; 2.95Q 2H; 4.0S 3H; 4.9S 2H; 7.0–7.5M 4H |

The novel oxime ethers are suitable as fungicides.

The fungicidal oxime ethers according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Usually, the plants are sprayed or dusted with the active ingredients or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalene-sulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of formulations are given below.

I. A solution of 90 parts by weight of compound no. 56 and 10 parts by weight of N-methyl-α-pyrrolidone, which is suitable for application in the form of very fine drops.

II. A mixture of 20 parts by weight of compound no. 83, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 272, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 191, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of compound no. 137, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 316 and 97 parts by weight of particulate kaolin. The dust contains 3 wt % of the active ingredient.

VII. An intimate mixture of 30 parts by weight of compound no. 110, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 353, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 380, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

The oxime ethers are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits, or in the seeds of these plants.

The compounds are applied by treating the fungi, or the seeds, plants, materials or the soil to be protected against fungus attack with a fungicidally effective amount of the active ingredients.

The active ingredients are applied before or after infection of the materials, plants or seed by the fungi.

The oxime ethers are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
Cercospora arachidicola in groundnuts,
*Pseudocercosporella herpotrichoides* in wheat and barley,
*Pyricularia oryzae* in rice,
Phytophthora infestans in potatoes and tomatoes,
Fusarium and Verticillium species in various plants,
*Plasmopara viticola* in grapes,
Alternaria species in fruit and vegetables.

The novel compounds may also be used for protecting materials (timber), e.g., against *Paecilomyces variotii*.

Generally, the fungicidal agents contain from 0.1 to 95, and preferably from 0.5 to 90, % by weight of active ingredient.

Application rates vary, depending on the effect desired, and are from 0.02 to 3 kg of active ingredient per hectare.

When the active ingredients are used for treating seed, amounts of from 0.001 to 50, and preferably from 0.01 to 10, g per kg of seed are generally required.

When the agents according to the invention are used as fungicides, they may also be present together with, for example, herbicides, insecticides, growth regulators, other fungicides and fertilizers.

When mixed with other fungicides, the spectrum of fungicidal action is often increased.

For comparison purposes in the use example below, methyl 1-methoxyimino-1-(2-phenoxymethyl)-phenylacetate (A)—disclosed in EP 253,213—was used.

Use Example

Action on wheat mildew

Leaves of pot-grown wheat seedlings of the "Frühgold" variety were sprayed with aqueous liquors containing (dry basis) 80% of active ingredient and 20% of emulsifier, and dusted, 24 hours after the sprayed-on layer had dried, with spores of wheat mildew (*Erysiphe graminis* var. tritici). The plants were then set up in the greenhouse at from 20° to 22° C. and a relative humidity of from 75 to 80%. The extent of mildew spread was assessed after 7 days.

The results show that active ingredients 88, 92, 110, 164, 273, 277, 299, 300, 301, 304, 305, 307, 308, 649, 675, 702 and 918, when applied as 0.0015 wt % spray liquors, have a better fungicidal action (95%) than prior art active ingredient A (75%).

We claim:

1. Oxime ethers of the formula I

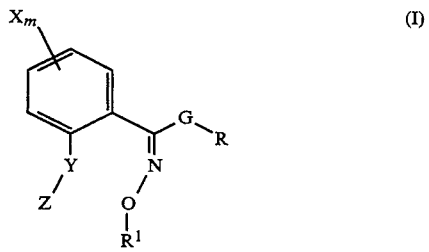

where

G is C=W or C(V)R$^8$,

W is oxygen or NR$^5$,

V is OR$^6$ or NR$^5$R$^7$,

R$^5$ is hydrogen, hydroxyl, NH$_2$, C$_1$-C$_8$-alkyl, C$_1$-C$_4$-aralkyl, C$_3$-C$_6$-cycloalkyl, C$_1$-C$_4$-alkoxy, C$_1$-C$_4$-alkylamino or C$_3$-C$_4$-dialkylamino, R$^6$,R$^7$ is hydrogen, C$_1$-C$_8$-alkyl or C$_1$-C$_4$-alkanoyl, R$^8$ is hydrogen or C$_1$-C$_8$-alkyl, R is C$_2$-C$_8$-alkenyl, C$_2$-C$_8$-alkynyl, phenyl, hetaryl or —CR$^2$R$^3$R$^4$, R$^2$,R$^4$ are each hydrogen, C$_1$-C$_8$-alkyl, arylalkyl, hetarylalkyl, alkoxyalkyl, aryloxyalkyl, aryl or hetaryl, or R$^2$,R$^4$ together with the carbon atom of which they are substituents form a C$_3$-C$_8$-cycloalkyl ring, R$^3$ is hydrogen, methyl, cyano, carboxyl or C$_1$-C$_8$-alkoxycarbonyl, or R$^2$,R$^3$ together with the carbon atom of which they are substituents form a 5-membered to 8-membered lactone ring, R$^1$ is C$_1$-C$_8$-alkyl, X are nitro, cyano, halogen, C$_1$-C$_4$-alkyl, C$_1$-C$_4$-alkoxy or C$_1$-C$_4$-haloalkyl, and m is an integer of from 0, 1, 2, 3 or 4, where the radicals X may be identical or different when m is >1, Y is O, S(O)$_n$ (n=0, 1 or 2), —O—CO—, —CO—O—, azo, carbonylamino, aminocarbonyl, aminocarbonyloxy, C$_1$-C$_8$-alkylene, C$_2$-C$_8$-alkenylene, C$_2$-C$_8$-alkynylene, C$_1$-C$_8$-alkylenoxy, oxy-C$_1$-C$_4$-alkylene, C$_1$-C$_8$-thioalkylene, oxycarbonyl-C$_1$-C$_8$-alkylene, carbonyloxy-C$_1$-C$_8$-alkylene, oxy-C$_2$-C$_8$-alkylenoxy, oxy-C$_2$-C$_8$-alkenylene, C$_1$-C$_8$-alkylamino, carbonyl-C$_1$-C$_8$-alkylamino, C$_1$-C$_8$-alkylaminocarbonyl, C$_1$-C$_8$-alkylaminocarbonyloxy, oxyimino or iminooxyalkylene, Z is C$_1$-C$_{18}$-alkyl, C$_1$-C$_4$-alkoxy-C$_1$-C$_{10}$-alkyl, C$_1$-C$_{10}$-haloalkyl, C$_2$-C$_{18}$-alkenyl, C$_3$-C$_8$-alkynyl, C$_1$-C$_4$-alkoxycarbonyl, aryl, aryl-C$_1$-C$_{10}$-alkyl, aryl-C$_2$-C$_{10}$-alkenyl, aryloxy-C$_1$-C$_{10}$-alkyl or hetaryl, where the radicals Z may be unsubstituted or substituted by cyano, formyl, nitro, halogen, C$_1$-C$_4$-alkyl, C$_1$-C$_4$-haloalkyl, C$_1$-C$_4$-alkoxy-C$_1$-C$_4$-alkyl, C$_1$-C$_4$-dialkoxy-C$_1$-C$_4$-alkyl, C$_2$-C$_4$-alkenyl, C$_2$-C$_4$-haloalkenyl, C$_1$-C$_4$-alkoxy, C$_1$-C$_4$-alkoxycarbonyl, unsubstituted or substituted C$_1$-C$_{10}$-alkoxyimino, C$_2$-C$_{10}$-alkenyloxyimino, aralkyloxyimino, unsubstituted or substituted C$_2$-C$_{10}$-alkanoyl, unsubstituted or substituted phenyl or phenoxy, or are an unsubstituted or substituted carbon-bonded 5-membered heterocyclic structure which contains from one to four identical or different heteroatoms selected from nitrogen, oxygen or sulfur, in which two adjacent substituents may form an unsubstituted or substituted aromatic or heteroaromatic ring.

2. Oxime ethers of the formula I as set forth in claim 1, where G is C=NCH$_3$, R is CR$^2$, R$^3$, R$^4$ and R$^1$ are methyl, R$^2$ and R$^3$ are hydrogen, Y is oxymethylene and Z is 2-methylphenyl.

3. Oxime ethers of the formula I as set forth in claim 1, where G is CH—OH, R is CR$^2$, R$^3$, R$^4$ and R$^1$ are methyl, R$^2$ and R$^3$ are hydrogen, Y is oxymethylene and Z is 2-methylphenyl.

4. Oxime ethers of the formula I as set forth in claim 1, where G is CH—OH, R is CR$^2$, R$^3$, R$^4$ and R$^1$ are methyl, R$^2$ and R$^3$ are hydrogen, Y is oxymethylene and Z is 2,4-dimethylphenyl.

5. Oxime ethers of the formula I as set forth in claim 1, wherein —G—R is lower alkanoyl; Y is —CH$_2$—; Z is unsubstituted phenoxy or phenoxy substituted by nitro, alkyl, alkoxy, haloalkyl, phenyl or phenoxy; R$^1$ is alkyl; and X is hydrogen, halogen, alkoxy or haloalkyl.

6. Oxime ethers of the formula I as set forth in claim 5, wherein Z is phenoxy or phenoxy substituted by alkyl and X is hydrogen.

7. Oxime ethers of the formula I as set forth in claim 6, wherein Z is phenoxy or phenoxy substituted by lower alkyl.

8. Oxime ethers of the formula I as set forth in claim 5, wherein Y is —CH$_2$—; Z is 2,5-dimethylphenoxy; —G—R is —CO—C$_2$H$_5$ and X is hydrogen.

9. Oxime ethers of the formula I as set forth in claim 1, where G is C=O.

10. Oxime ethers of the formula I as set forth in claim 1, where G is C=NR$^5$.

11. Oxime ethers of the formula I as set forth in claim 1, where G is C(R$^8$)OR$^6$.

12. Oxime ethers of the formula I as set forth in claim 1, where G is C(R$^8$)NR$^5$R$^7$.

13. A method of combating fungi, wherein the fungi, or the materials, plants or seed threatened by fungus attack, or the soil are treated with a fungicidally effective amount of an oxime ether of the formula I

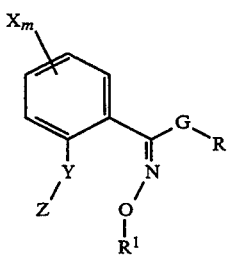

where
G is C=W or C(V)R$^8$,
W is oxygen or NR$^5$,
V is OR$^6$ or NR$^5$R$^7$,
R$^5$ is hydrogen, hydroxyl, NH$_2$, C$_1$–C$_8$-alkyl, C$_1$–C$_4$-aralkyl, C$_3$–C$_6$-cycloalkyl, C$_1$–C$_4$-alkoxy, C$_1$–C$_4$-alkylamino or C$_1$–C$_4$-dialkylamino,
R$^6$,R$^7$ is hydrogen, C$_1$–C$_8$-alkyl or C$_1$–C$_4$-alkanoyl,
R$^8$ is hydrogen or C$_1$–C$_8$-alkyl,
R is C$_2$–C$_8$-alkenyl, C$_2$–C$_8$-alkynyl, phenyl, hetaryl or —CR$^2$R$^3$R$^4$,
R$^2$,R$^4$ are each hydrogen, C$_1$–C$_8$-alkyl, arylalkyl, hetarylalkyl, alkoxyalkyl, aryloxyalkyl, aryl or hetaryl, or
R$^2$,R$^4$ together with the carbon atom of which they are substituents form a C$_3$–C$_8$-cycloalkyl ring,
R$^3$ is hydrogen, methyl, cyano, carboxyl or C$_1$–C$_8$-alkoxycarbonyl, or
R$^2$,R$^3$ together with the carbon atom of which they are substituents form a 5-membered to 8-membered lactone ring,
R$^1$ is C$_1$–C$_8$-alkyl,
X are nitro, cyano, halogen, C$_1$–C$_4$-alkyl, C$_1$–C$_4$-alkoxy or C$_1$–C$_4$-haloalkyl, and
m is an integer of from 0, 1, 2, 3 or 4, where the radicals X may be identical or different when m is >1,
is O, S(O)$_n$ (n=0, 1 or 2), —O—CO—, —CO—O—, azo, carbonylamino, aminocarbonyl, aminocarbonyloxy, C$_1$–C$_8$-alkylene, C$_2$–C$_8$-alkenylene, C$_2$–C$_8$-alkynylene, C$_1$–C$_8$-alkylenoxy, oxy-C$_2$–C$_4$-alkylene, C$_1$–C$_8$-thioalkylene, oxycarbonyl-C$_1$–C$_8$-alkylene, carbonyloxy-C$_1$–C$_8$-alkylene, oxy-C$_2$–C$_8$-alkylenoxy, oxy-C$_2$–C$_8$-alkenylene, C$_1$–C$_8$-alkylamino, carbonyl-C$_1$–C$_8$-alkylamino, C$_1$–C$_8$-alkylaminocarbonyl, C$_1$–C$_8$-alkylaminocarbonyloxy, oxyimino or iminooxyalkylene, is C$_1$–C$_{18}$-alkyl, C$_1$–C$_4$-alkoxy-C$_1$–C$_{10}$-alkyl, C$_1$–C$_{10}$-haloalkyl, C$_2$–C$_{18}$-alkenyl, C$_3$–C$_8$-alkynyl, C$_1$–C$_4$-alkoxycarbonyl, aryl, aryl-C$_1$–C$_{10}$-alkyl, aryl-C$_2$–C$_{10}$-alkenyl, aryloxy-C$_1$–C$_{10}$-alkyl or hetaryl,
where the radicals Z may be unsubstituted or substituted by cyano, formyl, nitro, halogen, C$_1$–C$_4$-alkyl, C$_1$–C$_4$-haloalkyl, C$_1$–C$_4$-alkoxy-C$_1$–C$_4$-alkyl, C$_1$–C$_4$-dialkoxy-C$_1$–C$_4$-alkyl, C$_2$–C$_4$-alkenyl, C$_2$–C$_4$-haloalkenyl, C$_1$–C$_4$-alkoxy, C$_1$–C$_4$-alkoxycarbonyl, unsubstituted or substituted C$_1$–C$_{10}$-alkoxyimino, C$_2$–C$_{10}$-alkenyloxyimino, aralkyloxyimino, unsubstituted or substituted C$_2$–C$_{10}$-alkanoyl, unsubstituted or substituted phenyl or phenoxy, or are an unsubstituted or substituted carbon-bonded 5-membered heterocyclic structure which contains from one to four identical or different heteroatoms selected from nitrogen, oxygen or sulfur, in which two adjacent substituents may form an unsubstituted or substituted aromatic or heteroaromatic ring.

14. A method for combating fungi as set forth in claim 13, wherein in the oxime ethers of the formula I, —G—R is lower alkanoyl; Y is —CH$_2$—; Z is unsubstituted phenoxy or phenoxy substituted by nitro, alkyl, alkoxy, haloalkyl, phenyl or phenoxy; R$^1$ is alkyl; and X is hydrogen, halogen, alkoxy or haloalkyl.

15. A method for combating fungi as set forth in claim 14, wherein Z in the oxime ethers of the formula I is phenoxy or phenoxy substituted by alkyl and X is hydrogen.

16. A method for combating fungi as set forth in claim 15, wherein in the oxime ethers of the formula I is phenoxy or phenoxy substituted by lower alkyl.

17. A method of combating fungi as set forth in claim 14, wherein in the oxime ethers of the formula I, Y is —CH$_2$—; Z is 2,5-dimethylphenoxy; —G—R is —CO—C$_2$H$_5$ and X is hydrogen.

18. A fungicide containing an inert carrier and a fungicidally effective amount of an oxime ether of the formula I

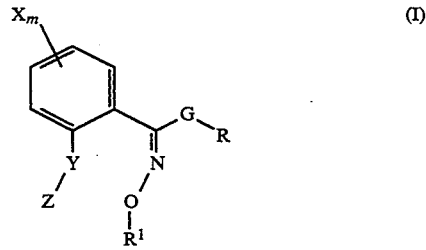

G is C=W or C(V)R$^8$,
W is oxygen or NR$^5$,
V is OR$^6$ or NR$^5$R$^7$,
R$^5$ is hydrogen, hydroxyl, NH$_2$, C$_1$–C$_8$-alkyl, C$_1$–C$_4$-aralkyl, C$_3$–C$_6$-cycloalkyl, C$_1$–C$_4$-alkoxy, C$_1$–C$_4$-alkylamino or C$_1$–C$_4$-dialkylamino,
R$^6$,R$^7$ is hydrogen, C$_1$–C$_8$-alkyl or C$_1$–C$_4$-alkanoyl,
R$^8$ is hydrogen or C$_1$–C$_8$-alkyl,
R is C$_2$–C$_8$-alkenyl, C$_2$–C$_8$-alkynyl, phenyl, hetaryl or —CR$^2$R$^3$R$^4$,
R$^2$,R$^4$ are each hydrogen, C$_1$–C$_8$-alkyl, arylalkyl, hetarylalkyl, alkoxyalkyl, aryloxyalkyl, aryl or hetaryl, or
R$^2$,R$^4$ together with the carbon atom of which they are substituents form a C$_3$–C$_8$-cycloalkyl ring,
R$^3$ is hydrogen, methyl, cyano, carboxyl or C$_1$–C$_8$-alkoxycarbonyl, or
R$^2$,R$^3$ together with the carbon atom of which they are substituents form a 5-membered to 8-membered lactone ring,
R$^1$ is C$_1$–C$_8$-alkyl,
X are nitro, cyano, halogen, C$_1$–C$_4$-alkyl, C$_1$–C$_4$-alkoxy or C$_1$–C$_4$-haloalkyl, and
m is an integer of from 0, 1, 2, 3 or 4, where the radicals X may be identical or different when m is >1,
Y is O, S(O)$_n$ (n=0, 1 or 2), —O—CO—, —CO—O—, azo, carbonylamino, aminocarbonyl, aminocarbonyloxy, C$_1$–C$_8$-alkylene, C$_2$–C$_8$-alkenylene, C$_2$–C$_8$-alkynylene, C$_1$–C$_8$-alkylenoxy, oxy-C$_1$–C$_4$-alkylene, C$_1$–C$_8$-thioalkylene, oxycarbonyl-C$_1$–C$_8$-alkylene, carbonyloxy-C$_1$–C$_8$-alkylene, oxy-C$_2$–C$_8$-alkylenoxy, oxy-C$_2$–C$_8$-alkenylene, C$_1$–C$_8$-alkylamino, carbonyl-C$_1$–C$_8$-alkylamino, C$_1$–C$_8$-alkylaminocarbonyl, C$_1$–C$_8$-alkylaminocarbonyloxy, oxyimino or iminooxyalkylene, Z is $C_1$–$C_{18}$-alkyl, $C_1$–$C_4$-alkoxy-$C_1$–$C_{10}$-alkyl, $C_1$–$C_{10}$-haloalkyl, $C_2$–$C_{18}$-alkenyl, $C_3$–$C_8$-alkynyl, $C_1$–$C_4$-alkoxycarbonyl, aryl, aryl-$C_1$–$C_{10}$-alkyl, aryl-$C_2$–$C_{10}$-alkenyl, aryloxy-$C_1$–$C_{10}$-alkyl or hetaryl, where the radicals Z may be unsubstituted or substituted by cyano, formyl, nitro, halogen, $C_1$–$C_4$-alkyl, $C_1$–$C_4$-haloalkyl, $C_1$–$C_4$-alkoxy-$C_1$–$C_4$-alkyl, $C_1$–$C_4$-dialkoxy-$C_1$–$C_4$-alkyl, $C_2$–$C_4$-alkenyl, $C_2$–$C_4$-haloalkenyl, $C_1$–$C_4$-alkoxy, $C_1$–$C_4$-alkoxycarbonyl, unsubstituted or substituted $C_1$–$C_{10}$-alkoxyimino, $C_2$–$C_{10}$-alkenyloxyimino, aralkyloxyimino, unsubstituted or substituted $C_2$–$C_{10}$-alkanoyl, unsubstituted or substituted phenyl or phenoxy, or are an unsubstituted or substituted carbon-bonded 5-membered heterocyclic structure which contains from one to four identical or different heteroatoms selected from nitrogen, oxygen or sulfur, in which two adjacent substituents may form an unsubstituted or substituted aromatic or heteroaromatic ring.

19. A fungicide as set forth in claim 18, wherein in the oxime ethers of the formula I, —G—R is lower alkanoyl; Y is —$CH_2$—; Z is unsubstituted phenoxy or phenoxy substituted by nitro, alkyl, alkoxy, haloalkyl, phenyl or phenoxy; $R^1$ is alkyl; and X is hydrogen, halogen, alkoxy or haloalkyl.

20. A fungicide as set forth in claim 19, wherein in the oxime ethers of the formula I Z is phenoxy or phenoxy substituted by alkyl and X is hydrogen.

21. A fungicide as set forth in claim 20, wherein in the oxime ethers of the formula I Z phenoxy or phenoxy substituted by lower alkyl.

22. A fungicide as set forth in claim 19, wherein in the oxime ethers of the formula I Y is —$CH_2$—; Z is 2,5-dimethylphenoxy; —G—R is —CO—$C_2H_5$ and X is hydrogen.

* * * * *